US009018364B2

(12) United States Patent  
Benjamin

(10) Patent No.: US 9,018,364 B2
(45) Date of Patent: *Apr. 28, 2015

(54) NUCLEIC ACIDS, COMPOSITIONS AND METHODS FOR THE EXCISION OF TARGET NUCLEIC ACIDS

(75) Inventor: Kirsten Benjamin, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 729 days.

This patent is subject to a terminal disclaimer.

(21) Appl. No.: 13/220,553

(22) Filed: Aug. 29, 2011

(65) Prior Publication Data

US 2012/0052582 A1 Mar. 1, 2012

Related U.S. Application Data

(60) Provisional application No. 61/378,350, filed on Aug. 30, 2010.

(51) Int. Cl.
| | |
|---|---|
| C07H 21/02 | (2006.01) |
| C12N 15/74 | (2006.01) |
| C12N 15/81 | (2006.01) |
| C12N 15/75 | (2006.01) |

(52) U.S. Cl.
CPC .............. *C12N 15/81* (2013.01); *C12N 15/74* (2013.01); *C12N 15/75* (2013.01)

(58) Field of Classification Search
CPC ................................ C12N 15/81; C12N 15/75
See application file for complete search history.

(56) References Cited

U.S. PATENT DOCUMENTS

| | | |
|---|---|---|
| 7,919,605 B1 | 4/2011 | Benjamin |
| 2005/0172365 A1 | 8/2005 | Puchta et al. |
| 2011/0053272 A1 * | 3/2011 | Benders et al. ............... 435/455 |

OTHER PUBLICATIONS

Chevalier et al., "Homing endonucleases: structural and functional insight into the catalysts of intron/intein mobility", Nucleic Acids Res. vol. 29, No. 18, pp. 3757-3774 (2001).
Ivanov et al., "Genetic requirements for the single-strand annealing pathway of double-strand break repair in *Saccharomyces cerevisiae*", Genetics 142(3), pp. 693-704 (1996) Abstract 1 pg.
Nagai et al., "Karyopherin-mediated nuclear import of the homing endonuclease VMA1-derived endonuclease is required for self-propagation of the coding region", Mol. Cell Biol. 23(5), pp. 1726-36 (2003) Abstract 1 pg.
Stoddard, "Homing endonuclease structure and function", Quarterly Rev. of Biophysics 38, pp. 49-95 (2006) Abstract 1 pg.
Zeng et al., "A free-standing homing endonuclease targets an intron insertion site in the psbA gene of cyanophages", Curr. Biol. 19(3), pp. 218-22 (2009) Abstract 1 pg.

(Continued)

*Primary Examiner* — Reza Ghafoorian
(74) *Attorney, Agent, or Firm* — Squire Patton Boggs (US) LLP

(57) ABSTRACT

Nucleic acids, compositions, and methods that allow for the excision of one or more loci from the genome of a host cell are provided herein. In particular, provided herein is an excisable nucleic acid construct comprising, in a 5' to 3' orientation: a first tandem repeat nucleic acid, a first homing endonuclease recognition site, a target nucleic acid, a second homing endonuclease recognition site, and a second tandem repeat nucleic acid. In some embodiments, the excisable nucleic acid construct is integrated into the host cell genome, and the target nucleic acid can be excised from the host cell genome by contacting the homing endonuclease recognition sites with one or more appropriate homing endonucleases.

18 Claims, 4 Drawing Sheets

(56) References Cited

OTHER PUBLICATIONS

Figure 1:
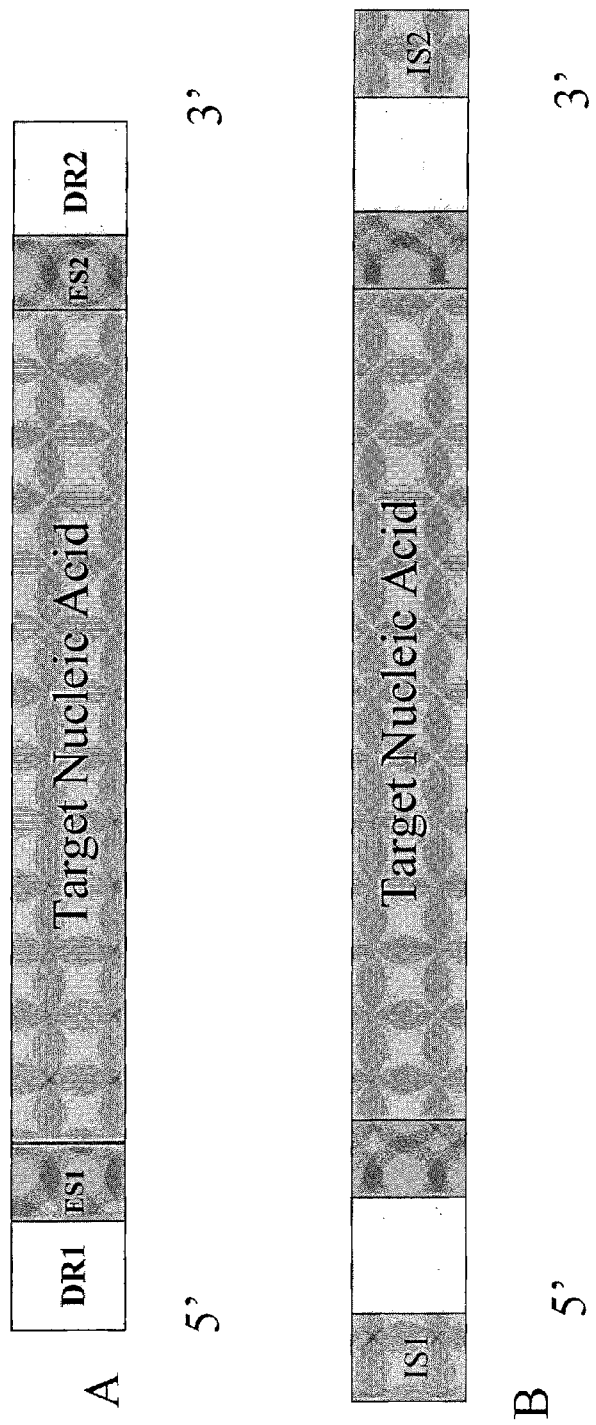

International Search Report for PCT/US2011/049615, mailed Jan. 9, 2012, 5 pgs.

Kuhlman et al., "Site-specific chromosomal integration of large synthetic constructs", Nucl. Acids Res. vol. 38, No. 6, 10 pgs. (2010).

Lambert et al., "Analysis of intrachromosomal homologous recombination in mammalian cell, using tandem repeat sequences", Mutation Res. vol. 433, No. 3, pp. 159-168 (1999).

López et al., "Versatile dual-technology system for markerless allele replacement in *Burkholderia pseudomallei*", Appl. and Environ. Microbiology vol. 75, No. 20, pp. 6496-6503 (2009).

Maria Marcaida et al., "Homing endonucleases: from basics to therapeutic applications", CMLS Cel. and Mol. Life Sciences vol. 67, No. 5, pp. 727-748 (2009).

Noskov et al., "Tandem repeat coupled with endonuclease cleavage (TREC): a seamless modification tool for genome engineering in yeast", Nucl. Acids Res. vol. 38, No. 8, pp. 2570-2576 (2010).

Stoddard, B.L., Homing endonuclease structure and function (2006) *Quarterly Reviews of Biophysics* 38:49-95.

\* cited by examiner

US 9,018,364 B2

NUCLEIC ACIDS, COMPOSITIONS AND METHODS FOR THE EXCISION OF TARGET NUCLEIC ACIDS

This application claims benefit under 35 U.S.C. §119(e) of U.S. Provisional Application No. 61/378,350, filed Aug. 30, 2010, which is hereby incorporated by reference in its entirety.

1. FIELD OF THE INVENTION

The nucleic acids, compositions, and methods provided herein generally relate to the fields of molecular biology and genetic engineering.

2. BACKGROUND

Genetic engineering techniques to excise a target nucleic acid from a host cell genome or an episome are needed in a variety of fields including metabolic engineering, industrial microbiology, synthetic biology, and basic molecular genetics research. Previous methods for removal of target nucleic acids, however, have been restricted and limited in application. Site specific recombinase methods of removal, for example, leave behind deleterious specific recombinase binding sites that create potential genomic instabilities within the host cells. Other methods can produce excision events at low frequency, thus necessitating methods for growth-selection of rare host cells that undergo the excision event. There exists a need for nucleic acids, compositions, and methods that can allow for high frequency and high fidelity excision of a target nucleic acid from a host cell genome or an episome without creating potential genomic instabilities.

3. SUMMARY

Provided herein are nucleic acids, compositions, and methods that allow for the excision of one or more loci from the genome of a host cell. In a first aspect, provided herein is an excisable nucleic acid construct comprising, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In some embodiments, the excisable nucleic acid construct is integrated into the host cell genome. In some embodiments, the second homing endonuclease recognition site is optional.

The first and second homing endonuclease recognition sites allow for a homing endonuclease to cleave the excisable nucleic acid construct. A homing endonuclease bound to a homing endonuclease recognition site can cleave the excisable nucleic acid construct at or adjacent to the homing endonuclease recognition site. In some embodiments, each of the first and second homing endonuclease recognition sites independently comprises 14-40 nucleotide base pairs. In some embodiments, each of the first and second homing endonuclease recognition sites independently consists of 14-40 nucleotide base pairs. In some embodiments, each of the homing endonuclease recognition sites independently consists of 20-40 nucleotide base pairs. In some embodiments, each of the homing endonuclease recognition sites independently consists of 25-40 nucleotide base pairs. In some embodiments, each of the homing endonuclease recognition sites independently consists of 30-40 nucleotide base pairs. In some embodiments, each of the homing endonuclease recognition sites independently consists of 35-40 nucleotide base pairs. In some embodiments, each of the homing endonuclease recognition sites independently consists of 24 nucleotide base pairs.

In some embodiments, at least one of the first or second homing endonuclease recognition sites is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, each of the first and second homing endonuclease recognition sites independently is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease.

In some embodiments, at least one of the first or second homing endonuclease recognition sites is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI.

In certain embodiments, each of the first and second homing endonuclease recognition sites independently is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. In particular embodiments, at least one of the first or second homing endonuclease recognition sites is a recognition site for I-SceI. In particular embodiments, at least one of the first or second homing endonuclease recognition sites is a recognition site for F-CphI.

After cleavage of the target nucleic acid, repair of the host cell genome can occur through intrachromosomal recombination facilitated by the first and second tandem repeats. In some embodiments, each of the first and second tandem repeat nucleic acids independently comprises at least 18 nucleotide base pairs. In some embodiments, each of the first and second tandem repeat nucleic acids independently consists of 18 to 500 nucleotide base pairs. In some embodiments, each of the first and second tandem repeat nucleic acids independently consists of 18 to 200 nucleotide base pairs. In some embodiments, the host cell is a yeast cell, and each of the first and second tandem repeat nucleic acids independently consists of 18 to 200 nucleotide base pairs.

In some embodiments, the target nucleic acid encodes a selectable marker. In some embodiments, the selectable marker is selected from the group consisting of: URA3, hygromycin B phosphotransferase, aminoglycoside phosphotransferase, zeocin resistance gene and phosphinothricin N-acetyltransferase.

In some embodiments, the excisable nucleic acid construct described above further comprises a first genomic integration site linked 5' of the first tandem repeat and a second genomic integration site linked 3' of the second tandem repeat. Advantageously, the first and second genomic integration sites can facilitate integration of the excisable nucleic acid construct into a host cell genome.

In another aspect, provided herein is a host cell comprising the excisable nucleic acid construct described above. In some embodiments, the excisable nucleic acid construct further comprises a first integration site linked 5' of the first tandem repeat and a second integration site linked 3' of the second tandem repeat.

In some embodiments, the host cell is a prokaryote. In some embodiments, the host cell is a eukaryote. In certain embodiments, the host cell is a unicellular eukaryotic organism. In certain embodiments, the host cell is a yeast cell. In certain embodiments, the host cell is a haploid yeast cell. In other embodiments, the host cell is a diploid yeast cell. In certain embodiments, the host cell is a yeast cell of the strain *S. cerevisiae*.

In some embodiments the host cell further comprises a vector comprising a homing endonuclease nucleic acid encoding a homing endonuclease, wherein the homing endonuclease is capable of binding to and cleaving at or adjacent to at least one of the first and second homing endonuclease recognition sites. In certain embodiments, the vector comprises a homing endonuclease nucleic acid encoding a homing endonuclease capable of binding to and cleaving at or adjacent to each of the first and second homing endonuclease recognition sites.

In some embodiments, the vector comprises a promoter element that controls the expression of the homing endonuclease nucleic acid encoding the homing endonuclease. In some embodiments, the promoter element is an inducible promoter. In some embodiments, the promoter element is a constitutive promoter.

In another aspect, provided herein is a host cell comprising an excisable nucleic acid construct described above, integrated into the host cell genome. In certain embodiments, the excisable nucleic acid construct comprises, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In some embodiments, the host cell further comprises a vector comprising a homing endonuclease nucleic acid that encodes a homing endonuclease capable of binding to and cleaving at or adjacent to at least one of the first or second homing endonuclease recognition sites. In some embodiments, the homing endonuclease nucleic acid encodes a homing endonuclease capable of binding to and cleaving at or adjacent to each of the first and second homing endonuclease recognition sites. In some embodiments, the homing endonuclease is I-SceI. In some embodiments, the homing endonuclease is F-CphI.

In another aspect, provided herein is a kit comprising the excisable nucleic acid construct described above; and a vector comprising a homing endonuclease nucleic acid encoding a homing endonuclease capable of binding to and cleaving at or adjacent to at least one of the first or second homing endonuclease recognition sites. In some embodiments, the homing endonuclease is I-SceI. In some embodiments, the homing endonuclease is F-CphI.

In another aspect, provided herein is a method of excising at least one target nucleic acid from the genome of a host cell. In certain embodiments, the host cell comprises a nucleic acid, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In certain embodiments, the method comprises expressing a homing endonuclease in the host cell such that the homing endonuclease cleaves at or adjacent to at least one of the first or second homing endonuclease recognition sites. In some embodiments of the method, the homing endonuclease cleaves at or adjacent to each of the first and second homing endonuclease recognition sites. In some embodiments, at least one of the first and second homing endonuclease recognition sites is a recognition site for I-SceI. In some embodiments, at least one of the first and second homing endonuclease recognition sites is a recognition site for F-CphI.

In another aspect, provided herein is a method of simultaneously excising at least two target nucleic acids from the genome of a host cell comprising at least two excisable nucleic acid constructs, wherein each excisable nucleic acid construct independently comprises, in a 5' to 3' orientation: a) a first tandem repeat nucleic acid; b) a first homing endonuclease recognition site; c) a target nucleic acid; d) a second homing endonuclease recognition site; and e) a second tandem repeat nucleic acid. In some embodiments, the method comprises contacting the at least two excisable nucleic acid constructs with a homing endonuclease in the host cell such that the homing endonuclease cleaves at or adjacent to at least one of the first or second homing endonuclease recognition sites of each excisable nucleic acid construct. In some embodiments, the method comprises contacting the at least two excisable nucleic acid constructs with one or more homing endonucleases in the host cell such that the one or more homing endonucleases cleave at or adjacent to at least one of the first or second homing endonuclease recognition sites of each excisable nucleic acid construct.

Advantageously, a genomic nucleic acid with an excision of the target nucleic acid is formed by recombination mediated by the first and second tandem repeat. In some embodiments, the newly formed genomic nucleic acid comprises a third tandem repeat, created as a product of the recombination of the first and second tandem repeats. In advantageous embodiments, the only portion of the excisable endonuclease construct remaining in the host cell is the third tandem repeat, which can be as few as 18 nucleotide base pairs in length.

The compositions and methods provided herein advantageously allow for the precise and efficient excision of one or more target nucleic acids from a host cell genome or an episome without creating potential genomic instabilities. Many instances in genetic engineering exist where there may be a need to remove a target nucleic acid at a chosen genomic or episomal location. For example, the compositions and method described above can advantageously be used for removing selectable markers to enable their reuse in the same host cell or its progeny. "Marker recycling" may be useful in situations requiring multiple genetic engineering events in a host organism with a limited battery of selectable markers. The compositions and methods provided may also be used to remove unwanted nucleic acids (e.g. an antibiotic resistance marker) from a host cell before releasing the host cell in a manufacturing or natural environment.

Further, the compositions and methods described can be used for turning on or off expression of a particular gene in a host cell and its progeny. To turn off a gene, the compositions and methods described can be used, for example, to excise the nucleic acids representing one or more of the gene's cis-acting regulatory elements, some or all of its coding sequence, or one or more of its transcriptional activators. To turn on expression of a gene, an interfering stretch of nucleic acids can be excised to create required adjacent interactions between the elements needed for expression of the particular gene.

4. BRIEF DESCRIPTION OF THE FIGURES

FIG. 1. Embodiments of an excisable nucleic acid construct. FIG. 1A: An excisable nucleic acid construct comprising, in a 5' to 3' orientation: a first tandem repeat nucleic acid ("DR1"); a first homing endonuclease recognition site ("ES1"); a target nucleic acid ("Target nucleic acid"); a second homing endonuclease recognition site ("ES2"); and a second tandem repeat nucleic acid ("DR2"). FIG. 1B: The excisable nucleic acid construct depicted in FIG. 1A, further comprising a first integration site (IS1) linked 5' of the first homing endonuclease recognition site and a second integration site (IS2) linked 3' of the second tandem repeat nucleic acid.

Figure 2:
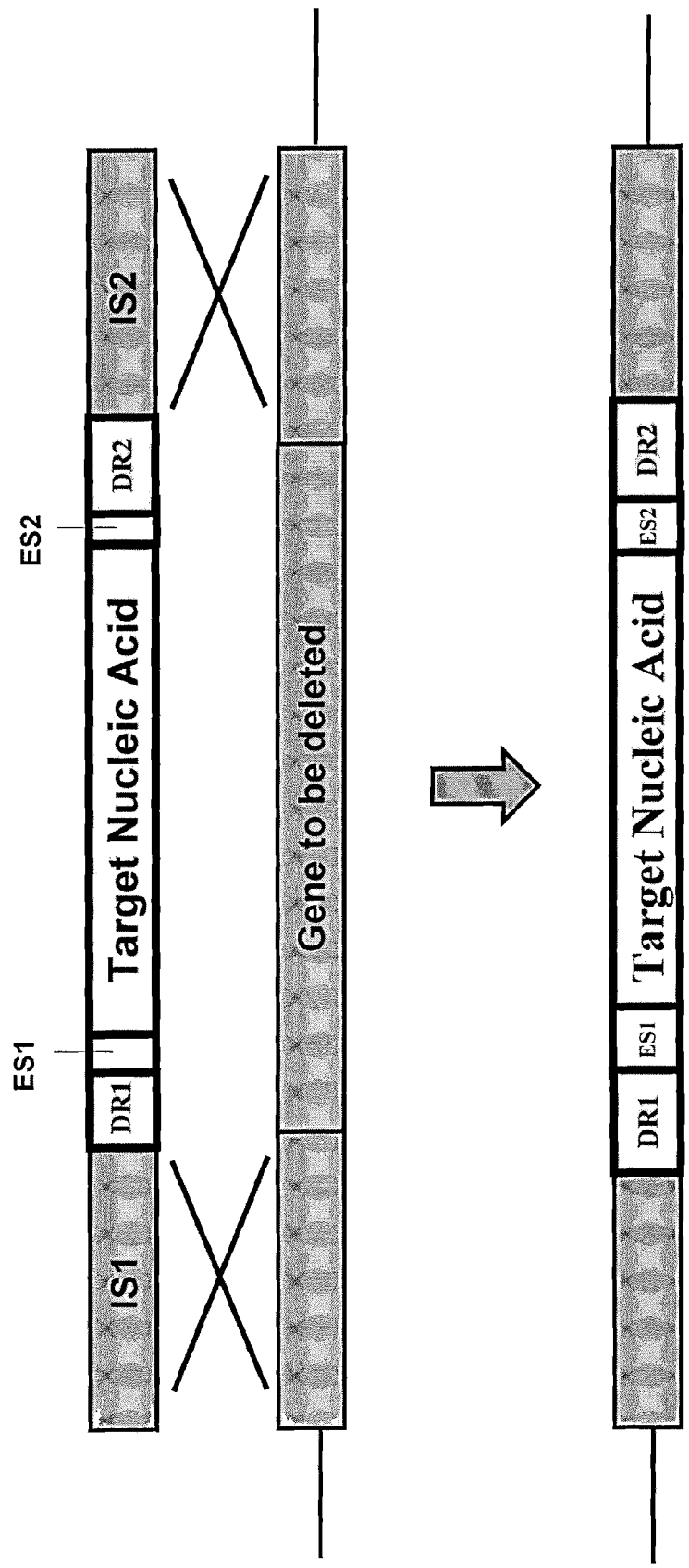

FIG. 2. An excisable nucleic acid construct is transformed to knock-out and/or knock-in a target nucleic acid into a specific locus of the host cell genome through integration site mediated homologous recombination. The target nucleic acid is flanked by two copies of a homing endonuclease restriction site (ES1 and ES2, respectively) which in turn are flanked by two tandem repeats (DR1 and DR2, respectively) that direct repair after cleavage.

Figure 3:
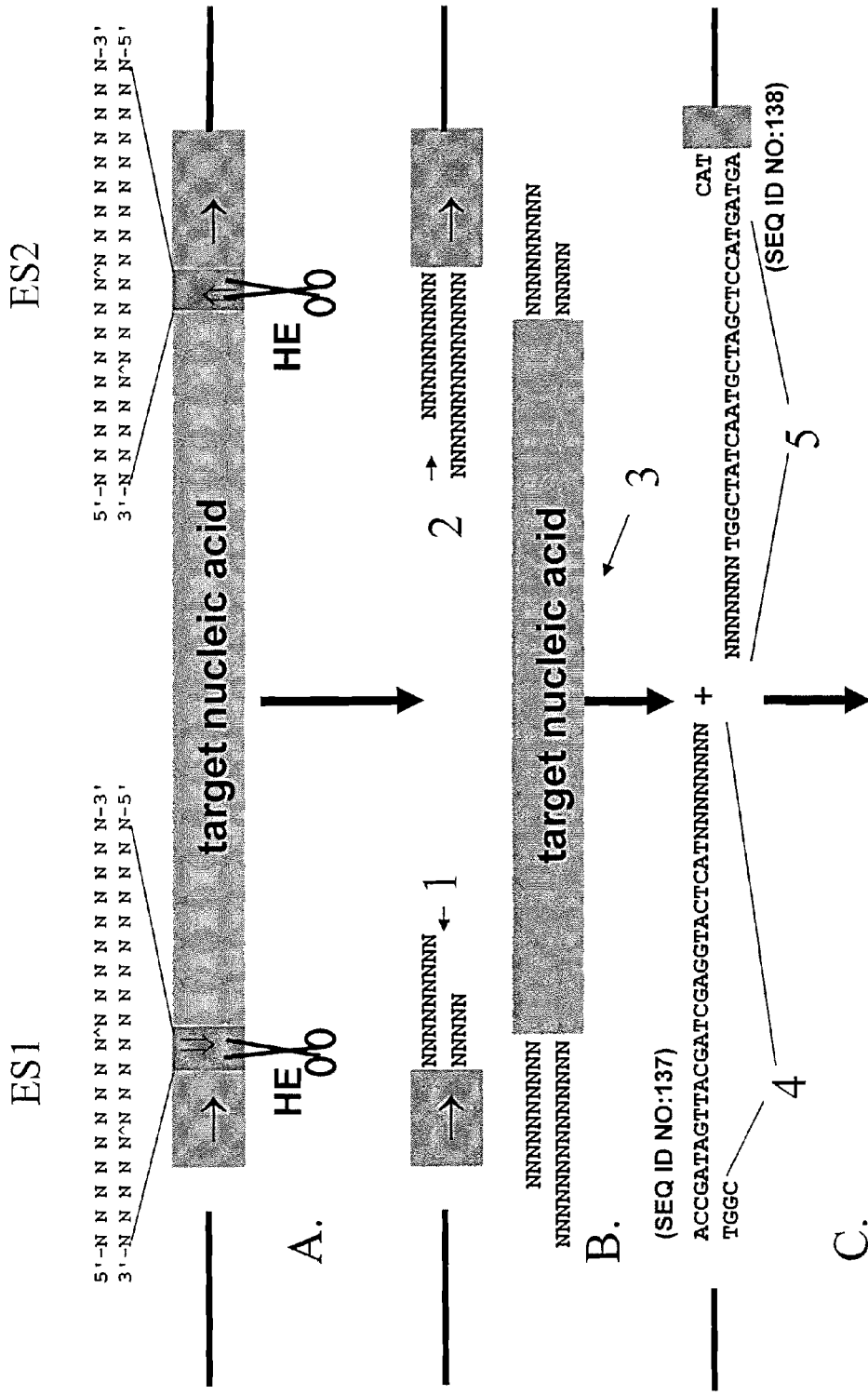

FIG. 3. Excision of a target nucleic acid. In some embodiments, cleavage of each of the first and second homing (FIG. 3A) endonuclease recognition sites (ES1 and ES2, respectively) by one or more corresponding homing endonucleases (HE) creates three nucleic acid fragments: (1) a left arm of genomic or episomal nucleic acid (2) a nucleic acid fragment comprising the target nucleic acid and (3) a right arm of genomic or episomal nucleic acid (FIG. 3B). After cleavage, endogenous 5' to 3' exonucleases in the host cell rapidly degrade one strand of each nucleic acid fragment, destroying the nucleic acid fragment comprising the target nucleic acid and leaving 3' tails on the left (4) and right arms (5) of genomic or episomal nucleic acid (FIG. 3C).

Figure 4:
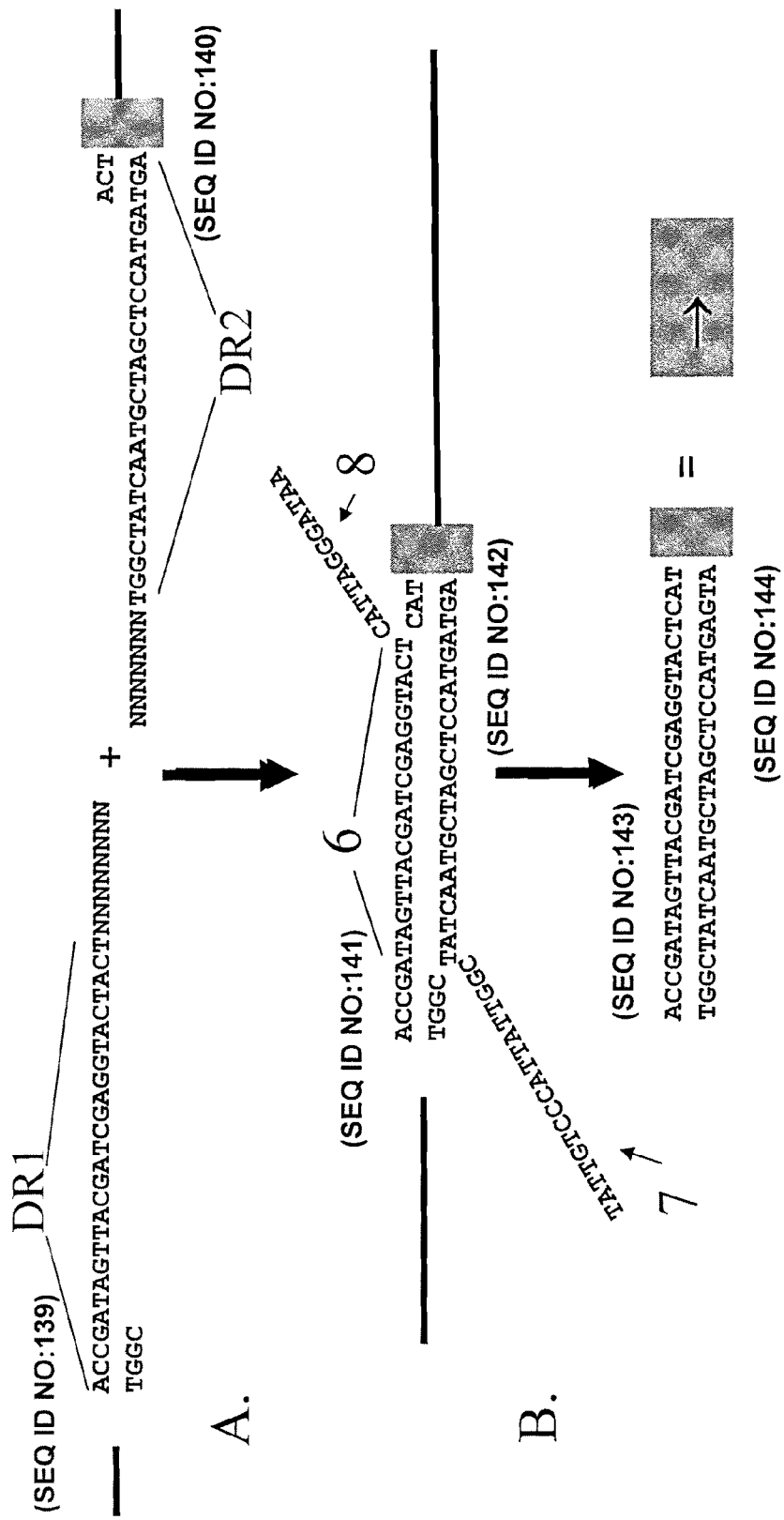

FIG. 4. Excision of a target nucleic acid (cont'd). The single strand degradation of the left and right arms expose a tandem repeat found on each arm, the tandem repeats complementary to one another (FIG. 4A). The complementary regions on the tandem repeats form a heteroduplex (FIG. 4B,6) and undergo recombination facilitated by host cell proteins. The extreme 3' ends of the single strand of the right (7) and left arms (8) are not complementary and thus are not part of the heteroduplex formed by the complementary portions of the first and second tandem repeats. These extreme non complementary 3' ends can be cleaved by a flap nuclease. Finally, repair DNA synthesis and DNA ligase fill in the heteroduplex and seal nicks, creating an intact genomic or episomal nucleic acid with a precise excision of the target nucleic acid (FIG. 4C).

5. DETAILED DESCRIPTION OF THE EMBODIMENTS

5.1 Definitions

As used herein, the term "homing endonuclease" refers to any one of several endonucleases whose natural biological function is to catalyze a gene conversion event to spread the endonuclease-encoding allele of a particular gene to endonuclease-free alleles of the gene. See, e.g, Chevalier, *Nucleic Acids Res* 1(29): 3757-74 (2001); Jacquier, *Cell* 41: 383-94 (1985). At least five different families of homing endonucleases are known, including: 1) LAGLIDADG (SEQ ID NO: 1) homing endonucleases, 2) HNH homing endonucleases, 3) His-Cys box homing endonucleases, 4) GIY-YIG (SEQ ID NO: 2) homing endonucleases and 5) cyanobacterial homing endonucleases. See, e.g., Stoddard, *Quarterly Review of Biophysics* 38(1): 49-95 (2006). Examples of specific homing endonucleases from these families include but are not limited to: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. Those of skill in the art will recognize that natural or artificial variants of such endonucleases that recognize, and cleave at or adjacent to, the same or similar homing endonuclease restriction sites are included within this definition.

As used herein, the term "homing endonuclease recognition site" refers to a nucleic acid that is recognized by a specific homing endonuclease. Subsequent to binding of the homing endonuclease recognition site, the homing endonuclease can create a double strand break at or adjacent to the homing endonuclease recognition site.

As used herein, the term "adjacent" refers to a distance of about 1 to about 100, 1 to about 75, 1 to about 50, 1 to about 25, 1 to about 20, 1 to about 15, 1 to about 10, or 1 to about 5 nucleotides from a particular nucleic acid.

As used herein, the terms "cleaves" and cleavage" with respect to homing endonucleases refer to the act of creating a double stranded break in a particular nucleic acid. The double strand break can leave a blunt end or sticky end (i.e., 5' or 3' overhang), as understood by those of skill in the art.

As used herein, the term "tandem repeat" refers to a nucleic acid that is part of a group of two or more nucleic acids, wherein each member shares sufficient nucleotide homology with respect to the other member(s) to mediate recombination between one another. Tandem repeats are arranged in either the same orientation ("direct tandem repeat") or in the opposite orientation ("inverted tandem repeat") with respect to the other member of the tandem.

As used herein, the term "target DNA segment" refers to any target DNA segment that is to be excised from a host cell genome using the compositions and methods provided herein. Useful examples include but are not limited to: a protein-coding sequence, selectable marker, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, the target DNA segment can be of natural origin. Alternatively, a target DNA segment can be completely of synthetic origin, produced in vitro. Furthermore, a target DNA segment can comprise any combination of isolated naturally occurring DNA molecules, or any combination of an isolated naturally occurring DNA molecule and a synthetic DNA molecule. For example, a target DNA segment may comprise a heterologous promoter operably linked to a protein coding sequence, a protein coding sequence linked to a poly-A tail, a protein coding sequence linked in-frame with a epitope tag coding sequence, and the like.

As used herein, the term "vector" is used in reference to extrachromosomal nucleic acid molecules capable of replication in a cell and to which an insert sequence can be operatively linked so as to bring about replication of the insert sequence. Useful examples include but are not limited to circular DNA molecules such as plasmid constructs, phage constructs, cosmid vectors, etc., as well as linear nucleic acid constructs (e.g., lambda phage constructs, bacterial artificial chromosomes (BACs), yeast artificial chromosomes (YACs), etc.). A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate).

As used herein, the term "genomic" refers to both chromosomal and episomal DNA contained in a host cell.

5.2 Excisable Nucleic Acid Constructs

In one aspect, provided herein is an excisable nucleic acid construct comprising, in a 5' to 3' orientation: a) a first tandem repeat (DR1), b) a target DNA segment (D), and c) a second tandem repeat (DR2), as well as a first homing endonuclease recognition site (ES1) located either between DR1 and D or between D and DR2, and optionally a second homing endonuclease recognition site (ES2) located either between D and DR2 or between DR1 and D, respectively (FIG. 1A). Thus, in some embodiments, the excisable nucleic acid construct comprises, in a 5' to 3' orientation: a) a first tandem repeat (DR1), b) a first homing endonuclease recognition site (ES1), c) a target DNA segment (D), and d) a second tandem repeat (DR2). In some embodiments, the excisable nucleic acid construct comprises, in a 5' to 3' orientation: a) a first tandem repeat (DR1), b) a target DNA segment (D), c) a first homing endonuclease recognition site (ES1), and d) a second tandem repeat (DR2). In some embodiments, the excisable nucleic acid construct comprises, in a 5' to 3' orientation: a) a first tandem repeat (DR1), b) a first homing endonuclease recognition site (ES1), c) a target DNA segment (D), d) a second homing endonuclease recognition site (ES2), and e) a second tandem repeat (DR2).

In some embodiments, the excisable nucleic acid construct described above further comprises a first genomic integration sequence (IS1) linked 5' of the first tandem repeat and a second genomic integration sequence linked 3' of the second tandem repeat (IS2). Thus, in some embodiments, the excisable nucleic acid construct comprises, in a 5' to 3' orientation: a) a first integration sequence (IS1), b) a first tandem repeat (DR1), c) a first homing endonuclease recognition site (ES1), d) a target DNA segment (D), e) a second tandem repeat (DR2), and f) a second integration sequence (IS2). In some embodiments, the excisable nucleic acid construct comprises, in a 5' to 3' orientation: a) a first integration sequence (IS1), b) a first tandem repeat (DR1), c) a target DNA segment (D), d) a first homing endonuclease recognition site (ES1), e) a second tandem repeat (DR2), and f) a second integration sequence (IS2). In some embodiments, the excisable nucleic acid construct comprises, in a 5' to 3' orientation: a) a first integration sequence (IS1), b) a first tandem repeat (DR1), c) a first homing endonuclease recognition site (ES1), d) a target DNA segment (D), e) a second homing endonuclease recognition site (ES2), f) a second tandem repeat (DR2), and g) a second integration sequence (IS2).

Advantageously, the first and second integration sequences can facilitate integration of the excisable nucleic acid construct into a host cell genome. The excisable nucleic acid construct, when integrated into a host cell genome, allows for high frequency and high fidelity excision of the target DNA segment (D) from the host cell genome. In some embodiments, the excisable nucleic acid construct is a linear DNA molecule.

The excisable nucleic acid construct may be used to facilitate the excision of selectable markers in genetic engineering applications or for the removal of antibiotic resistance markers before release of organisms into a manufacturing environment or the natural environment. It may also be used to permanently turn on or turn off expression of genes in a host cell and its descendents. To prevent expression of a gene, its cis-acting regulatory sequences, its coding sequence, or a gene encoding a transcriptional activator can be excised. To trigger expression of genes, the gene or DNA binding site for a transcriptional repressor can be excised to allow expression of its regulated gene(s), or an interfering stretch of DNA can be excised to create required adjacent interactions between the elements needed for expression of particular genes.

The excisable nucleic acid construct can be generated by any technique apparent to one skilled in the art. In certain embodiments, the excisable nucleic acid construct is generated using polymerase chain reaction (PCR) and molecular cloning techniques well known in the art. See, e.g., PCR Technology: Principles and Applications for DNA Amplification, ed. H A Erlich, Stockton Press, New York, N.Y. (1989); Sambrook et al., 2001, Molecular Cloning—A Laboratory Manual, $3^{rd}$ edition, Cold Spring Harbor Laboratory, Cold Spring Harbor, N.Y.; PCR Technology: Principles and Applications for DNA Amplification, ed. HA Erlich, Stockton Press, New York, N.Y. (1989).

Each element of the excisable nucleic acid construct is discussed in detail below.

5.2.1. Homing Endonuclease Recognition Sites

The excisable nucleic acid construct comprises at least a first homing endonuclease recognition site (ES1), and optionally a second homing endonuclease recognition site (ES2). In some embodiments where the excisable nucleic acid construct comprises only a first homing endonuclease recognition site, ES1 can be positioned 3' of the first tandem repeat (DR1) and 5' of the target DNA segment (D), or 3' of the target DNA segment (D) and 5' of the second tandem repeat (DR2). In some embodiments where the excisable nucleic acid construct comprises a first and a second homing endonuclease recognition site, ES1 is positioned 3' of the first tandem repeat (DR1) and 5' of the target DNA segment (D), and ES2 is positioned 3' of the target DNA segment (D) and 5' of the second tandem repeat (DR2). In certain embodiments, ES1 is positioned within D.

Homing endonuclease recognition sites allow for a corresponding homing endonuclease to cleave the excisable nucleic acid construct at or adjacent to the homing endonuclease recognition site.

Homing endonuclease recognition sites range from 14-40 nucleotide base pairs in length. In some embodiments, each homing endonuclease recognition site consists of 14-40 nucleotides. In some embodiments, each homing endonuclease recognition site consists of 18-40 nucleotides. In some embodiments, each homing endonuclease recognition site consists of 20-40 nucleotides. In some embodiments, each homing endonuclease recognition site consists of 25-40 nucleotides. In some embodiments, each homing endonuclease recognition site consists of 30-40 nucleotides. In some embodiments, each homing endonuclease recognition site consists of 35-40 nucleotides. In some embodiments, each homing endonuclease recognition site consists of 14, 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, each homing endonuclease recognition site consists of 24 nucleotides.

In some embodiments, ES1 is positioned 3' of DR1 and 5' of D. In some embodiments, ES1 is positioned to the 3' end of DR1. In some embodiments, ES1 is positioned immediately adjacent to the 3' end of DR1. In some embodiments, ES1 is positioned downstream to the 3' end of DR1. In some embodiments ES1 is positioned to the 5' end of D. In some embodiments, ES1 is positioned immediately adjacent to the 5' end of D. In some embodiments, ES1 is positioned upstream to the 5' end of D.

In some embodiments, ES1 is positioned 3' of D and 5' of DR2. In some embodiments, ES1 is positioned to the 3' end of D. In some embodiments, ES1 is positioned immediately adjacent to the 3' end of D. In some embodiments, ES1 is positioned downstream to the 3' end of D. In some embodiments, ES1 is positioned to the 5' end of DR2. In some embodiments, ES1 is positioned immediately adjacent to the 5' end of DR2. In some embodiments, ES2 is positioned upstream to the 5' end of DR2.

In some embodiments, ES2, when present in combination with ES1, is positioned 3' of D and 5' of DR2. In some embodiments, ES2 is positioned to the 3' end of D. In some embodiments, ES2 is positioned immediately adjacent to the 3' end of D. In some embodiments, ES2 is positioned downstream to the 3' end of D. In some embodiments, ES2 is positioned to the 5' end of DR2. In some embodiments, ES2 is positioned immediately adjacent to the 5' end of DR2. In some embodiments, ES2 is positioned upstream to the 5' end of DR2.

In some embodiments, where ES1 and ES2 are both present, ES1 and ES2 are arranged in the opposite orientation with respect to one another. In some embodiments, where ES1 and ES2 are both present, ES1 and ES2 are arranged in the same orientation with respect to one another.

In some embodiments, ES1 and ES2 are recognition sites for any homing endonuclease known to those of skill in the art. Homing endonucleases of many types (but not those from group II introns) catalyze a staggered double strand break (DSB) with a 4 bp single-stranded 3' overhang. In some embodiments, at least one of ES1 and ES2 is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, each of ES1 and ES2 is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), I-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., *S. Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., *Dokl. Biochem.* 339: 145-147 (1994); Kaliman, *Nucleic Acids Res.* 18: 4277 (1990), F-CphI (see, Zeng et al., *Curr. Biol.* 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments, at least one of ES1 or ES2 is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. In certain embodiments, each of ES1 and ES2 is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI.

In particular embodiments of the compositions and methods provided herein, ES1 and ES2 are selected based on the absence of the homing endonuclease recognition site from the wild-type (unengineered) nuclear DNA of the host cell. For example, the recognition sites for I-SceI, PI-MtuII(pps1), PI-MgaI(pps1), and F-CphI are absent from wild-type (unengineered) *S. cerevisiae* nuclear DNA (see, e.g., *Curr Biol* 2009; 19:218-22; Proc Natl Acad Sci USA 1988; 85:6022-6; *J Biol Chem* 2002; 277:16257-64; *J Biol Chem* 2002; 277: 40352-61; and *Nucleic Acids Res* 2001; 29:4310-8), while the site for VDE aka PI-SceI is present in some strains and absent in others (see, e.g., *Nucleic Acids Res* 2001; 29:4215-23). Thus, in some embodiments of the compositions and methods provided herein, ES1 and ES2 are recognition sites for I-SceI, and the host cell is a *S. cerevisiae* cell. In some embodiments, the ES1 and ES2 are recognition sites for PI-MtuII(pps1), and the host cell is a *S. cerevisiae* cell. In some embodiments, the ES1 and ES2 are recognition sites for PI-MgaI(pps1), and the host cell is a *S. cerevisiae* cell. In some embodiments, the ES1 and ES2 are recognition sites for F-CphI, and the host cell is a *S. cerevisiae* cell.

In some embodiments, the selection of ES1 and ES2 is based on fulfillment of one or more of the following criteria: (1) the homing endonuclease recognition site is absent from the entirety of the wild-type (unengineered) genome of the host cell (i.e., including mitochondrial DNA); (2) in the absence of the expression of the corresponding homing endonuclease, the recognition site of the homing endonuclease is not cleaved; and (3) nuclear expression of the corresponding homing endonuclease, e.g., to induce excision of a genomically integrated target nucleic acid, is not detrimental to the host cell. In some embodiments, in addition to being absent from the wild-type (unengineered) nuclear DNA of the host cell, ES1 and ES2 fulfill one, two, or all three of the criteria listed above.

5.2.2. Tandem Repeats

The excisable nucleic acid construct comprises a first and a second tandem repeat. The first tandem repeat (DR1) is located 5' of the target DNA segment (D) and the second tandem repeat (DR2) is located 3' of the target DNA segment (D).

The first and second tandem repeats can mediate the recombination of the remainder of the excisable nucleic acid construct following cleavage by homing endonucleases. Tandem repeats positioned in the same direction with respect to each other (direct tandem repeats) can advantageously mediate intrachromosomal recombination within a host cell, via the single stranded annealing pathway. See, e.g., Ivanov et al., *Genetics* 142:693-704 (1996).

DR1 and DR2 can be any tandem repeats that can mediate recombination of the remainder of the excisable nucleic acid construct following cleavage by homing endonucleases. Properties of tandem repeats that may affect such recombination include but are not limited to: length, GC content, homology with the native sequence of the host cell genome, and the degree of sequence identity between the tandem repeats. The extent of sequence identity may be determined using any computer program and associated parameters, including those described herein, such as BLAST 2.2.2 or FASTA version 3.0t78, with the default parameters.

In some embodiments, DR1 is positioned to the 5' end of ES1. In some embodiments, DR1 is positioned immediately adjacent to the 5' end of ES1. In some embodiments, DR1 is positioned upstream to the 5' end of ES1.

In some embodiments, DR2 is positioned to the 3' end of ES1, or when both ES1 and ES2 are present, to the 3' end of ES2. In some embodiments, DR2 is positioned immediately adjacent to the 3' end of ES1, or when both ES1 and ES2 are present, to the 3' end of ES2. In some embodiments, DR2 is positioned downstream to the 3' end of ES1, or when both ES1 and ES2 are present, to the 3' end of ES2.

In some embodiments, each of DR1 and DR2 independently comprises at least 18 nucleotide base pairs. In some embodiments, each of DR1 and DR2 independently comprises 18 to 500 nucleotide base pairs. In some embodiments, each of the first and second tandem repeat nucleic acids independently consists of 18 to 500, 18 to 495, 18 to 490, 18 to 485, 18 to 480, 18 to 475, 18 to 470, 18 to 465, 18 to 460, 18 to 455, 18 to 450, 18 to 445, 18 to 440, 18 to 435, 18 to 430, 18 to 425, 18 to 420, 18 to 415, 18 to 410, 18 to 405, 18 to 400, 18 to 395, 18 to 390, 18 to 385, 18 to 380, 18 to 375, 18 to 370, 18 to 365, 18 to 360, 18 to 355, 18 to 350, 18 to 345, 18 to 340, 18 to 335, 18 to 330, 18 to 325, 18 to 320, 18 to 315, 18 to 310, 18 to 305, 18 to 300, 18 to 295, 18 to 290, 18 to 285, 18 to 280, 18 to 275, 18 to 270, 18 to 265, 18 to 260, 18 to 255, 18 to 250, 18 to 245, 18 to 240, 18 to 235, 18 to 230, 18 to 225, 18 to 220, 18 to 215, 18 to 210, 18 to 205, 18 to 200, 18 to 195, 18 to 190, 18 to 185, 18 to 180, 18 to 175, 18 to 170, 18 to 165, 18 to 160, 18 to 155, 18 to 150, 18 to 145, 18 to 140, 18 to 135, 18 to 130, 18 to 125, 18 to 120, 18 to 115, 18 to 110, 18 to 105, 18 to 100, 18 to 95, 18 to 90, 18 to 85, 18 to 80, 18 to 75, 18 to 70, 18 to 65, 18 to 60, 18 to 55, 18 to 50, 18 to 45, 18 to 40, 18 to 35, 18 to 30, 18 to 25, or 18 to 20 nucleotide base pairs. In some embodiments, each of DR1 and DR2 independently consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 nucleotide base pairs.

In some embodiments, each of DR1 and DR2 independently consists of 18 to 200 nucleotide base pairs. In some embodiments, each of DR1 and DR2 independently consists of 18 to 150 nucleotide base pairs. In some embodiments, each of DR1 and DR2 independently consists of 18 to 100 nucleotide base pairs. In some embodiments, each of DR1 and DR2 independently consists of 18 to 80 nucleotide base pairs.

In some embodiments, DR1 and DR2 share at least 25% nucleotide sequence identity. In some embodiments, DR1 and DR2 share at least 30% nucleotide sequence identity. In some embodiments, DR1 and DR2 share at least 35% nucleotide sequence identity. In some embodiments, DR1 and DR2 share at least 40% nucleotide sequence identity. In some embodiments, DR1 and DR2 share at least 45% nucleotide sequence identity. In some embodiments, DR1 and DR2 share at least 50% nucleotide sequence identity. In some embodiments, DR1 and DR2 share at least 60% nucleotide sequence identity. In some embodiments, DR1 and DR2 share at least 65% nucleotide sequence identity. In some embodiments, DR1 and DR2 share at least 70% nucleotide sequence identity. In some embodiments, DR1 and DR2 share at least 75% nucleotide sequence identity. In some embodiments, DR1 and DR2 share at least 80% nucleotide sequence identity. In some embodiments, DR1 and DR2 share at least 85% nucleotide sequence identity. In some embodiments, DR1 and DR2 share at least 90% nucleotide sequence identity. In some embodiments, DR1 and DR2 share at least 95% nucleotide sequence identity. In some embodiments, DR1 and DR2 share at least 99% nucleotide sequence identity. In some embodiments, DR1 and DR2 share 100% nucleotide sequence identity.

In preferred embodiments, DR1 and DR2 are positioned in the same orientation with respect to one another (i.e. they are direct tandem repeats).

5.2.3. Target DNA Segment

The excisable nucleic acid construct comprises a target DNA segment (D). In some embodiments, the target DNA segment (D) is positioned 3' of the first homing endonuclease recognition site (ES1). In some embodiments, where a second homing endonuclease recognition site (ES2) is present, the target DNA segment (D) is positioned 5' of ES2. In some embodiments, the target DNA segment (D) is positioned 3' of the first homing endonuclease recognition site (ES1) and 5' of the second tandem repeat (DR2). In some embodiments, the target DNA segment (D) is positioned 3' of the first tandem repeat (DR1) and 5' of the first homing endonuclease recognition site (ES1).

In some embodiments, the 5' end of D is positioned to the 3' end of ES1. In some embodiments, the 5' end of D is positioned immediately adjacent to the 3' end of ES1. In some embodiments, the 5' end of D is positioned downstream to the 3' end of ES1.

In some embodiments, the 5' end of D is positioned to the 3' end of DR1. In some embodiments, the 5' end of D is positioned immediately adjacent to the 3' end of DR1. In some embodiments, the 5' end of D is positioned downstream to the 3' end of DR1.

In some embodiments, when ES1 is present in combination with ES2, the 3' end of D is positioned to the 5' end of ES2. In some embodiments, when ES1 is present in combination with ES2, the 3' end of D is positioned immediately adjacent to the 5' end of ES2. In some embodiments, when ES1 is present in combination with ES2, the 3' end of D is positioned upstream to the 5' end of ES2.

In some embodiments, the 3' end of D is positioned to the 5' end of DR2. In some embodiments, the 3' end of D is positioned immediately adjacent to the 5' end of DR2. In some embodiments, the 3' end of D is positioned upstream to the 5' end of DR2.

The target DNA segment can be any target DNA segment deemed useful by one of skill in the art. For example, the target DNA segment may comprise a gene of interest that can be "knocked in" a host genome and subsequently "knocked out" by excision. In some embodiments, the target nucleic can comprise a selectable marker that may be used to select for the integration of the excisable nucleic acid construct into a host genome and that is subsequently removed from the host genome by excision.

Useful examples of a target DNA segment include but are not limited to: a protein-coding sequence, selectable marker, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, the DNA segment can be of natural origin. Alternatively, a target DNA segment can be completely of synthetic origin, produced in vitro. Furthermore, a target DNA segment can comprise any combination of isolated naturally occurring DNA molecules, or any combination of an isolated naturally occurring DNA molecule and a synthetic DNA molecule. For example, a target DNA segment may comprise a heterologous promoter operably linked to a protein coding sequence, a protein coding sequence linked to a poly-A tail, a protein coding sequence linked in-frame with a epitope tag coding sequence, and the like. The target DNA segment may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual,* 3d. ed., Cold Spring Harbor Laboratory Press, Cold Spring Harbor, N.Y. (2001); Glover, D. M. (ed.), *DNA Cloning: A Practical Approach,* 2d. ed., MRL Press, Ltd., Oxford, U.K. (1995).

In some embodiments, D comprises a promoter element operably linked to a nucleic acid encoding a homing endonuclease. For example, where the excisable nucleic acid construct comprises a first and second recognition site, e.g., for the homing endonuclease F-CphI, the target DNA segment can include a nucleic acid sequence encoding F-CphI, which nucleic acid sequence is operably linked to a promoter element. In particular embodiments, the promoter element which controls the expression of the nucleic acid encoding the homing endonuclease is an inducible promoter, e.g., a galactose inducible promoter of *Saccharomyces cerevisiae* (e.g., promoters of the GAL1, GAL7, and GAL10 genes), such that excision of the target DNA segment, including the sequence encoding the homing endonuclease, can be selectively excised, for example, after integration of the excisable nucleic acid construct into the host cell genome. In some embodiments, the homing endonuclease is selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, the homing endonuclease is selected from the group consisting of: I-CreI, I-MsoI, I-SceI, I-SceIV, H-DreI, I-HmuI, I-PpoI, I-DirI, I-NjaI, I-NanI, I-NitI, I-NgrI, I-TevI, I-TevII, I-TevIII, F-TevI, F-TevII, F-CphI, PI-MgaI, PI-MtuII, I-CsmI, I-PanI, I-CeuI, and PI-SceI. In particular embodiments, the homing endonuclease is I-SceI. In certain embodiments, the homing endonuclease is F-CphI.

In some embodiments, D encodes one or more selectable markers. In some embodiments, the selectable marker is an antibiotic resistance marker. Antibiotic resistance markers are common to plasmid vectors used for creating recombinant nucleic acid sequences. For instance, pBR and pUC-derived plasmids contain as a selectable marker the bacterial drug resistance marker AMP$^r$ or BLA gene (See, Sutcliffe, J. G., et al., *Proc. Natl. Acad. Sci. U.S.A.* 75:3737 (1978)). The BLA gene encodes the enzyme Tem-1, which functions as a beta-lactamase and is responsible for bacterial resistance to beta-lactam antibiotics, such as narrow-spectrum cephalosporins, cephamycins, and carbapenems (ertapenem), cefamandole, and cefoperazone, and all the anti-gram-negative-bacterium penicillins except temocillin.

Other useful selectable markers include but are not limited to: NAT1, PAT, AUR1-C, PDR4, SMR1, CAT, mouse dhfr, HPH, DSDA, KAN$^R$, and SH BLE genes. The NAT1 gene of *S. noursei* encodes nourseothricin N-acetyltransferase and confers resistance to nourseothricin. The PAT gene from *S. viridochromogenes* Tu94 encodes phosphinothricin N-acetyltransferase and confers resistance to bialophos. The AUR1-C gene from *S. cerevisiae* confers resistance to Auerobasidin A (AbA), an antifuncal antibiotic produced by Auerobasidium pullulans that is toxic to budding yeast *S. cerevisiae*. The PDR4 gene confers resistance to cerulenin. The SMR1 gene confers resistance to sulfometuron methyl. The CAT coding sequence from Tn9 transposon confers resistance to chloramphenicol. The mouse dhfr gene confers resistance to methotrexate. The HPH gene of *Klebsiella pneumonia* encodes hygromycin B phosphotransferase and confers resistance to Hygromycin B. The DSDA gene of *E. coli* encodes D-serine deaminase and allows yeast to grow on plates with D-serine as the sole nitrogen source. The KAN$^R$ gene of the Tn903 transposon encodes aminoglycoside phosphotransferase and confers resistance to G418. The SH BLE gene from *Streptoalloteichus hindustanus* encodes a Zeocin binding protein and confers resistance to Zeocin (bleomycin).

In other embodiments, the selectable marker comprises a yeast gene that permits for selection of transformed cells of a yeast host strain. In some embodiments, the selectable marker rescues an auxotrophy, for example a nutritional auxotrophy, in the host strain. In such embodiments, the host strain comprises a functional disruption in one or more genes of the amino acid biosynthetic pathways of the host that cause an auxotrophic phenotype, such as, for example, HIS3, LEU2, LYSJ, MET15, and TRP1, or a functional disruption in one or more genes of the nucleotide biosynthetic pathways of the host that cause an auxotrophic phenotype, such as, for example, ADE2 and URA3. In particular embodiments, the genetically modified yeast host strain comprises a functional disruption in the URA3 gene. The functional disruption in the host yeast that causes an auxotrophic phenotype can be a point mutation, a partial or complete gene deletion, or an addition or substitution of nucleotides. Functional disruptions within the amino acid or nucleotide biosynthetic pathways cause the host strains to become auxotrophic mutants which, in contrast to the prototrophic wild-type strains, are incapable of optimum growth in media without supplementation with one or more nutrients. The functionally disrupted biosynthesis genes in the host strain can then serve as auxotrophic gene markers which can later be rescued, for example, upon introducing one or more plasmids comprising a functional copy of the disrupted biosynthesis gene.

Utilization of the URA3, TRP1, and LYS2 yeast genes as selectable markers has a marked advantage because both positive and negative selections are possible. Positive selection is carried out by auxotrophic complementation of the URA3, TRP1, and LYS2 mutations whereas negative selection is based on the specific inhibitors 5-fluoro-orotic acid (FOA), 5-fluoroanthranilic acid, and a-aminoadipic acid (aAA), respectively, that prevent growth of the prototrophic strains but allow growth of the URA3, TRP1, and LYS2 mutants, respectively. The URA3 gene encodes orotidine-5' phosphate decarboxylase, an enzyme that is required for the biosynthesis of uracil. Ura3− (or ura5−) cells can be selected on media containing FOA, which kills all URA3+ cells but not ura3− cells because FOA appears to be converted to the toxic compound 5-fluorouracil by the action of decarboxylase. The negative selection on FOA media is highly discriminating, and usually less than $10^{-2}$ FOA-resistant colonies are Ura+. The FOA selection procedure can be used to produce ura3 markers in haploid strains by mutation, and, more importantly, for selecting those cells that do not have the URA3-containing plasmids. The TRP1 gene encodes a phosphoribosylanthranilate isomerase that catalyzes the third step in tryptophan biosynthesis. Counterselection using 5-fluoroanthranilic acid involves antimetabolism by the strains that lack enzymes required for the conversion of anthranilic acid to tryptophan and thus are resistant to 5-fluoroanthranilic acid. The LYS2 gene encodes an aminoadipate reductase, an enzyme that is required for the biosynthesis of lysine. Lys2- and lys5-mutants, but not normal strains, grow on a medium lacking the normal nitrogen source but containing lysine and aAA. Apparently, lys2 and lys5 mutations cause the accumulation of a toxic intermediate of lysine biosynthesis that is formed by high levels of aAA, but these mutants still can use aAA as a nitrogen source. Similar with the FOA selection procedure, LYS2-containing plasmids can be conveniently expelled from lys2 hosts.

In other embodiments, the selectable marker is a marker other than one which rescues an auxotophic mutation. For example, the yeast host cell strain can comprise mutations other than auxotrophic mutations, for example, mutations that are not lethal to the host and that also do not cause adverse effects on the intended use of the strain, e.g., industrial fermentation, so long as the mutations can be identified by a known selection method.

5.2.4. Genomic Integration Sequences

In some embodiments, the excisable nucleic acid construct comprises a first and second genomic integration sequence. The genomic integration sequences allow for the excisable nucleic acid constructs described herein to be integrated into the genome of the host cell, e.g., by host cell mediated homologous recombination. To integrate an excisable nucleic acid construct into the genome by homologous recombination, the excisable nucleic acid construct preferably comprises at one terminus a nucleic acid sequence comprising an upstream genomic integration sequence (IS1) and at the other terminus a nucleic acid sequence comprising a downstream genomic integration sequence (IS2), wherein each genomic integration sequence is of sufficient length and sequence identity to initiate homologous recombination by the host cell with its chromosome. In some embodiments, the first genomic integration sequence (IS1) is located 5' of the first tandem repeat (DR1) and the second genomic integration sequence (IS2) is located 3' of the second tandem repeat (DR2).

In certain embodiments, IS1 is positioned to the 5' of DR1. In some embodiments, IS1 is positioned immediately adjacent to the 5' of DR1. In some embodiments, IS1 is positioned upstream to the 5' of DR1.

In certain embodiments, IS2 is positioned to the 3' of DR2. In some embodiments, IS2 is positioned immediately adjacent to the 3' of DR2. In some embodiments, IS2 is positioned downstream to the 3' of DR2.

The first and second genomic integration sequences allow for the excisable nucleic acid construct to integrate via homologous recombination into a particular locus of a host cell genome, e.g., a yeast genome. Targeted integration of the excisable nucleic acid construct into a host cell genome may provide useful advantages. For example, the excisable nucleic acid construct may be integrated into a gene of interest in the host cell genome, thereby "knocking out" the gene of interest and rendering it non-functional (FIG. 2). Alternatively, targeted integration of the excisable nucleic acid construct may be useful in "knocking in" a gene of interest at a particular genomic locus or in "knocking in" regulatory elements near a gene of interest, for example, to activate or up-regulate the expression of a gene of interest.

Properties that may affect the integration of an excisable nucleic acid construct at a particular genomic locus include but are not limited to: the lengths of the genomic integration sequences, the overall length of the excisable nucleic acid construct, and the nucleotide sequence or location of the genomic integration locus. For instance, effective heteroduplex formation between one strand of a genomic integration sequence and one strand of a particular locus in a host cell genome may depend on the length of the genomic integration sequence. An effective range for the length of a genomic integration sequence is 50 to 5,000 nucleotides. For a discussion of effective lengths of homology between genomic integration sequences and genomic loci see Hasty et al., *Mol Cell Biol* 11:5586-91 (1991).

IS1 and IS2 can comprise any nucleotide sequence of sufficient length and sequence identity to a host cell genomic locus that allows for genomic integration of the excisable nucleic acid construct. In some embodiments, "sufficient sequence identity" refers to sequences with at least 70%, at least 75%, at least 80%, at least 85%, at least 90%, at least 95%, at least 99%, or 100%, identity to a host cell genomic locus over a length of at least 20 base pairs, at least 50 base pairs, at least 100 base pairs, at least 250 base pairs, at least 500 base pairs, or more than 500 base pairs. The extent of sequence identity may be determined using any computer program and associated parameters, including those described herein, such as BLAST 2.2.2 or FASTA version 3.0t78, with the default parameters.

In certain embodiments, each of IS1 and IS2 comprises nucleotide sequences of sufficient length and sequence identity to a prokaryotic genomic locus to allow the integration of the excisable nucleic acid construct into the prokaryotic genomic locus. In certain embodiments, each of IS1 and IS2 comprises nucleotide sequences of sufficient length and sequence identity to a eukaryotic genomic locus to allow the integration of the excisable nucleic acid construct into the eukaryotic genomic locus. In certain embodiments, each of IS1 and IS2 comprises nucleotide sequences of sufficient length and sequence identity to a yeast genomic locus to allow the integration of the excisable nucleic acid construct into the yeast genomic locus. In certain embodiments, each of IS1 and IS2 comprises nucleotide sequences of sufficient length and sequence identity to a *Saccharomyces cerevisiae* genomic locus to allow the integration of the excisable nucleic acid construct into the *Saccharomyces cerevisiae* genomic locus. Suitable *Saccharomyces cerevisiae* genomic loci for integration of an excisable nucleic acid construct include but are not limited to the NDT80, HO, GAL80, HTX3, GAL2 and GAL1-GAL10-GAL7 loci.

In certain embodiments, each of IS1 and IS2 independently consists of about 50 to 5,000 nucleotides. In certain embodiments, each of IS1 and IS2 independently comprises about 50 to 5,000 nucleotides. In certain embodiments, each of IS1 and IS2 independently consists of about 100 to 2,500 nucleotides. In certain embodiments, each of IS1 and IS2 independently consists of about 100 to 1,000 nucleotides. In certain embodiments, each of IS1 and IS2 independently consists of about 250 to 750 nucleotides. In certain embodiments, each of IS1 and IS2 independently consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of IS1 and IS2 independently consists of about 500 nucleotides.

An excisable nucleic acid construct comprising a first and a second genomic integration sequence can be made using any technique apparent to one of skill in the art. In certain embodiments, an excisable nucleic acid construct comprising a first and a second integration sequence is made using overlap extension PCR and molecular cloning techniques known in the art. See, e.g., U.S. Patent Application Publication No. 2010/0136633, U.S. Pat. No. 5,023,171 (splicing by overextension PCR); Sambrook et al., 2001, *Molecular Cloning—A Laboratory Manual*, 3$^{rd}$ edition, Cold Spring Harbor Laboratory, Cold Spring Harbor, N.Y.

5.3 Host Cells

In another aspect provided herein is a host cell comprising the excisable nucleic acid construct described above. In certain embodiments, the host cell comprises the excisable nucleic acid construct integrated into the host cell genome.

Suitable host cells include any cell in which an excision of a target DNA segment from a chromosomal or episomal locus is desired. In some embodiments, the host cell is a prokaryotic cell. In some embodiments, the host cell is a bacterial cell. In some embodiments, the host cell is an *Escherichia coli* cell. In some embodiments, the host cell is a eukaryotic cell. In some embodiments, the host cell is a mammalian cell. In some embodiments, the host cell is a Chinese hamster ovary (CHO) cell, a COS-7 cell, a mouse fibroblast cell, a mouse embryonal carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In some embodiments, the host cell is a yeast cell. In some embodiments, the host cell is a diploid yeast cell. In some embodiments, the host cell is a haploid yeast cell. Useful yeast host cells include yeast cells that have been deposited with microorganism depositories (e.g. IFO, ATCC, etc.) and belong to the genera *Aciculoconidium*, *Ambrosiozyma*, *Arthroascus*, *Arxiozyma*, *Ashbya*, *Babjevia*, *Bensingtonia*, *Botryoascus*, *Botryozyma*, *Brettanomyces*, *Bullera*, *Bulleromyces*, *Candida*, *Citeromyces*, *Clavispora*, *Cryptococcus*, *Cystofilobasidium*, *Debaryomyces*, *Dekkara*, *Dipodascopsis*, *Dipodascus*, *Eeniella*, *Endomycopsella*, *Eremascus*, *Eremothecium*, *Erythrobasidium*, *Fellomyces*, *Filobasidium*, *Galactomyces*, *Geotrichum*, *Guilliermondella*, *Hanseniaspora*, *Hansenula*, *Hasegawaea*, *Holtermannia*, *Hormoascus*, *Hyphopichia*, *Issatchenkia*, *Kloeckera*, *Kloeckeraspora*, *Kluyveromyces*, *Kondoa*, *Kuraishia*, *Kurtzmanomyces*, *Leucosporidium*, *Lipomyces*, *Lodderomyces*, *Malassezia*, *Metschnikowia*, *Mrakia*, *Myxozyma*, *Nadsonia*, *Nakazawaea*, *Nematospora*, *Ogataea*, *Oosporidium*, *Pachysolen*, *Phachytichospora*, *Phaffia*, *Pichia*, *Rhodosporidium*, *Rhodotorula*, *Saccharomyces*, *Saccharomycodes*, *Saccharomycopsis*, *Saitoella*, *Sakaguchia*, *Saturnospora*, *Schizoblastosporion*, *Schizosaccharomyces*, *Schwanniomyces*, *Sporidiobolus*, *Sporobolomyces*, *Sporopachydermia*, *Stephanoascus*, *Sterigmatomyces*, *Sterigmatosporidium*, *Symbiotaphrina*, *Sympodiomyces*, *Sympodiomycopsis*, *Torulaspora*, *Trichosporiella*, *Trichosporon*, *Trigonopsis*, *Tsuchiyaea*, *Udeniomyces*, *Waltomyces*, *Wickerhamia*, *Wickerhamiella*, *Williopsis*, *Yamadazyma*, *Yarrowia*, *Zygoascus*, *Zygosaccharomyces*, *Zygowilliopsis*, and *Zygozyma*, among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, a *Arxula adeninivorans* cell, or a *Hansenula polymorphs* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces* lactis) cell. In some embodiments, the yeast host cell is a cell belonging to the genus *Candida*, such as *Candida lipolytica*, *Candida guilliermondii*, *Candida krusei*, *Candida pseudotropicalis*, or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In certain embodiments, an excisable nucleic acid construct as described above may be introduced into a host cell using any conventional technique to introduce exogenous nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., C A; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol. Cell. Biol. 5:3376-3385 (1985). Exemplary techniques include but are not limited to, spheroplasting, electroporation, PEG 1000 mediated transformation, and lithium acetate or lithium chloride mediated transformation.

5.4 Homing Endonuclease Expression Vector

In another aspect provided herein is an expression vector encoding a homing endonuclease useful in excising a target DNA segment from the genome of a host cell comprising an excisable nucleic acid construct.

In certain embodiments, the expression vector encodes a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, the expression vector encodes a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-NgrI, I-TevI, I-TevII, I-TevIII, F-TevI, F-TevII, F-CphI, PI-MgaI, PI-MtuII, I-CsmI, I-PanI, I-CeuI, and PI-SceI. In particular embodiments, the expression vector encodes I-SceI. In certain embodiments, the expression vector encodes F-CphI.

The homing endonuclease expression vector is any expression vector that allows for the expression of a homing endonuclease within a host cell. Suitable expression vectors include but are not limited to those known for use in expressing genes in *Escherichia coli*, yeast, or mammalian cells. Examples of *Escherichia coli* expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2µ plasmids.

In certain embodiments, the homing endonuclease expression vector further comprises a selectable marker that allows for selection of host cells comprising the expression vector. In certain embodiments, the selectable marker is selected from the group consisting of: URA3, hygromycin B phosphotransferase, aminoglycoside phosphotransferase, zeocin resistance, and phosphinothricin N-acetyltransferase.

In certain embodiments, the expression vector further comprises a transcription termination sequence and a promoter operatively linked to the nucleotide sequence encoding the homing endonuclease. In some embodiments, the promoter is a constitutive promoter. In some embodiments, the promoter is an inducible promoter.

Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

In some embodiments, an additional nucleotide sequence comprising a nuclear localization sequence (NLS) is linked to the 5' of the nucleotide sequence encoding the homing endonuclease. The NLS can facilitate nuclear localization of larger homing endonucleases (>25 kD). In some embodiments, the nuclear localization sequence is an SV40 nuclear localization sequence. In some embodiments, the nuclear localization sequence is a yeast nuclear localization sequence.

A homing endonuclease expression vector can be made by any technique apparent to one skilled in the art. In certain embodiments, the vector is made using polymerase chain reaction (PCR) and molecular cloning techniques well known in the art. See, e.g., *PCR Technology: Principles and Applications for DNA Amplification*, ed. H A Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.

5.5 Methods of Excising a Target DNA Segment

In another aspect, provided herein are methods of excising one or more target DNA segments from the genome of a host cell comprising one or more excisable nucleic acid constructs as described above. In certain embodiments, the methods comprise contacting the excisable nucleic acid construct, e.g., a chromasomally integrated nucleic acid construct, with a homing endonuclease in a host cell such that the homing endonuclease cleaves at or adjacent to at least one homing endonuclease recognition site. In some embodiments, the homing endonuclease cleaves at or adjacent to each of the homing endonuclease recognition sites.

The excisable nucleic acid construct can be contacted with the homing endonuclease by any technique deemed suitable by one of skill in the art. In certain embodiments, a homing endonuclease is expressed within a host cell using a homing endonuclease expression vector. Any homing endonuclease expression vector may be used including the expression vectors described above. The homing endonuclease expression vector may comprise a selectable marker, e.g., a counter-selectable marker, that allows for selection of host cells that do not contain the expression vector subsequent to excision of the target DNA segment. The expression vector used may also be a transient vector that has no selectable marker, or is one that is not selected for. In particular embodiments, the progeny of a host cell comprising a transient vector loses the vector over time. In other embodiments, the excisable nucleic acid construct can be contacted with a purified form of the homing endonuclease.

In some embodiments, cleavage of each of ES1 and ES2 advantageously creates three nucleic acid fragments (FIGS. 3A and 3B): (1) a left arm of a genomic nucleic acid; (2) a nucleic acid fragment comprising the target DNA segment; and (3) a right arm of the genomic nucleic acid. In embodiments where the excisable nucleic acid construct comprises a single ES site (e.g., positioned 5' or 3' to the target nucleic acid), or alternatively, where the nucleic acid construct comprises ES1 and ES2, and the construct is contacted with a homing endonuclease which cleaves only one of ES1 and ES2, cleavage of the ES creates only two nucleic acid fragments. After cleavage, endogenous 5' to 3' exonucleases found in the host cell rapidly degrade one strand of each nucleic acid fragment, destroying the nucleic acid fragment comprising the target DNA segment and leaving long 3' tails on the left (4) and right (5) arms of the genomic nucleic acid (FIG. 3C) comprising DR1 and DR2 as complementary regions (FIG. 4A). The complementary regions form a heteroduplex (FIG. 4B, 6) and undergo recombination facilitated by host cell proteins. In some embodiments, the complementary regions advantageously undergo recombination via the single strand annealing pathway. The extreme 3' ends of the tails on the right (7) and left (8) arms are not complementary and thus hang out of the heteroduplex formed by the complementary portions. These extreme non-complementary 3' ends are advantageously cleaved by a flap nuclease. Finally, repair DNA synthesis and DNA ligase fill in the heteroduplex and seal nicks, creating an intact genomic nucleic acid with a precise excision of the target DNA segment (FIG. 4C). In embodiments in which DR1 and DR2 share 100% nucleotide sequence identity with one another, DR1 and DR2 advantageously recombine to create a genomic nucleic acid comprising a third tandem repeat that shares 100% nucleotide sequence identity with DR1 and DR2.

In another aspect, provided herein is a method of simultaneously excising at least two target nucleic acids from the genome of a host cell in which at least two excisable nucleic acid constructs have been genomically integrated. In some embodiments, the method comprises contacting the at least two excisable nucleic acid constructs with one or more homing endonucleases in the host cell such that one or more homing endonucleases cleave at or adjacent to at least one of the first or second homing endonuclease recognition sites of each excisable nucleic acid construct.

In some embodiments, the host cell comprises two or more excisable nucleic acid constructs wherein each excisable nucleic acid construct comprises unique ES sites, i.e., ES sites not shared among other excisable nucleic acid constructs within the host cell. In these embodiments, one or more homing endonucleases are provided in the host cell to effect the simultaneous excision of the more than one target DNA segments. In some embodiments, more than one homing endonuclease is provided in the host cell to effect the simultaneous excision of the more than one target DNA segments.

In other embodiments, each of the genomically integrated excisable nucleic acid constructs share at least one identical ES region, such that contact of each of the ES region of each excisable nucleic acid construct with a single homing endonuclease capable of cleaving the ES results in the simultaneous excision of the target DNA segment of each excisable nucleic acid construct. In some embodiments, the methods provided herein allow for the simulataneuous excision of at least 2, 3, 4, 5, 6, 7, 8, 9, 10 or more than 10 target nucleic acids from the genome of a host cell. In some embodiments, the simultaneous multiple excision is effected with a single homing endonuclease having specificity for a shared ES site within each of the integrated excisable nucleic acid constructs. In other embodiments, the simultaneous multiple excision is effected with a plurality of homing endonucleases, each having specificity for at least one ES site within an integrated excisable nucleic acid construct.

An advantage of the methods presented is that DR1 and DR2 of a particular excisable nucleic acid construct may comprise any tandem repeat that can mediate the recombination of the excisable nucleic acid construct upon cleavage. Therefore, multiple excisable nucleic acid constructs, each with unique tandem repeats, can be used within the same cell without concerns of genomic instabilities due to recombination of tandem repeats between different excisable nucleic acid constructs. Further, the methods can advantageously be used for removing selectable markers to enable their reuse in the same host cell or its progeny.

In other embodiments, the excision event can be used to promote, suppress, or alter the expression of an endogenous gene of interest in the host cell. For example, in some embodiments, the first genomic integration sequence comprises a nucleotide sequence that is homologous to a nucleotide sequence positioned 5' of the coding sequence of the endogenous gene of interest, and the second genomic integration sequence comprises a nucleotide sequence that is homologous to a nucleotide sequence positioned within the coding sequence of the endogenous gene of interest, and the target DNA segment comprises a nucleotide sequence encoding a promoter that can be induced or repressed, for example, by addition of an inducer or repressor, respectively, to the culture medium in which the host cell is cultivated. Upon integration of the integrating sequence at the target locus, the native promoter of the target gene is replaced with the inducible or repressible promoter from the target DNA segment, rendering production of the gene product of the gene of interest dependent on the presence of the inducing or repressing agent in the culture medium. Similarly, the target DNA segment of the excisable nucleic acid construct may comprise a nucleotide sequence encoding a repressor that can be induced or repressed by addition of an inducer or repressor, respectively. Such exogenous regulation of the expression of the gene of interest can be removed as desired by inducing an excision event as described herein, such that the regulatable promoter or repressor is excised from the host cell genome.

In other embodiments, integration of the excisable nucleic acid construct into the host cell genome can be used to disrupt the expression of an endogenous gene of interest, for example, by interrupting the operable linkage between the coding sequence of the endogenous gene of interest and its native promoter element. Where restoration of the expression of the endogenous gene is desired, an excision event in accordance with the methods described herein can be induced to operably re-link the native promoter element with the coding sequence of the endogenous gene of interest, that is, to bring the native promoter element back within operable proximity of the coding sequence for the endogenous gene of interest.

5.6 Kits

In another aspect, provided herein is a kit for the excision of a target DNA segment from the genome of a host cell. In some embodiments, the kit comprises: (a) an excisable nucleic acid construct comprising, in a 5' to 3' orientation: (i) a first tandem repeat (DR1), (ii) a first homing endonuclease recognition site (ES1), (iii) a target DNA segment (D), and (iv) a second tandem repeat (DR2); and (b) a vector comprising a homing endonuclease nucleic acid encoding a homing endonuclease capable of binding to and cleaving at or adjacent to at least one of the first or second homing endonuclease recognition sites. In some embodiments, the kit comprises: (a) an excisable nucleic acid construct comprising, in a 5' to 3' orientation: (i) a first tandem repeat (DR1), (ii) a target DNA segment (D), (iii) a first homing endonuclease recognition site (ES1), and (iv) a second tandem repeat (DR2); and (b) a vector comprising a homing endonuclease nucleic acid encoding a homing endonuclease capable of binding to and cleaving at or adjacent to at least one of the first or second homing endonuclease recognition sites. In some embodiments, the kit comprises: (a) an excisable nucleic acid construct comprising, in a 5' to 3' orientation: (i) a first tandem repeat nucleic acid (DR1), (ii) a first homing endonuclease recognition site (ES1), (iii) a target nucleic acid, (iv) a second homing endonuclease recognition site (ES2), and (v) a second tandem repeat nucleic acid (DR2); and (b) a vector comprising a homing endonuclease nucleic acid encoding a homing endonuclease capable of binding to and cleaving at or adjacent to at least one of the first or second homing endonuclease recognition sites.

In some embodiments, each of the first and second tandem repeat nucleic acids independently comprises at least 18 nucleotide base pairs. In some embodiments, each of DR1 and DR2 independently consists of 18 to 500 nucleotide base pairs. In some embodiments, each of the first and second tandem repeat nucleic acids independently consists of 18 to 500, 18 to 495, 18 to 490, 18 to 485, 18 to 480, 18 to 475, 18 to 470, 18 to 465, 18 to 460, 18 to 455, 18 to 450, 18 to 445, 18 to 440, 18 to 435, 18 to 430, 18 to 425, 18 to 420, 18 to 415, 18 to 410, 18 to 405, 18 to 400, 18 to 395, 18 to 390, 18 to 385, 18 to 380, 18 to 375, 18 to 370, 18 to 365, 18 to 360, 18 to 355, 18 to 350, 18 to 345, 18 to 340, 18 to 335, 18 to 330, 18 to 325, 18 to 320, 18 to 315, 18 to 310, 18 to 305, 18 to 300, 18 to 295, 18 to 290, 18 to 285, 18 to 280, 18 to 275, 18 to 270, 18 to 265, 18 to 260, 18 to 255, 18 to 250, 18 to 245, 18 to 240, 18 to 235, 18 to 230, 18 to 225, 18 to 220, 18 to 215, 18 to 210, 18 to 205, 18 to 200, 18 to 195, 18 to 190, 18 to 185, 18 to 180, 18 to 175, 18 to 170, 18 to 165, 18 to 160, 18 to 155, 18 to 150, 18 to 145, 18 to 140, 18 to 135, 18 to 130, 18 to 125, 18 to 120, 18 to 115, 18 to 110, 18 to 105, 18 to 100, 18 to 95, 18 to 90, 18 to 85, 18 to 80, 18 to 75, 18 to 70, 18 to 65, 18 to 60, 18 to 55, 18 to 50, 18 to 45, 18 to 40, 18 to 35, 18 to 30, 18 to 25, or 18 to 20 nucleotide base pairs. In some embodiments, each of DR1 and DR2 consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 nucleotide base pairs.

In some embodiments, the excisable nucleic acid construct further comprises a first genomic integration sequence linked 5' of the first tandem repeat nucleic acid and a second genomic integration sequence linked 3' of the second tandem repeat nucleic acid. In some embodiments, the kit provides first and second genomic integration sequences that are specific to the host cell for which integration of the excisable nucleic acide construct and subsequent excision of the target nucleic acid is desired. For example, for use in yeast, the kit provides, in some embodiments, a nucleic acid construct comprising first and second yeast-specific genomic integration sequences that share sufficient length and homology to initiate homologous recombination with a selected yeast genomic locus. In some embodiments, the kit provides a plurality of nucleic acid constructs, each comprising a unique pair of first and second genomic integration sequences targeted to a specific yeast genomic locus.

In a particular embodiment, the kit provided herein comprises: (a) an excisable nucleic acid construct comprising, in a 5' to 3' orientation: (i) a first tandem repeat nucleic acid of at least 18 nucleotide base pairs, (ii) a first I-SceI site, (iii) a target nucleic acid, (iv) a second I-SceI site, and (v) a second tandem repeat nucleic acid of at least 18 nucleotide base pairs; and (b) a vector comprising a nucleic acid encoding I-SceI. In some embodiments, the excisable nucleic acid construct further comprises a first integration site linked 5' of the first homing endonuclease recognition site and a second integration site linked 3' of the second tandem repeat nucleic acid.

In another particular embodiment, the kit provided herein comprises: (a) an excisable nucleic acid construct comprising, in a 5' to 3' orientation: (i) a first tandem repeat nucleic acid, (ii) a first F-CphI site, (iii) a target nucleic acid, (iv) a second F-CphI site, and (v) a second tandem repeat nucleic acid; and (b) a vector comprising a nucleic acid encoding F-CphI. In some embodiments, the excisable nucleic acid construct further comprises a first integration site linked 5' of the first homing endonuclease recognition site and a second integration site linked 3' of the second tandem repeat nucleic acid.

In certain embodiments, the kits provided herein further comprise one or more host cells suitable for transformation with the excisable nucleic acid constructs and/or the vectors described above.

In some embodiments, the kit further comprises instructions for use that describe the methods of excising a target DNA segment from the genome of a host cell disclosed herein. In some embodiments, the kit comprises an excisable nucleic acid construct comprising a target DNA segment, wherein the target DNA segment is selected from, e.g., a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, or degradation signal.

6. EXAMPLES

6.1 Example 1

Construction of xMarker Constructs

The compositions and methods described herein were implemented to prepare and characterize a series of excisable selectable markers for use in *S. cerevisiae*, described herein as "xMarkers." The first generation of markers utilized the I-SceI endonuclease and tested the parameters of the DNA construct shown in FIG. 1, which parameters include: (1) different lengths of the direct repeats flanking the endonuclease sites and (2) one vs. two endonuclease sites. The second generation of markers applied the results of the first generation tests toward broader application of the I-SceI endonuclease. The third generation xMarkers demonstrated the usefulness and extensibility to other endonucleases listed in Table 1 below.

TABLE 1

Recognition and cleavage sites for the endonucleases.

| Meganuclease | minimal site size (base pairs) | site size used (base pairs) | sequence of site used |
|---|---|---|---|
| I-SceI | 18 | 18 | TAGGGATAACAGGGTAAT (SEQ ID NO: 3) |
| VDE (PI-SceI) | 31 | 31 | TATGTCGGGTGCGGAGAAAG AGGTAATGAAA (SEQ ID NO: 4) |
| F-CphI | 20 | 24 | GATGCACGAGCGCAACGCTC ACAA (SEQ ID NO: 5) |
| PI-MgaI (ppsI) | 22 | 24 | GCGTAGCTGCCCAGTATGAGT CAG (SEQ ID NO: 6) |
| PI-MtuII (ppsI) | unknown | 40 | ACGTGCACTACGTAGAGGGTC GCACCGCACCGATCTACAA (SEQ ID NO: 7) |

With respect to the reagents used in the experiments described below, restriction enzymes were obtained from New England Biolabs and Fermentas. Phusion, a high-fidelity thermostable polymerase from Finnzymes, was used for construction of DNA used in cloning of plasmids or in yeast transformations for chromosomal integrations. A low-fidelity thermostable polymerase kit was used for PCR of genomic DNA from yeast colonies (Qiagen Taq PCR kit). Oligonucleotides were obtained from Integrated DNA Technologies (IDT). Other chemicals were obtained from Sigma, Fisher, and Zymo Research (e.g., standard molecular biology buffer components like Tris and EDTA and standard yeast reagents like lithium acetate and yeast nitrogen base). Competent *E. coli* cells used for DNA cloning were purchased from Invitrogen. DNA minipreps were performed with the miniprep kit from Qiagen. Molecular biology, yeast molecular genetics, and yeast cell culture techniques were performed according to standard protocols.

6.1.1. Construction of First Generation xMarkers

The initial series of xMarkers used URA3 as the selectable marker, and each member of the series differed in the number of I-SceI cleavage sites (1 or 2) and in the length of direct repeats (20, 40, 60, or 80 bp). URA3 is a counterselectable marker whose presence can be selected by growth on medium lacking uracil and whose absence can be selected by growth on medium containing 5-fluoroorotic acid. Direct repeat sequences were designed to consist of a 112 bp stretch of DNA, wherein each segment of 20 bp had a GC content of ~50%, and that stretches of 20, 40, 60, and 80 bp had little predicted secondary structure at temperatures above 30° C. The I-SceI cleavage sites all shared the same 18 bp sequence: 5'-TAGGGATAACAGGGTAAT-3' (SEQ ID NO: 3). Table 2 lists all tested first generation xMarkers with the number of cleavage sites and their orientation relative to each other, the length and sequence of the direct repeats (DR), and the sequence of the I-SceI cleavage site(s). For the xMarkers with two I-SceI sites, the sequence of elements was DR→/I-SceI site→/URA3/I-SceI site→/DR→. For the xMarker with one I-SceI site, the sequence of elements was DR→/I-SceI site→/URA3/DR→.

TABLE 2

List of characteristics of individual elements in first
generation I-SceI xMarkers, with order and orientation
of the elements as shown in FIG. 1

| name of URA3 xMarker | length of DR (bp) | I-SceI sites (#) | orientation of I-SceI sites to each other | DR (scar) sequence |
|---|---|---|---|---|
| 20mer-direct | 20 | 2 | direct | AAGATCCGATCGACCGAGAA (SEQ ID NO: 8) |
| 40mer-direct | 40 | 2 | direct | AAGATCCGATCGACCGAGAACTGAGA ACGGTGCAATGATC (SEQ ID NO: 9) |
| 60mer-direct (aka s0x-URA3) | 60 | 2 | direct | AAGATCCGATCGACCGAGAACTGAGA ACGGTGCAATGATC- AACATGATCTGCGACGAGCT (SEQ ID NO: 10) |
| 80mer-direct | 80 | 2 | direct | AAGATCCGATCGACCGAGAACTGAGA ACGGTGCAATGATC- AACATGATCTGCGACGAGCTTGAGGA TGCAAATGGCTGAC (SEQ ID NO: 11) |
| 60mer-single | 60 | 1 | solo | AAGATCCGATCGACCGAGAACTGAGA ACGGTGCAATGATCAACATGATCTGC GACGAGCT (SEQ ID NO: 12) |

Due to the repeated sites in the xMarkers, construction required that the left half and the right half be constructed separately before joining the two halves. The first generation xMarkers were created in three steps.

First, the sequences flanking the selectable marker on the left (5') and on the right (3') were constructed separately by annealing of phosphorylated oligonucleotides. The left and right double-stranded flanking sequences created by annealing were designed to have complementary, non-palindromic, 3' single-stranded overhangs of five bases (TAGAC on top and GTCTA on bottom). Table 3 lists the oligos used for each xMarker. For each annealing reaction, an equimolar mixture of oligonucleotides in DNA ligase buffer was heated to 95° C. in a heat block for 5 minutes and then the heat block was turned off and allowed to cool slowly to room temperature over the course of 1-2 hours.

TABLE 3

List of oligonucleotides mixed for annealing to
make left segments and right segments flanking
the marker in first generation I-SceI xMarkers.

| name of URA3 xMarker | oligos annealed for left segment | oligos annealed for right segment |
|---|---|---|
| 20mer-direct | KB411, KB412 | KB464, KB429 |
| 40mer-direct | KB415, KB416 | KB419, KB420 |
| 60mer-direct (aka s0x-URA3) | KB423, KB425, KB426, KB427, KB428 | KB419, KB423, KB424, KB429 |
| 80mer-direct | KB423, KB425, KBB427, KB431, KB432, KB433 | KB419, KB423, KB429, KB432, KB434 |
| 60mer-single | KB423, KB425, KB426, KB427, KB428 | KB421, KB423, KB424, KB430 |

Second, the corresponding left and right flanking DNAs from the annealing mixtures were mixed with the RYSE 12 entry vector for a 3-way ligation. The right end of the left repeat sequence was joined to the left end of the right repeat sequence by a sticky end ligation, and on the opposite ends the left and right repeat sequences were joined to the plasmid by blunt end ligations. The spacer between the I-SceI cleavage sites contained divergent SchI restriction sites, separated by an XbaI site. These plasmids were called xMarker entry vectors, because they did not yet have a marker, and they had only the flanking sequences to direct cleavage and repair.

Third, the URA3 selectable marker was ligated into the xMarker entry vectors. The URA3 marker was amplified by PCR from a plasmid (RaBit 12-O-M-555) to give a blunt-ended marker. For the directly repeated dual I-SceI site xMarkers, the URA3 PCR used oligonucleotides KB439 and KB440; for the single I-SceI site xMarker, the oligonucleotides were KB439 and KB441. The xMarker entry vectors were digested with SchI to give a blunt-ended linear plasmid. Then the two fragments were ligated together using ligase standard conditions. This generated the xMarker structure shown in FIG. 1. Individual isolates of ligated plasmids were recovered and the desired plasmids were identified by DNA sequencing of the insert in the plasmid.

6.1.2. Construction of Second Generation xMarkers

The second generation of xMarkers were all created with 60 bp direct repeats to aid DNA repair and with two I-SceI cleavage sites in direct repeat. Each xMarker had a unique 60 bp sequence, which was chosen to be a semi-random sequence, as indicated below in Table 4.

TABLE 4

List of 2nd generation I-SceI xMarkers and their 60 bp repeat sequences.

| name of xMarker | selection | sequence of 60 bp repeat |
|---|---|---|
| s1x_hphA | hygromycin B resistance (hph) | CGTTACGAAGCACACACTAGTTAGCGTCGAGACA CATAGCGACGCTAGAACTTGCGACTT (SEQ ID NO: 13) |
| s2x_hphA | hygromycin B resistance (hph) | GTACTGCCTAGTAGAAACGGATCTCCACGTACTA GAGTCCACCTGGTATCTATTAGCCCG (SEQ ID NO: 14) |
| s3x_kanA | kanamycin/G418 resistance (kan) | CGAGGATTAACGTGTAAGGCCCTAAGCTATGTAC CGCATCTCCTAAGAGAGTGTGACCCA (SEQ ID NO: 15) |
| s4x_kanA | kanamycin/G418 resistance (kan) | TTAATCAGCGCCCAGAGACTAGCACTGAATGATC AACGGGTAGTTCACACACTGCCAGAC (SEQ ID NO: 16) |
| s5x_natA | nourseothricin resistance (nat) | ATGGAATCACGGGGCTATTCCACTTGCTAATAAC GAGGCGCTTATCAACGGCGAGCACAT (SEQ ID NO: 17) |
| s6x_natA | nourseothricin resistance (nat) | AGTCAAAGCGCGATTCGCTAGGAATGAGAGCGA GAACGAACCGGAGTATATCACAATCGC (SEQ ID NO: 18) |
| s7x_URA3 | uracil prototropy (URA3) | ACTAGAGCGAAATGGAGAGGTACGTGATCCTACT AGAGCCCACGCTATCATACAGTTGGC (SEQ ID NO: 19) |
| s8x_URA3 | uracil prototropy (URA3) | GTACGTCCGTACTTATGCTGAGCGCTCCTACACG AAAAACTCACCGTGACTAGCATAACG (SEQ ID NO: 20) |

The 60 bp sequences were chosen to satisfy two criteria: (1) the first, second, and third 20 bp windows had a melting temperature of 60°±2° C. and (2) no sequence window 13 bp or longer that appeared in the 60 bp sequence was identical to any native sequence in the yeast genome. This set included four different selectable markers: URA3; hygromycin B phosphotransferase or hph; nourseothricin acetyltransferase or nat; and aminoglycoside phosphotransferase or kan. These three drug resistance genes from bacteria were all controlled by adjacent sequences corresponding to the promoter and terminator of the TEF1 gene from *Kluyveromyces lactis*, and the suffix "A" was appended to indicate this TEF1-derived regulatory control; the cassettes were then called hphA, natA, and kanA.

Due to the repeated sites in the xMarkers, construction required that the left half and the right half be constructed separately before joining the two halves. The second generation xMarkers were created in two steps, using a strategy different from the first generation. The 60 bp sequence and a 20 bp I-SceI cleavage site were introduced to the left and right of the marker by priming PCR amplification of the marker with long-tailed oligonucleotides listed in Table 5 below.

TABLE 5

List of primers used for PCR amplification of left and right portions of 2nd generation I-SceI xMarkers.

| name of xMarker | left portion primers | right portion primers | restriction enzyme | alternative left portion primers | alternative right portion primers | alternative restriction enzyme |
|---|---|---|---|---|---|---|
| s1x_hphA | KB469, KB467 | KB470, KB468 | NdeI | KB469, KB492 | KB470, KB491 | RsrII or BanI |
| s2x_hphA | KB471, KB467 | KB472, KB468 | NdeI | KB471, KB492 | KB472, KB491 | RsrII or BanI |
| s3x_kanA | KB475, KB473 | KB476, KB474 | PvuI | KB475, KB494 | KB476, KB493 | NciI or BstXI |
| s4x_kanA | KB477, KB473 | KB478, KB474 | PvuI | KB477, KB494 | KB478, KB493 | NciI or BstXI |
| s5x_natA | KB481, KB479 | KB482, KB480 | StyI | none | none | none |
| s6x_natA | KB483, KB479 | KB484, KB480 | StyI | none | none | none |
| s7x_URA3 | KB487, KB485 | KB488, KB486 | NcoI | KB487, KB496 | KB488, KB495 | BsiHKAI or AlwNI |
| s8x_URA3 | KB489, KB485 | KB490, KB486 | NcoI | KB489, KB496 | KB490, KB495 | BsiHKAI or AlwNI |

The oligonucleotides contained a priming region of 20-22 bp at the 3' end and a 5' tail of 80 bp containing the unique 60 bp sequence and the I-SceI site. Two slightly different I-SceI sites were used on the left and the right of the marker: on the left, version 1 (v1) was 5'-GCTAGGGATAACAGGGTAAT-3'(SEQ ID NO: 21) and on the right, version 2 (v2) was 5'-ACTAGGGATAACAGGTTTAT-3' (SEQ ID NO: 22). The second generation xMarkers all had a structure of elements summarized by DR (60 bp)→/I-SceI site (v1)→/marker/I-SceI site (v2)→/DR (60 bp)→.

The xMarker construction overview is as follows. First, the left portion of the marker and the right portion of the marker were amplified separately by PCR. The primers were designed so that a middle segment of the marker was included in both the left and right PCR products, and so that this overlap segment included a unique restriction site that left single-stranded complementary overhangs. Second, the two PCR products were digested separately with the chosen restriction enzyme, gel-purified, and added to a three-piece ligation mixture with the linearized RYSE 12 entry vector. Similar to the first generation ligation, the left and right portions annealed and ligated using sticky ends, while the outermost ends of the marker construct participated in a blunt-ended ligation with the recipient plasmid. A difference from the first generation method is that after the ligation, the product already contains the marker gene and construction is completed. Individual isolates of ligated plasmids were recovered and the desired plasmids were identified by DNA sequencing of the insert in the plasmid. These plasmids were new xMarker 12 RaBits that could be used for RYSE-based stitching of compound DNA constructs, just as previous 12 RaBits were used.

The xMarker details are described below. The unique restriction sites internal to the markers that were used initially for each marker are as follows: hphA, NdeI (RsrII or BanI); kanA, PvuI (NciI or BstXI); natA, StyI; and URA3, NcoI (BsiHKAI or AlwNI). The enzymes chosen later were used if the initial enzymes did not yield positive clones; their benefit is that the single-stranded overhangs are not palindromic, so that it is not likely to get a ligated plasmid with two left or two right portions. Amplification of the left portion of a marker was performed with a ~20 bp reverse primer that annealed to the top strand on the right of the indicated restriction site and with a primer to the left edge of the marker that included a 5' tail, such that the 5' oligonucleotide had a structure as follows: 60 bp sequence→/I-SceI site (v1)→/~20 bp forward primer. Amplification of the right portion of a marker was performed with a ~20 bp forward primer that annealed to the bottom strand on the left of the indicated restriction site and with a primer to the right edge of the marker that included a 5' tail, such that the 3' oligonucleotide had a structure like this: 60 bp sequence (reverse complement)→/I-SceI site (v2, reverse complement)→/~20 bp reverse primer. Table 4 contains a list of the primers used for amplification of the left and right portions of each xMarker. The templates used for PCR amplification of the markers were RaBit plasmids: 12-O-M-21 for hphA, 12-O-M-261 for kanA, 12-O-M-262 for natA, and 12-O-M-555 for URA3. The finished xMarker third generation plasmids were themselves 12 RaBits that could be used for RYSE-based stitching of compound DNA constructs, just as previous 12 RaBits were used.

6.1.3. Construction of I-SceI Expression Plasmids

The I-SceI gene was placed under control of the *S. cerevisiae* promoter for GAL1 and cloned into a set of CEN.ARS plasmids with various markers. The yeast-*E. coli* shuttle vectors with CEN.ARS sequences and LEU2 (pRS415 aka pAM63) and URA3 (pRS416 aka pAM63) markers were previously described (see, e.g., Gene 1992; 110:119-22; and Genetics 1989; 122:19-27). Derivatives of pRS416 were made by replacing the auxotrophic markers with the drug resistance markers kanA (pAM1110), natA (pAM1111), and hphA (pAM1112). Each of the vectors was digested at a unique blunt-ended restriction site within the polylinker/multiple cloning site, either EcoRV (drug resistance markers) or SmaI (URA3 and LEU2), and then treated with phosphatase. The linearized vectors were ligated to a tripartite stitched PCR product that had been treated with polynucleotide kinase (PNK) to phosphorylate the 5' ends. The PCR product was made by stitching together three pieces of DNA having overlapping ends using the oligonucleotide primers called RYSE4 and RYSE11: (1) the promoter from *S. cerevisiae* GAL1 with RYSE linkers 2 and 3, provided by a SapI-liberated insert from RaBit 23-O—P-39, (2) the I-SceI coding sequence with RYSE linkers 3 and 4, provided by a PCR product from a custom-synthesized gene used as template and primers 00177-JD-75AN and 00177-JD-75AO, and (3) the terminator from *S. cerevisiae* TDH with RYSE linkers 4 and 5, provided by a SapI-liberated insert from RaBit 45-0-T-64. Individual isolates of ligated plasmids were recovered and the desired plasmids were identified by DNA sequencing of the $P_{GAL1}$-I-SceI-$T_{TDH3}$ insert in the plasmid. The expression plasmids were called pAM1592 (URA3), pAM1593 (kanA), pAM1594 (natA), and pAM1595 (hphA). The $P_{GAL1}$ promoter is highly expressed when cells are grown in galactose and, in wild-type cells (GAL80+ GAL4), is not expressed when cells are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called GAL4$_{OC}$ (for Operator Constitutive).

As described above, expression of the endonuclease was placed under the control of a strong promoter that was inducibly expressed in some host strain genetic backgrounds (GAL80+) and constitutively expressed in others (gal80Δ+/−GAL4$_{OC}$). Many other inducible promoters or constitutive promoters are expected to work well. Even if the promoter is constitutive, the expression of endonuclease can readily be eliminated after a desired time period by losing the plasmid; about half of the cells lose these plasmids after 10 generations in non-selective media (see, e.g., Gene 1992; 110:119-22; and Genetics 1989; 122:19-27).

6.1.4. Construction of Third Generation xMarkers: Additional Endonucleases

The initial series of xMarkers for other endonucleases (other than I-SceI) used URA3 as the selectable marker. Each member of the series of xMarkers contained a recognition/cleavage site for a different endonuclease [VDE, F-CphI, PI-MgaI (pps 1), PI-MtuII (pps1)]. See Table 1 above for a description of the cleavage sites. All xURA3 markers contained two copies of the same 50 bp sequence in directly repeated orientation flanking the cleavage sites; this unique 50 bp sequence destined to be the scar after excision was called xM0. Table 6 below provides a description of the scar sequences.

TABLE 6

Scar sequences of 50 bp used for $3^{rd}$ generation xMarkers with endonucleases other than I-SceI

| Scar Sequence code | Enzyme | Marker | sequence |
|---|---|---|---|
| xM0 | F-CphI, PI-MgaI, PI-MgaII, VDE | URA3 | AAGATCCGATCGACCGAGAACTGAG AACGGTGCAATGATCAACATGATCT (SEQ ID NO: 23) |
| xM1 | F-CphI | NatR | CGTTACGAAGCACACACTAGTTAGC GTCGAGACACATAGCGACGCTAGAA (SEQ ID NO: 24) |
| xM2 | F-CphI | HygR | GTACTGCCTAGTAGAAACGGATCTC CACGTACTAGAGTCCACCTGGTATC (SEQ ID NO: 25) |
| xM3 | F-CphI | KanR | CGAGGATTAACGTGTAAGGCCCTAA GCTATGTACCGCATCTCCTAAGAGA (SEQ ID NO: 26) |

TABLE 6-continued

Scar sequences of 50 bp used for 3$^{rd}$ generation xMarkers with endonucleases other than I-SceI

| Scar Sequence code | Enzyme | Marker | sequence |
|---|---|---|---|
| xM4 | F-CphI | NatR | TTAATCAGCGCCCAGAGACTAGCAC TGAATGATCAACGGGTAGTTCACAC (SEQ ID NO: 27) |
| xM5 | F-CphI | TBD | GAATCACGGGGCTATTCCACTTGCT AATAACGAGGCGCTTATCAACGGCG (SEQ ID NO: 28) |
| xM6 | F-CphI | zeoR | GTCAAAGCGCGATTCGCTAGGAATG AGAGCGAGAACGAACCGGAGTATAT (SEQ ID NO: 29) |
| xM7 | F-CphI | TBD | ACTAGAGCGAAATGGAGAGGTACGT GATCCTACTAGAGCCCACGCTATCA (SEQ ID NO: 30) |
| xM8 | F-CphI | TBD | GTACGTCCGTACTTATGCTGAGCGC TCCTACACGAAAAACTCACCGTGAC (SEQ ID NO: 31) |
| xM9 | F-CphI | TBD | GCATTAAGTCGTAGCTAGCGGATTC TCTCTTCGTGCATCCTAGCAAATGG (SEQ ID NO: 32) |

The scar sequences were chosen to satisfy the following criteria: (1) GC content of ~50%, (2) the first and second sequence of 20 bp (within the 50 bp total) had a melting temperature of 60°±2° C., (3) minimal predicted secondary structure at temperatures above 30° C., and (4) no sequence window 13 bp or longer that appeared in the 50 bp sequence was identical to any native sequence in the yeast genome. The general sequence and orientation of elements in the xMarkers was as shown in FIG. 1: DR (50 bp)→, cleavage site→, URA3, cleavage site→, DR (50 bp)→.

Due to the repeated sites in the xMarkers, creation of the DNA molecules required that the left half and the right half be constructed separately before joining the two halves. Construction of the markers described here used the "2nd Generation" strategy described above in section 6.2.

First, the left portion of the marker and the right portion of the marker were amplified separately by PCR. Four oligonucleotides were designed for PCR amplification of each xMarker: two "outer" oligonucleotides for PCR annealed to the ends of the marker and two "inner" oligonucleotides annealed inside the marker gene. The outer oligonucleotides contained 20-22 bp of sequence at the 3' end that was complementary to the template and 74-90 bp of sequence at the 5' end that did not anneal to the template and served to introduce the cleavage and scar sequences. The outer oligonucleotides were phosphorylated with PNK prior to inclusion in a PCR reaction, to facilitate ligation in later steps. The inner oligonucleotides were designed so that a middle segment of the marker was included in both the left and right PCR products, and so that this overlap segment included a unique restriction site that could be used to generate single-stranded, complementary overhangs. When possible, it was advantageous to choose restriction enzymes that generated non-palindromic overhangs, to reduce the likelihood of ligation of two left portions (or two right portions) together.

Second, the two PCR products were digested separately with the chosen restriction enzyme and gel-purified. Third, the left and right segments, each having a sticky end and a blunt end, were added the linearized RYSE 12 entry vector plasmid for a three-piece ligation. The left and right portions annealed and ligated using sticky ends, while the outermost ends of the marker construct participated in a blunt-ended ligation with the recipient plasmid. Individual clones of ligated plasmids were recovered and the desired plasmids were identified by DNA sequencing. These plasmids were new xMarker 12 RaBits that could be used for RYSE-based stitching of compound DNA constructs, just as previous 12 RaBits were used.

After the first set of xURA3 markers was tested, the F-CphI endonuclease was chosen for further work. Additional xMarkers with different selectable markers were made for use with F-CphI. This set included six different selectable markers: URA3; hygromycin B phosphotransferase or hph; nourseothricin acetyltransferase or nat; aminoglycoside phosphotransferase or kan; zeocin resistance gene or ble; and phosphinothricin N-acetyltransferase or pat. These drug resistance genes from bacteria were all controlled by adjacent sequences corresponding to the promoter and terminator of the TEF1 gene from *Kluyveromyces lactis*, and the suffix "A" was appended to indicate this TEF1-derived regulatory control; the cassettes were then called hphA, natA, kanA, zeoA, and patA. Table 7 lists the restriction sites and the inner oligonucleotides for each marker; and Table 8 lists the outer oligonucleotides for each marker.

TABLE 7

Templates, restriction sites, and "inner" oligonucleotides used for construction of 3$^{rd}$ generation xMarkers

| Marker | Template for PCR | Internal restriction enzymes for 3-way ligations | reverse inner oligonucleotide (RIO) | forward inner oligonucleotide (FIO) |
|---|---|---|---|---|
| URA3 | RaBit 12-0-M-555 | BsiHKAI, PpuMI, BslI, or AlwNI | KB496-266-100 | KB495-266-100 |
| hphA | RaBit 12-0-M-21 | RsrII or BanI | KB492-266-100 | KB491-266-100 |
| kanA | RaBit 12-0-M-261 | BstXI | KB494-266-100 or TD_187 | KB493-266-100 or TD_186 |
| natA | RaBit 12-0-M-262 | StyI | KB479-266-81 | KB480-266-81 |
| zeoA | pAM1800 | BglI | TD_183 | TD_182 |
| patA | pAM1894 | TBD | TBD | TBD |

TABLE 8

"Outer" oligonucleotides used for construction of 3rd generation xMarkers

| Marker | scar | cleavage site | PCR template | forward outer oligo (FOO) | reverse outer oligo (ROO) |
|---|---|---|---|---|---|
| x0.URA.VDE | xM0 | VDE | RaBit 12-0-M-555 | KB518-266-135 | KB519-266-135 |
| x0.URA.PI-MgaI | xM0 | PI-MgaI | RaBit 12-0-M-555 | KB522-266-136 | KB523-266-136 |
| x0.URA.PI-MtuII | xM0 | PI-MtuII | RaBit 12-0-M-555 | KB524-266-136 | KB525-266-136 |
| x0.URA.F-Cph | xM0 | F-CphI | RaBit 12-0-M-555 | KB520-266-136 | KB521-266-136 |
| x1.natA.F-Cph | xM1 | F-CphI | RaBit 12-0-M-262 | MF51-312-97 | MF52-312-97 |
| x2.hphA.F-Cph | xM2 | F-CphI | RaBit 12-0-M-21 | MF53-312-98 | MF54-312-98 |
| x3.kanA.F-Cph | xM3 | F-CphI | RaBit 12-0-M-261 | TD_180 | TD_181 |
| x4.natA.F-Cph | xM4 | F-CphI | RaBit 12-0-M-262 | MF57-312-98 | MF58-312-98 |
| x6.zeoA.F-Cph | xM6 | F-CphI | pAM1800 | TD_176 | TD_177 |

6.1.5. Construction of Endonuclease Expression Plasmids

Table 9 below describes plasmids containing the endonuclease genes I-SceI, F-CphI, PI-MtuII (pps1), PI-MgaI (pps1) and VDE. The endonuclease genes were either chemically synthesized (I-SceI, F-CphI, PI-MtuII (pps1), PI-MgaI (pps1)) or amplified by PCR from *S. cerevisiae* genomic DNA (VDE).

Since three of the endonucleases (all but F-CphI and I-SceI) were too large (>25 kD; 353-456 amino acids) to freely travel through the nuclear pores from the intracellular site of synthesis (cytoplasm) to the site of action (nucleus), a DNA sequence was added to the 5' end of the coding sequence to append the SV40 nuclear localization sequence (NLS) to the amino-terminus of the protein. This NLS was described to be essential for the activity of VDE during mitotic (normal proliferative) growth in *S. cerevisiae*, since this native yeast enzyme naturally enters the nucleus only during meiosis. See, e.g., *Mol Cell Biol* 2003; 23:1726-36. The NLS was added to VDE using oligonucleotides with tails containing the coding sequence for the SV40 NLS; the NLS was added to PI-MtuII and PI-MgaI as part of the chemical syntheses of the entire genes. PCR-based "stitching" or "overlap extension" was used to fuse the endonuclease coding sequences, with or without NLS, with a promoter and a terminator. A first set of constructs was made with the *S. cerevisiae* promoter from ACS2 and the terminator from ADE6, without using the RYSE linkers. For this first set, the promoter-gene-terminator PCR stitching products were digested with SacI and XhoI, whose unique restriction sites had been introduced by tails on the oligonucleotides used for priming the PCR reactions of

TABLE 9

Plasmids containing endonuclease genes

| Plasmid | backbone | yeast marker | endonuclease | promoter | terminator |
|---|---|---|---|---|---|
| pAM1592 | pRS416 | URA3 | I-SceI | GAL1 | TDH3 |
| pAM1593 | pAM1110 | kanA | I-SceI | GAL1 | TDH3 |
| pAM1594 | pAM1111 | natA | I-SceI | GAL1 | TDH3 |
| pAM1595 | pAM1112 | hphA | I-SceI | GAL1 | TDH3 |
| pAM1677 | pAM1112 | hphA | VDE with N-terminal SV40 NLS | ACS2 | ADE6 |
| pAM1678 | pUC19 | none | PI-MgaI (pps1) with N-terminal SV40 NLS | none | none |
| pAM1679 | pUC19 | none | PI-MtuII (pps1) with N-terminal SV40 NLS | none | none |
| pAM1680 | pUC19 | none | F-CphI | none | none |
| pAM1749 | pAM1112 | hphA | F-CphI | ACS2 | ADE6 |
| pAM1750 | pAM1112 | hphA | PI-MgaI (pps1) with N-terminal SV40 NLS | ACS2 | ADE6 |
| pAM1751 | pAM1112 | hphA | PI-MtuII (pps1) with N-terminal SV40 NLS | ACS2 | ADE6 |
| pAM1799 | pAM1112 | hphA | F-CphI | GAL1 | TDH3 |
| pAM1800 | pAM1801/ pAM1799 | zeoA | F-CphI | GAL1 | TDH3 |
| pAM1862 | pAM64 = pRS416 | URA3 | F-CphI | GAL1 | TDH3 |
| pAM1863 | pAM1110 | kanA | F-CphI | GAL1 | TDH3 |
| pAM1864 | pAM1111 | natA | F-CphI | GAL1 | TDH3 |
| pAM1865 | pAM1112 | hphA | PI-MtuII (pps1) with N-terminal SV40 NLS | GAL1 | TDH3 |
| pAM1866 | pAM1112 | hphA | PI-MgaI (pps1) with N-terminal SV40 NLS | GAL1 | TDH3 |
| pAM1867 | pAM1112 | hphA | VDE with N-terminal SV40 NLS | GAL1 | TDH3 | the individual pieces; then the constructs were ligated into the recipient plasmid that had been digested with SacI and XhoI and treated with phosphatase. A second set used the *S. cerevisiae* promoter from GAL1 and the terminator from TDH3; this set used the RYSE linkers and RYSE RaBits for the promoter (23-0-P-39) and terminator (45-0-T-64). For this second set of plasmids, the promoter-gene-terminator constructs were stitched with the RYSE primers RYSE4 and RYSE11 that had been previously phosphorylated using polynucleotide kinase (PNK), so that the blunt-ended stitched product could be efficiently ligated into a CEN.ARS plasmid with a yeast marker that had been linearized with a restriction enzyme that created blunt ended double-strand breaks. Finally, individual isolates of ligated plasmids were recovered and the desired plasmids were identified by DNA sequencing of the "promoter-gene-terminator" insert in the plasmid. The details of the plasmid construction are described below.

otrophic markers with the drug resistance markers kanA (pAM 1110), natA (pAM1111), and hphA (pAM1112). For the second set of plasmids, pAM1112 was digested at a unique blunt-ended restriction site (EcoRV) within the polylinker/multiple cloning site, and then treated with phosphatase. The linearized vector was ligated to tripartite stitched PCR products that had been treated with polynucleotide kinase (PNK) to phosphorylate the 5' ends. For the first set of plasmids, the tripartite stitched PCR products and the pAM 1112 recipient plasmid were both digested with XhoI and SacI and then mixed for ligation.

The "promoter-gene-terminator" PCR products for endonuclease gene expression were made by stitching together three pieces of DNA having overlapping ends. The oligonucleotides and templates used to create the three pieces, and the oligonucleotides used for stitching together the three pieces are shown in Table 10.

TABLE 10

Pieces used PCR stitches of promoter-endonuclease-terminator

| identity | promoter piece: oligos and template OR RaBit | endonuclease piece: oligos and template | terminator piece: oligos and template OR RaBit | priming oligos for stitching | treatment of stitched product prior to ligation |
|---|---|---|---|---|---|
| $P_{ACS2}$-VDE-$T_{ADE6}$ | KB510, KB512, genomic DNA (KB512 tail encodes NLS; KB510 tail introduces SacI site) | KB513, KB515, genomic DNA (KB513 tail encodes NLS) | KB514, KB511, genomic DNA (KB511 tail introduces XhoI site) | KB510, KB511 | digest with XhoI and SacI |
| $P_{ACS2}$-F-Cph-$T_{ADE6}$ | KB510, KB540, genomic DNA (KB510 tail introduces SacI site) | KB539, KB542, pAM1680 | KB541, KB511, genomic DNA (KB511 tail introduces XhoI site) | KB510, KB511 | digest with XhoI and SacI |
| $P_{ACS2}$-PI-MgaI-$T_{ADE6}$ | KB510, KB528, genomic DNA (KB510 tail introduces SacI site) | KB527, KB530, pAM1678 | KB529, KB511, genomic DNA (KB511 tail introduces XhoI site) | KB510, KB511 | digest with XhoI and SacI |
| $P_{ACS2}$-PI-MtuII-$T_{ADE6}$ | KB510, KB534, genomic DNA (KB510 tail introduces SacI site) | KB533, KB536, pAM1679 | KB535, KB511, genomic DNA (KB511 tail introduces XhoI site) | KB510, KB511 | digest with XhoI and SacI |
| $P_{GAL1}$-VDE-$T_{TDH3}$ | 23-0-P-39 | round 1: KB590, KB594, pAM1677; round 2: KB589, KB594, round 1 product | 45-0-T-64 | PNK-treated RYSE4, RYSE11 | none |
| $P_{GAL1}$-F-Cph-$T_{TDH3}$ | 23-0-P-39 | KB591, KB595, pAM1680 | 45-0-T-64 | PNK-treated RYSE4, RYSE11 | none |
| $P_{GAL1}$-PI-MgaI-$T_{TDH3}$ | 23-0-P-39 | KB589, KB593, pAM1678 | 45-0-T-64 | PNK-treated RYSE4, RYSE11 | none |
| $P_{GAL1}$-PI-MtuII-$T_{TDH3}$ | 23-0-P-39 | KB589, KB592, pAM1679 | 45-0-T-64 | PNK-treated RYSE4, RYSE11 | none |

The recipient plasmids were all based on the "pRS" series of yeast-*E. coli* shuttle vectors with CEN.ARS sequences and yeast selectable markers, e.g., the URA3 marked version (pRS416 aka pAM64) was previously described (see, e.g., *Gene* 1992; 110:119-22; and *Genetics* 1989; 122:19-27). Derivatives of pRS416 were made by replacing the aux- 6.1.6. Construction of I-SceI Expression Plasmids The I-SceI gene was placed under control of the *S. cerevisiae* promoter for GAL1 and cloned into a set of CEN.ARS plasmids with various markers. The yeast-*E. coli* shuttle vectors with CEN.ARS sequences and LEU2 (pRS415 aka pAM63) and URA3 (pRS416 aka pAM63) markers were previously described (see, e.g., *Gene* 1992; 110:119-22; and

*Genetics* 1989; 122:19-27). Derivatives of pRS416 were made by replacing the auxotrophic markers with the drug resistance markers kanA (pAM1110), natA (pAM1111), and hphA (pAM1112). Each of the vectors was digested at a unique blunt-ended restriction site within the polylinker/multiple cloning site, either EcoRV (drug resistance markers) or SmaI (URA3 and LEU2), and then treated with phosphatase. The linearized vectors were ligated to a tripartite stitched PCR product that had been treated with polynucleotide kinase (PNK) to phosphorylate the 5' ends. The PCR product was made by stitching together three pieces of DNA having overlapping ends using the oligonucleotide primers called RYSE4 and RYSE11: (1) the promoter from *S. cerevisiae* GAL1 with RYSE linkers 2 and 3, provided by a SapI-liberated insert from RaBit 23-0-P-39, (2) the I-SceI coding sequence with RYSE linkers 3 and 4, provided by a PCR product from a custom-synthesized gene used as template and primers 00177-JD-75AN and 00177-JD-75A0, and (3) the terminator from *S. cerevisiae* TDH with RYSE linkers 4 and 5, provided by a SapI-liberated insert from RaBit 45-0-T-64. Individual isolates of ligated plasmids were recovered and the desired plasmids were identified by DNA sequencing of the $P_{GAL1}$-I-SceI-$T_{TDH3}$ insert in the plasmid. The expression plasmids were called pAM1592 (URA3), pAM1593 (kanA), pAM1594 (natA), and pAM1595 (hphA). The $P_{GAL1}$ promoter is highly expressed when cells are grown in galactose and, in wild-type cells (GAL80+ GAL4), is not expressed when cells are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called GAL4$_{OC}$ (for Operator Constitutive).

Expression of the endonuclease was placed under the control of a strong promoter that was inducibly expressed in some host strain genetic backgrounds (GAL80+) and constitutively expressed in others (gal80Δ+/−GAL4$_{OC}$). Many other inducible promoters or constitutive promoters are expected to work well. Even if the promoter is constitutive, the expression of endonuclease can readily be eliminated after a desired time period by losing the plasmid; about half of the cells lose these plasmids after 10 generations in non-selective media (see, e.g., *Gene* 1992; 110:119-22; and *Genetics* 1989; 122:19-27).

6.1.7. Construction of F-CphI Expression Plasmids

After the F-CphI expression plasmid with the hphA marker (pAM 1799) was made and tested, the $P_{GAL1}$-F-CphI-$T_{TDH3}$ cassette was subcloned into other CEN.ARS plasmids with different markers (pAM 1110, pAM 1111, pAM64) using the restriction enzymes XhoI and XbaI, each of which cleaved a unique site in the recipient plasmids and pAM1799. The plasmids were all cut with XhoI and XbaI, the plasmid vectors were treated with phosphatase, and the $P_{GAL1}$-F-CphI-$T_{TDH3}$ cassette was ligated with the other backbones. After ligation, the correct plasmid isolates were identified by restriction digestion.

The zeocin-resistance plasmid (pAM1800) was created by a method different from the others. Rather than stitch together the "promoter-gene-terminator" PCR product for $P_{GAL1}$-F-CphI-$T_{TDH3}$ and then ligate into a recipient plasmid with the zeocin resistance marker, the construction started with the F-CphI expression plasmid with the hphA marker (pAM1799) and exchanged the marker by exploiting yeast homologous recombination in vivo to substitute the zeocin resistance gene in place of the hygromycinB resistance gene. First, pAM1799 was linearized with NdeI, a restriction enzyme that cut a unique site in the hygromycin B resistance coding sequence. Second, the zeocin resistance gene was PCR-amplified from pAM1500 (or any Topo plasmid) using oligonucleotides with long tails (JU183 and JU184) that introduced sequence from the $P_{TEF}$ promoter and $T_{TEF}$ terminator that was homologous to the sequence in pAM1799 that controlled expression of the hph marker. Third, the two pieces of DNA were gel-purified and transformed into yeast for "gap repair" recombination that precisely replaced the hygromycin B resistance gene with the zeocin resistance gene. The correct plasmid was verified by DNA sequencing.

The $P_{GAL1}$ promoter is highly expressed when cells are grown in galactose and is not expressed when wild-type cells (with genotype GAL80 GAL4) are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called GAL4$_{OC}$ (for Operator Constitutive). The $P_{ACS2}$ promoter is moderately expressed in all carbon sources.

6.2 Example 2

Excision of Selectable Markers from Chromosomal DNA

This example demonstrates the utility of the xMarker constructs described in Example 1 in mediating excision of a selectable marker from the chromosomal DNA of a host cell. As described below, the construct is transformed into cells, cells are plated on media selective for the xMarker, and the correct integration is confirmed by colony PCR; such strains perform just like any other strain made with a standard marker and the xMarker is stably maintained. Third, when the excision of the xMarker is desired, the strain is transformed with a single-copy (CEN.ARS) plasmid containing its own marker and an expression construct for the homing endonuclease gene, as described in the sections below. After growing under conditions that select for the presence of the plasmid for several generations and induce expression of the homing endonuclease gene, the strain is tested for loss of the xMarker. Finally, the strain is grown under conditions that permit loss of the homing endonuclease expression plasmid and isolates are tested for loss of the plasmid. At the end of this process, the strain is ready for reuse of the xMarkers.

For this strategy, it is advantageous that the xMarker is stable for a period of time sufficient for selection and verification of the cells that correctly integrated the desired DNA construct. High stability is ensured by using cells that lack the endonuclease gene until it is introduced by a second transformation. However, an alternative approach utilizes a host strain with a stably integrated endonuclease gene under the control of an inducible promoter. In this alternative scheme, the xMarker would be stable until the strain was cultured under conditions that induced expression of the endonuclease from the regulated promoter. If promoters with the desired characteristics are available, this approach would save time and effort required for transformation of the endonuclease plasmid.

6.2.1. Initial Testing of xMarkers Using I-SceI:

To test this approach for precise excision of target DNA, the efficiency and fidelity of excision of selectable markers from chromosomal DNA were measured in *S. cerevisiae*. First, the xMarkers were placed between two stretches of >500 bp sequence corresponding to the regions upstream and downstream of a chosen gene (generically, GOI=gene of interest) to generate a knock-out construct. Second, yeast cells were transformed with this DNA construct to delete the gene of interest and replace its coding sequence with the xMarker, via homologous recombination involving a double crossover event. Third, mutants were transformed with an I-SceI expression plasmid; plasmid-bearing isolates were allowed time to express the endonuclease and undergo DNA cleavage and repair. Fourth, colonies that were unable to grow under marker-selective conditions were identified and counted. Fifth, the chromosomal DNA sequence of the deleted gene of interest (goiA) locus was determined to assess if the marker was excised and repaired cleanly as expected. The details of this series of steps are presented below for the first generation markers.

First, a knock-out construct with the structure GOI US/xMarker/GOI DS (GOI=gene of interest, US=upstream, DS=downstream) was stitched together using overlap extension PCR with three elements. I-SceI xMarkers were initially tested in the context of a ndt80Δ construct; NDT80 is a meiosis-specific gene that was chosen because its deletion in mitotically growing cells has no discernable phenotype. Each PCR reaction used as templates three RaBits liberated from their plasmid backbones by digestion with SapI: (1) NDT80 upstream (01-0-U-30), (2) an xMarker RaBit, and (3) NDT80 DS (29-0-D-23). The primers for PCR were RYSE0 and RYSE19. After PCR, the reaction mixture was loaded on an agarose gel and the desired full-length product was purified from the gel.

Second, yeast cells were transformed with gel-purified PCR products and plated on selective plates. Selective plates for the first generation xMarkers were CSM-Uracil; selective plates for the drug resistance markers were YPD+drug (hygromycin B, nourseothricin, or G418). All xMarker tests were performed in strains derived from the CEN.PK2 or S288c strain backgrounds. The initial test of the first generation xMarkers involved transformation of the PCR products into a strain (Y1625) whose relevant genotype was GAL80+ GAL4 gal1Δ; this genotype conferred wild-type inducible expression from $P_{GAL1}$, but inability to eat galactose so that this sugar was a "gratuitous inducer." Desired tranformants had the mutant genotype ndt80Δ::xURA3, with several versions of the xURA3 marker as listed in Table 2. Colonies that arose on the CSM-U plates were tested for the presence of the desired chromosomal locus by PCR amplification of genomic DNA from cells lysed by boiling ("colony PCR") using primer pairs that amplified across the novel DNA junctions created by recombination. Amplification of the new 5' junction with primers RYSE3 and AET0065-186-63-F-pNDT80 gave a product of 1024 bp; amplification of the new 3' junction with primers RYSE4 and AET0072-186-63-R-tNDT80 gave a product of 1024 bp. Two isolates for each xMarker variant were chosen for further analysis.

Third, isolates with the genotype ndt80Δ::xMarker were transformed with an I-SceI expression plasmid. For the first generation ndt80Δ::xURA3 strains, the natA-marked plasmid (pAM1594) was transformed using standard transformation conditions, the cells were allowed time to express the new marker gene during outgrowth in liquid YPD for 3-6 hrs, then plated on YPD+nourseothricin plates. Half of each transformation was plated on regular YPD (2% dextrose) and half was plated on YPDG (1% dextrose+1% galactose). Since the host strain genotype was GAL80+ GAL4 gal1Δ, the GAL1 promoter of the I-SceI gene was not induced on dextrose; on the mixed dextrose and galactose, the GAL1 promoter was expected to remain off while dextrose was high, but then to turn on as the dextrose was consumed and the galactose in the plates took effect.

Fourth, isolates that had excised the marker were identified. The xURA3 markers have the advantage of counterselection on 5-FOA plates, which permit growth only of cells lacking URA3. In contrast, isolates that have excised the other xMarkers must be identified by screening, e.g., replica plating from non-selective plates on which all isolates grow to selective plates on which the desired isolates fail to grow. The first generation xMarkers used URA3 to take advantage of counterselection. In accordance with expectation, when the plasmid-harboring transformants described above were streaked from the YPD plate onto 5-FOA, no colonies grew because I-SceI was not expressed on YPD. When plasmid-harboring transformants were streaked from the YPDG plate onto 5-FOA, many colonies grew. The YPDG plate includes galactose and induces expression of I-SceI. The 5-FOA plate selectes against cells harboring intact URA3. Based on the number of 5-FOA colonies growing from restreaks of the I-SceI transformants relative to a control ura3Δ strain, it is estimated that ≥30% of the cells had lost URA3 from between dual I-SceI sites; the frequency appeared lower for the xURA3 with a single I-SceI site. This suggested that without I-SceI expression the URA3 xMarker was rarely excised ($<10^{-6}$ of cells) and after I-SceI expression was induced the URA3 was frequently excised. Excision frequency was subsequently tested more directly.

Fifth, the chromosomal locus where the xMarker had been integrated was sequenced to assess the scar remaining after I-SceI cleavage and subsequent DNA double-strand break repair. Colonies demonstrated to have lost marker function were used for colony PCR with a primer pair that annealed upstream and downstream of the junction between the xMarker and the GOI targeting sequences, and then the PCR product was sequenced. In the case of ndt80Δ::xMarkers, the primers annealed 208 bp upstream (JU-197-168-125-NDT80US-F) and 234 bp downstream (JU-198-168-125-NDT80DS-R) of the junctions between the xMarker and the NDT80 sequences. The expected sizes of PCR products was 462-522 bp if URA3 was cleanly excised and 2072 bp if URA3 was completely intact. All 27 of the 5-FOA resistant colonies used for colony PCR gave a ~500 bp product expected for excision. Sequencing of these 27 PCR products showed in all cases the expected perfect scar depicted in FIG. 1 (see Table 11). As provided in Table 11, all 27 colonies tested showed xMarker integration followed by I-SceI expression and xMarker excision.

TABLE 11

Results showing fidelity of excision by sequencing of 1st generation I-SceI xMarker scars after marker excision

| name of URA3 xMarker | length of DR (bp) | I-SceI sites (#) | scars sent for sequencing (#) | perfect scars (%) |
|---|---|---|---|---|
| 20mer-direct | 20 | 2 | 8 | 100 |
| 40mer-direct | 40 | 2 | 4 | 100 |
| 60mer-direct (aka s0x-URA3) | 60 | 2 | 4 | 100 |
| 80mer-direct | 80 | 2 | 8 | 100 |
| 60mer-single | 60 | 1 | 3 | 100 |

The first and second generation xMarkers (Tables 2 and 4) were also tested in different S. cerevisiae strains in which the GAL1 promoter was constitutive (gal80Δ GAL4$_{OC}$). The ndt80Δ::xMarker constructs were stitched together and transformed into yeast as above. Transformation mixtures with xURA3 were directly plated onto CSM-U plates; those with drug resistance markers were first grown for 3-6 hrs in liquid YPD in a shaking incubator before plating on YPD+drug plates. Two transformants of each xMarker variant that were verified by colony PCR to have the ndt80Δ::xMarker integration were independently transformed with one of the I-SceI expression plasmids and plated on selective plates as described above.

Since $P_{GAL1}$-I-SceI expression was constitutive, the colonies on the plasmid transformation selective plates were expected to contain a mixed population of cells that maintained or excised the xMarker. Several colonies from each plate were restreaked on non-selective YPD plates that permitted growth of cells that had lost the plasmid or the marker or both. Colonies from these restreaks were patched on YPD plates, grown overnight, then replica plated to YPD+drug, CSM-uracil, and 5-FOA plates. Many patches grew on both 5-FOA and CSM-uracil, revealing a mixed population of cells in the patch and suggesting that further outgrowth under non-selective conditions prior to isolation of colonies was required to obtain a homogeneous population for analysis. Although the frequency of marker excision was generally underestimated in this experiment due to the mixed patches, generally at least 18% and more often 35-50% of the patches had at least some cells that had excised the marker (Table 12). Most of the patches (53-88%) had completely lost the I-SceI expression plasmid before replica plating. In parallel with the patching and replica plating, 90 colonies on the YPD restreak plates from two independent ndt80Δ::s1x-hphA strains were tested for marker excision by colony PCR; 48% (43/90) of the colonies yielded a band of the size expected for a precise excision of the hphA marker.

TABLE 12

Results showing frequency of excision of $2^{nd}$ generation I-SceI xMarkers and frequency of loss of the endonuclease expression plasmid

| | | % of patches with at least some cells with | | | |
|---|---|---|---|---|---|
| xMarker | plasmid marker | intact xMarker | excised xMarker | retained plasmid | lost plasmid |
| s1x-hphA | URA3 | 65 | n/a | 28 | 100 |
| s5x-natA | URA3 | 98 | n/a | 48 | 100 |
| s7x-URA3 | hphA | 58 | 46 | 13 | n/a |
| s8x-URA3 | hphA | 79 | 40 | 19 | n/a |
| 20mer-URA3 | hphA | 92 | 19 | 15 | n/a |
| 60mer-URA3 (aka s0x-URA3) | hphA | 35 | 75 | 15 | n/a |
| 80mer-direct | hphA | 48 | 58 | 33 | n/a |

Additional xMarkers have been constructed for investigations using experiments similar to those described above. In addition, tests of simultaneous excision of multiple xMarkers integrated at different loci in the same strain have been successful and have shown no signs of genomic instability (e.g., chromosomal translocations) (see Example 6.2.4 below).

6.2.2. Testing of xMarkers Using Other Endonucleases:

Four additional endonucleases were tested using a set of xURA3 markers shown in Table 6. Each xMarker contained the URA3 selectable marker gene flanked by two endonuclease cleavage sites, which in turn were flanked by a directly repeated sequence of 50 base pairs. For each, a knock-out construct with the structure GOI US/xMarker/GOI DS (GOI=gene of interest, US=upstream, DS=downstream) was stitched together using overlap extension PCR with three elements. The new-endonuclease URA3 xMarkers were initially tested with HXT3 as the gene of interest (GOI). Each PCR reaction used as templates three RaBits liberated from their plasmid backbones by digestion with SapI: (1) HXT3 upstream (01-0-U-407), (2) an xMarker RaBit (x0.URA.VDE, x0.URA.F-CphI, 12-0-x0.URA.PI-MtuII, 12-0-x0.URA.PI-MgaI), and (3) HXT3 DS (29-0-D-408). The primers used for PCR stitching were RYSE0 and RYSE19. After PCR, the reaction mixture was loaded on an agarose gel and the desired full-length product was purified from the gel. Yeast cells were transformed with gel-purified PCR products and plated on selective plates for URA3 (CSM-Uracil). Desired transformants had the mutant genotype hxt3Δ::xURA3, with several versions of the xURA3 marker as listed in Table 6. Colonies that arose on the CSM-Uracil plates were tested for the presence of the desired chromosomal locus by PCR amplification of genomic DNA from cells lysed by boiling ("colony PCR") using primer pairs that amplified across the novel DNA junctions created by recombination. The primers were KB502, KB503, and CPK904; the latter two produced a 738 bp fragment for hxt3Δ::xURA3 and the former two produced a 538 bp fragment for intact HXT3. Two isolates for each xMarker variant were chosen for further analysis.

The xURA3 markers have the advantage of counterselection on 5-FOA plates, which permit growth only of cells lacking URA3. In contrast, isolates that have excised other xMarkers must be identified by screening, e.g., replica plating from non-selective plates on which all isolates grow to selective plates on which the desired isolates fail to grow. The first generation xMarkers used URA3 to take advantage of counterselection, which permitted quantification of rare excision events. In accordance with expectation, when the strains containing xURA3 markers and lacking the endonuclease expression plasmids were plated or streaked onto 5-FOA, no colonies grew. This indicated that spontaneous excision of the xMarker was very rare in the absence of endonuclease-catalyzed cleavage. This suggested that without endonuclease expression the URA3 xMarker was rarely excised ($<10^{-6}$ of cells).

Isolates with the confirmed genotype hxt3Δ::xURA3 were transformed with the cognate expression plasmids for endonucleases that were marked with the marker gene hphA (pAM1799, pAM1865, pAM1866). Cells from transformation mixtures were allowed time to express the new marker gene (hphA) during outgrowth in liquid YPD for 3-6 hrs, then plated on YPD+hygromycinB plates. Since the host strain genotype was gal80Δ GAL4oc, the GAL1 promoter driving endonuclease gene expression was constitutively expressed and did not need an inducer. After three days growth, the transformant colonies were restreaked on YPD+hygromycinB plates and grown another three days. Colonies from the restreaks (four colonies per endonuclease) were resuspended in 3 ml of YPD and grown overnight in nonselective conditions to permit loss of the plasmids. Cell density was determined, cultures were diluted, and cells were plated at an estimated density of 150, 15,000, or 150,000 cells per plate on three different solid media: YPD, YPD+hygromycinB, and 5-FOA. All cells were expected to form colonies on YPD, only cells that had maintained the endonuclease expression plasmid were expected to form colonies on hygromycin B, and only cells that had excised the xURA3 marker were expected for form colonies on 5-FOA.

The results shown in Table 13 indicate that F-CphI mediated high efficiency xMarker excision, PI-MtuII mediated low efficiency xMarker excision, and PI-MgaI mediated undetectable levels of xMarker excision. The loss of the CEN.ARS endonuclease expression plasmids was a high frequency event, suggesting that it would be easy to isolate cells that had lost the endonuclease prior to another round of transformations with new xMarkers.

TABLE 13

Results comparing xMarker excision efficiency of different endonucleases and frequency of loss of expression plasmid after several generations of non-selective growth

| Endonuclease | % of cells that lost xURA3 xMarker | % of cells that lost hphA-marked endonuclease expression plasmid |
|---|---|---|
| F-CphI | 90.8% | 31.9% |
| PI-MgaI | 0.058% | 76.5% |
| PI-MtuII | <0.0007% | ND |
| VDE | ND | ND |

To determine if the F-CphI mediated excision of the marker left behind a "perfect" scar, the 5-FOA resistant (functionally ura3⁻) colonies were subjected to colony PCR using oligonucleotide primers that flanked the integration site of the xURA3 marker (oligonucleotides KB503 and KB604); the 533 bp PCR product was sent for DNA sequencing with oligonucleotide primer KB503. Of 16 colonies tested, all had a "perfect" scar in which the only DNA sequence remaining from the xMarker was a single copy of the 50 bp sequence.

6.2.3 Further Tests of F-CphI xMarker Excision Frequency and Fidelity

Additional xMarkers with F-CphI cleavage sites and various selectable markers were created and tested (natA, kanA, hphA, zeoA). The excision frequencies and fidelities of excision of these markers were tested in haploid and diploid S. cerevisiae strains, both singly and in combinations. The frequency of excision was often 100% of the colonies tested and always >80%. The fidelity of excision was nearly 100%. Almost all of the excision events in many independent cultures gave the expected scar; excision left behind only one copy of the 50 by unique sequence that was introduced as a direct repeat in the xMarker and the marker itself was absent (Table 14).

Strains with xMarkers at the NDT80 locus (deleting the NDT80 gene) were made as follows. The stitched PCR product used to transform cells was made by stitching the xMarker (as a 12 RaBit) with the 01-0-U-97 and 29-0-U-23 RaBits with the oligonucleotides called RYSE0 and RYSE19. After transformation, the identity of the correct isolates was verified by colony PCR using a pair of oligonucleotide primers in which one was outside of the transformed DNA (CPK650) and the other was inside the marker (e.g., KB561 and KB562 for URA3; KB563 and KB564 for natA, kanA, and hygA), which gave a PCR product of ~1.1 kb. The removal of native NDT80 sequence was verified by the absence of a PCR product from colony PCR with oligonucleotides AET83 and AET84, which gave a PCR product of 442 bp from the parental strain with an intact NDT80 locus. After transformation with a F-CphI expression plasmid (pAM1800), individual colonies were tested for the intended excision by colony PCR with JU197 and JU198, which gave a band of 492 bp for a perfect excision that left behind only one copy of the 50 bp scar sequence; this band was run on a gel to visualize and separate from any other DNA, then extracted from the gel and sent for DNA sequencing using the same oligonucleotides used to prime the PCR reaction.

Strains with xMarkers at the GAL80 locus (deleting the GAL80 gene) were made as follows. The stitched PCR product used to transform cells was made by stitching the xMarker (as a 12 RaBit) with the 01-0-U-270 and 29-0-U-95 RaBits with the oligonucleotides called RYSE0 and RYSE19. After transformation, the identity of the correct isolates was verified by colony PCR. Oligonucleotides JU436 and RYSE3 amplified the vicinity around the 5' junction where the transformed DNA integrated within the GAL80 upstream sequence to give a PCR product of 572 bp (alternatively, JU210 and RYSE3 were used to give a PCR product of 182 bp); JU221 and RYSE4 gave a 386 bp product from amplification of the 3' junction of the marker with the GAL80 down-

TABLE 14 xMarker excision frequencies for different endonucleases and DRs of at least 50 bp length

| | | | | | xMarker Excision | | | Excision Precision | |
|---|---|---|---|---|---|---|---|---|---|
| Endo-nuclease | Length of DR (bp) | Num. of ES's | xMarker Targeting Construct | Endo-nuclease Expression Plasmid | Num. of Cells Tested [a] | Num. of Cells with Excised xMarker | Excision Frequency | Num. of Cells Tested | Num. of Cells with Perfect Scar [b] |
| F-CphI | 50 | 2 | HXT3-US_xM0.URA.F-CphI_HXT3-DS | pAM1799 | 402 | 365 | 0.91 | ND | ND |
| | 50 | 2 | GAL80-US_xM0.URA.F-CphI_GAL80-DS | pAM1800 | 8 | 8 | 1 | 8 | 8 |
| | 50 | 2 | GAL80-US_xM1.nat.F-CphI_GAL80-DS | pAM1800 | 16 | 16 | 1 | 8 | 8 |
| | 50 | 2 | GAL80-US_xM3.kan.F-CphI_GAL80-DS | pAM1800 | 8 | 8 | 1 | 8 | 8 |
| | 50 | 2 | GAL80-US_xM4.nat.F-CphI_GAL80-DS | pAM1800 | 8 | 8 | 1 | 8 | 8 |
| | 50 | 2 | GAL80-US_xM6.zeo.F-CphI_GAL80-DS | pAM1862/ pAM1864 | 16 | 16 | 1 | 16 | 16 |
| PI-MgaI | 50 | 2 | HXT3-US_xM0.URA.PI-MgaI_HXT3-DS | pAM1866 | ~6.6 × 10$^5$ | 0 | <1.5 × 10$^{-6}$ | ND | ND |
| PI-MtuII | 50 | 2 | HXT3-US_xM0.URA.PI-MtuII_HXT3-DS | pAM1865 | ~6.6 × 10$^5$ | 419 | 6.3 × 10$^{-4}$ | ND | ND |
| VDE | 50 | 2 | HXT3-US_xM0.URA.VDE_HXT3-DS | pAM1677 | 535 | 9 | 1.7 × 10$^{-2}$ | ND | ND |
| I-SceI | 60 | 2 | NDT80-US_s60M.URA.I-SceI_NDT80-DS | pAM1595 | 288 | 155 | 0.54 | 4 | 4 |
| | 80 | 2 | NDT80-US_s80M.URA.I-SceI_NDT80-DS | pAM1595 | 237 | 76 | 0.32 | 8 | 8 |

[a] Number of colonies on YPD plates, adjusted by dilution factor.
[b] Perfect scar = after excision only DNA sequence remaining from the xMarker is a single copy of the DR sequence.
ND = not determined.

stream sequence by (alternatively, JU439 and RYSE4 were used to give a PCR product of 531 bp); a negative control was colony PCR with primers JU212 and JU210, which gave a 290 bp product for an intact GAL80 locus and no product for the desired locus. After transformation with a F-CphI expression plasmid (pAM1800 or pAM1799), individual colonies were tested for the intended excision by colony PCR with JU210 and JU211, which gave a band of 277 bp for a perfect excision that left behind only one copy of the 50 bp scar sequence; this band was run on a gel to visualize and separate from any other DNA, then extracted and sequenced using the same oligonucleotides used to prime the PCR reaction.

After transformation with an expression plasmid for F-CphI, eight of the colonies that arose on selective plates were randomly selected for colony PCR to diagnose excision. For the following xMarkers all eight colonies gave the expected PCR product and the DNA sequencing verified perfect scars: x0URA3, x1nat, x3kan, x4nat, and x6zeo. The x2hph marker gave anomalous results; sequencing of the scars and resequencing xMarker (the 12 RaBit) revealed that the direct repeats were not as intended, and instead only 19 bp were directly repeated flanking the marker with a scrambling of the adjacent sequences. Despite the small region provided for repair of the double-stranded break the excision frequency and fidelity was good; in the first trial, six out of eight colonies had clearly excised the marker and left behind scars of variable lengths; in the second trial, eight of eight colonies had excised the marker and left behind scars of 19 bp. This suggests that 17-18 bp would be sufficient for the direct repeat length, and 50 bp is more than enough to guide repair of the chromosome after cleavage by F-CphI.

High frequency and precision of excision of the xMarkers was observed in several circumstances. The simplest circumstance was a single xMarker in each strain. A more complicated circumstance was excision of an xMarker in a heterozygous diploid strain that had one intact GAL80 allele and one allele that had been deleted by an xMarker; in this case, the intact GAL80 locus remained intact after the excision of the xMarker at the disrupted allele. This is important, because it might have happened that the cleaved chromosome ends near the xMarker, after action of the F-CphI, could have used the intact second copy of the chromosome as a template for repair, thereby leading to a gene conversion event that would restore the intact GAL80 locus to the chromosome from which it had been deleted. This gene conversion event was not seen, and instead the cell apparently preferentially repaired the broken chromosome by an intrachromosomal single-stranded annealing mechanism.

6.2.4. Simultaneous Multiple xMarker Excision

This example demonstrates the utility of the xMarker constructs in mediating simultaneous excision of multiple selectable markers from the chromosomal DNA of a host cell, where each xMarker was used to mark an integration into a unique locus.

Strains with xMarkers at both the GAL80 and GAL4 loci were made as follows. Hygromycin sensitive cells were transformed with the xMarker Targeting construct GAL80-US_xM4.Hph.FCphI_GAL80-DS. Transformation was outgrown in 3 mL liquid YPD medium for 5 hrs and then plated on YPD plus hygromycin. Transformants were verified by colony PCR. Oligonucleotides HJ53 and HJ848 amplified the vicinity around the 5' junction where the transformed DNA integrated within the GAL80 upstream sequence to give a PCR product of 761 bp (alternatively, HJ53 and HJ253 were used to give a PCR product of 1 kb); H727 and HJ258 gave a 1033 bp product from amplification of the 3' junction of the marker with the GAL80 downstream sequence by (alternatively, HJ727 and HJ54 were used to give a PCR product of 627 bp). A chosen isolate was then transformed with the xMarker Targeting construct GAL4-US_xM0.Kan.FCphI_GAL4-DS. Transformation was outgrown in 3 mL liquid YPD medium for 5 hrs and then plated on YPD plus G418. Transformants were verified by colony PCR. Oligonucleotides HJ270 and HJ253 amplified the vicinity around the 5' junction where the transformed DNA integrated within the GAL4 upstream sequence to give a PCR product of 1.1 kb (alternatively, HJ270 and HJ54 were used to give a PCR product of 774 bp); H239 and HJ706 gave a 793 bp product from amplification of the 3' junction of the marker with the GAL4 downstream sequence by (alternatively, HJ239 and HJ241 were used to give a PCR product of 1038 bp).

Isolates with the genotype gal80Δ::xHph gal4Δ::xKan were transformed with a natA-marked F-CphI expression plasmid (pAM1864). Transformation was outgrown in 3 mL liquid YPD medium for 5 hrs and then plated on YPD plus nourseothricin. After 3 days of incubation at 30° C., 4 transformants were streaked on fresh YPD to lose pAM1864. To test xMarker excision and loss of pAM1864, 50 colonies (about 12-13 colonies from each streak) were patched on a YPD plate and then replica plated on YPD, YPD plus hygromycin, G418, or nourseothricin 24 hrs later. Plates were examined 48 hrs after replica plating.

The frequency of simultaneous multiple integratrion was 100%, that is, 50/50 colonies lost resistance to both hygromycin and G418, indicating that all the colonies tested had lost both xMarkers. About 20% (10/50) colonies also lost resistance to nourseothricin, indicating that 20% of the colonies lost the F-CphI plasmid. Similar frequencies were observed for two additional strains in which two xMarker constructs were genomically integrated. In a second gal80Δ::xHph gal4Δ::xKan strain in which F-CphI was expressed, 50/50 colonies lost resistance to both hygromycin and G418, and 10/50 colonies also lost resistance to nourseothricin. In a third gal80Δ::xHph gal4Δ::xKan strain in which F-CphI was expressed, 48/48 colonies lost resistance to both hygromycin and G418, and 5/50 colonies also lost resistance to nourseothricin. Colonies that lost resistance to all three drugs were also colony PCR verified. As expected, all of them had both xMarkers excised by F-CphI.

This example demonstrates a high frequency of perfect excision of two markers from a single haploid strain. Further, this example demonstrates that there was no evidence for chromosomal translocation or genomic instability. These results indicate that xMarker constructs facilitate highly efficient simultaneous multiple excision of target DNA from a host cell genome.

6.2.5. Genomic Stability of xMarker Constructs Comprising DRs of Varying Length

This example demonstrates the stability of xMarker constructs comprising direct repeats (DRs) of varying lengths when integrated in a yeast genome, in the absence of endonuclease expression.

It is advantageous that a conditional gene deletion system be tightly controlled so that no significant excision occurs prior to induction and under non-inducing conditions. In the context of genome engineering, high rates of spontaneous homologous recombination events can lead to genomic instability, undesired loss of selectable markers, and consequently, a loss in the ability to select for desired genotypes.

Native, endogenous, spontaneous homologous recombination events can catalyze a rare recombinational crossover between directly repeated sequences (generally, >300 bp)

that deletes the intervening DNA. Published reports have shown that a sequence can be excised from a yeast host cell genome via spontaneous recombination crossover between DRs flanking the sequence ("loop-out"). The rate at which such loop-out occurs between DRs of 300 bp to 1.1 kb length have been reported to lie between 1 in 1,000 cells ($1\times10^{-3}$) to 1 in 10,000 cells ($1\times10^{-4}$) (Alani et al. (1987) Genetics 116 (4):541-5 ($10^{-4}$ for direct repeat lengths of 1100 bp); Wach et al. (1994) Yeast 10(13):1793-808 ($10^{-3}$ to $10^{-4}$ for direct repeat length of 430 bp); Erdeniz et al. (1997) Genome Res 7(12):1174-83) ($10^{-3}$ to $10^{-4}$ for direct repeat lengths of ~300 to 3000 bp). To determine the genomic stability of integrated xMarker constructs having varying lengths of direct repeats, the rates of spontaneous recombination crossover between DRs of various lengths were assessed in the absence of endonuclease expression.

Strains with xMarkers integrated at the HXT3 locus (deleting the HXT3 gene), having direct repeat lengths of 50, 60, 80 and 198 bp, were made as follows. The integration vectors were made by stitching the following URA3 xMarker variants with the 01-0-U-407 and 29-0-D-408 RaBits, using the RYSE0 and RYSE19 oligonucleotides as primers:

Colonies were restreaked on CSM lacking uracil, and then, to permit spontaneous excision of the URA3 marker between the DRs, the cells were grown in liquid YPD for 2 days, being diluted every 12-24 hours (resulting in approximately 25 doublings). Since both URA3+ and ura3– colonies grow well in this culture medium, there is no selection for gene excision. In addition, cells comprising native URA3, i.e., URA3 not flanked by any direct repeats, were grown as a control for assessing the rate of spontaneous mutation, which can lead to point mutation(s) that reduce or inactivate the activity of URA3 (leading to survival of host cells on 5-FOA), without loop-out of the URA3 coding sequence.

Cultures were finally plated on solid medium containing 5-FOA and grown for another 2.5 days before colonies were counted. 16 individual ura3-(5-FOA resistant) colonies for each genotype were confirmed by colony PCR for spontaneous loop-out of the URA3 gene, or alternatively, for the presence of an intact URA3 gene. Primers were used that flanked the integration site of the marker (oligonucleotides KB503 and KB604). A PCR product size of 533 bp confirmed that URA3 was cleanly excised.

TABLE 15

List of characteristics of individual elements of xMarkers used to assess the effect of tandem repeat length on genomic stability

| name of URA3 xMarker | length of DR (bp) | ES sites (#) | orientation of ES sites to each other | DR (scar) sequence |
|---|---|---|---|---|
| 50 mer-direct (aka xM0_URA3) | 50 | F-CphI (2) | direct | AAGATCCGATCGACCGAGAACTGAG AACGGTGCAATGATCAACATGATCT (SEQ ID NO: 23) |
| 60mer-direct (aka s0x-URA3) | 60 | I-SceI (2) | direct | AAGATCCGATCGACCGAGAACTGAG AACGGTGCAATGATCAACATGATCTG CGACGAGCT (SEQ ID NO: 10) |
| 80mer-direct | 80 | I-SceI (2) | direct | AAGATCCGATCGACCGAGAACTGAG AACGGTGCAATGATCAACATGATCTG CGACGAGCTTGAGGATGCAAATGGCT GAC (SEQ ID NO: 85) |
| 198mer-direct (aka Rabit 606) | 198 | 0 | direct | TCACTATTATTCCATAAGATGATCATT AGCATTACGTTCAAAACGAGTACAAA TAACTTAAGTAATAACACGAGCCATA TGACCATTAGCAAGATGACAAGCAAG TTAAGACCAATCAGCTTCCATCATAG CATCAGCTTAACGTTCACCATTAATA AGAGTAGAAATTTCACCTTCAAGACA ATAACGATTTTCGTG (SEQ ID NO: 145) |

After transformation into a ura3– strain, cells were plated on CSM lacking uracil, and colonies were verified for correct integration by colony PCR (cPCR). The primers were KB502, KB503, and CPK904; the latter two produced a 738 bp fragment for hxt3Δ::xURA3 and the former two produced a 538 bp fragment for intact HXT3. cPCR results confirmed integration of the xMarker and disruption of HXT3. Two confirmed isolates for each xMarker variant were chosen for further analysis.

As shown in Table 16, the average frequency of 5-FOA resistance in cells comprising URA3 not flanked by direct repeats was approximately $1.7\times10^{-6}$ cells, which indicates the intrinsic rate of spontaneous mutation leading to inactivation of URA3. The average frequency of 5-FOA resistance in cells comprising URA3 flanked by direct repeats of 50-80 bp length was approximately $4.5\times10^{-6}$ to $1.14\times10^{-5}$ cells, and the average frequency of 5-FOA resistance in cells comprising URA3 flanked by direct repeats of 198 bp length was approximately $4.7\times10^{-5}$ cells.

Colony PCR results confirmed that some amount of the 5-FOA resistant xMarker colonies arose as a result of spontaneous mutation leading to inactivation of URA3, as opposed to loop-out of the URA3 marker. In particular, for colonies comprising integrated xMarker constructs having 50 bp and 80 bp DR lengths, four out of twelve (4/12) 5-FOA resistant colonies screened by cPCR had intact URA3 genes, indicating that 5-FOA resistance in these colonies arose from inactivating spontaneous mutations in URA3 rather than URA3 loop-out. Thus, the frequency of DR-mediated spontaneous loop-out in the xMarker strains is expected to be even lower than the observed frequency of 5-FOA resistance. Even with the understanding of this limitation, using 5-FOA resistance as a proxy, these results indicate that the frequency of spontaneous loop-out associated with DR lengths of about 50 to 200 bp is 1 to 3 orders of magnitude lower than the rates of spontaneous loop-out reported for DRs of 300 bp to 1.1 kb ($10^{-6}$ to $10^{-5}$ versus $10^{-4}$ to $10^{-3}$, as discussed above). In particular, a DR length of about 200 bp provides a 1-2 log reduction in the number of spontaneous loop-out events compared to a DR length of at least 300 bp. The results for shorter DR lengths are even more dramatic. As described above, the results demonstrate that a DR length in the range of 50 to 80 bp provides a 2-3 log reduction in the number of spontaneous loop-out events compared to a DR length of at least 300 bp ($10^{-6}$ to $10^{-5}$ versus $10^{-4}$ to $10^{-3}$). Furthermore, these results indicate that the rates of spontaneous URA3 loop-out approach the rate of spontaneous mutation of URA3 as the lengths of the DRs decrease below 200. DR lengths of 50, 60 and 80 resulted in only a roughly 2.7 to 7-fold increase in loss of URA3 due to loop-out compared to spontaneous inactivating mutation.

These results suggest that DR lengths of about 200 bp or shorter provide substantial advantages with respect to genomic stability when compared to DR lengths of 300 bp or higher. The excision of target DNA is controlled tightly and no significant excision prior to induction with a homing endonuclease. Accordingly, the xMarker methods and compositions described herein provide improved retention of target DNA, e.g., selectable markers, under non-inducing conditions, which can result in greater genomic stability and more efficient selection of desired genotypes during strain engineering.

These results demonstrate that the compositions and methods described herein, for creating and excising specialized variants of selectable markers, work with high frequency, efficiency, fidelity and stability. The I-SceI and F-CphI endonucleases work well for this approach, with F-CphI showing unexpectedly exceptional excision frequency and fidelity in S. cerevisiae cells. The excision events themselves do not cause genomic instability even in diploid cells and even in cells with more than one xMarker. Major advantages of this approach include the ability to simultaneously excise many xMarkers at once and the ability to choose a large variety of unique scar sequences, such that even repeated use and recycling of xMarkers in the same strain can be designed such that each scar is unique. This is an advantage over Flp/FRT or Cre/lox systems that necessarily leave behind multiple copies of the binding and cleavage site for the site-specific recombinase, littered throughout the genome, waiting to be cleaved again upon re-introduction of the recombinase, which potentially causes translocations and excisions of chromosome segments. Another advantage is that the excision frequency is often higher than 50%, and thus the approach can be used to excise any desired target DNA, using a screening approach to identify the desired product strains, even when there is no selection method available to permit growth only of the successfully excised product isolates.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 16

Spontaneous recombination events mediated by direct repeats (DRs) of various lengths

| DR length | isolate | avg. # of colonies | Std. dev. | # of cells plated | frequency of 5-FOA resistance | avg. 5-FOA resistance | # of colonies tested by cPCR | # of colonies lacking URA3 gene | # of colonies with URA3 gene |
|---|---|---|---|---|---|---|---|---|---|
| 0 | a | 32.17 | 16.69 | 2.68E+07 | 1.20E−06 | | 16 | 0 | 16 |
| 0 | b | 57.67 | 34.14 | 2.72E+07 | 2.12E−06 | 1.66E−06 | | | |
| 50 | a | 240.83 | 157.67 | 2.76E+07 | 8.74E−06 | | 16 | 12 | 4 |
| 50 | b | 164.67 | 68.95 | 2.74E+07 | 6.02E−06 | 7.38E−06 | | | |
| 60 | a | 260.83 | 142.14 | 2.74E+07 | 9.52E−06 | | 16 | 15 | 1 |
| 60 | b | 361.00 | 214.56 | 2.72E+07 | 1.33E−05 | 1.14E−05 | | | |
| 80 | a | 113.83 | 53.15 | 2.58E+07 | 4.41E−06 | | 16 | 12 | 4 |
| 80 | b | 116.33 | 22.91 | 2.49E+07 | 4.67E−06 | 4.54E−06 | | | |
| 198 | a | 1212.00 | 343.09 | 2.52E+07 | 4.81E−05 | | 16 | 16 | 0 |
| 198 | b | 1118.67 | 132.32 | 2.44E+07 | 4.58E−05 | 4.69E−05 | | | |

What is claimed:

1. An excisable nucleic acid construct comprising, in a 5' to 3' orientation:
   (a) a first genomic integration sequence;
   (b) a first tandem repeat nucleic acid consisting of 18 to 200 nucleotide base pairs;
   (c) a first homing endonuclease recognition site;
   (d) a target nucleic acid;
   (e) a second homing endonuclease recognition site;
   (f) a second tandem repeat nucleic acid consisting of 18 to 200 nucleotide base pairs; and
   (g) a second genomic integration sequence,
   wherein each of the first and second genomic integration sequences is of sufficient length and identity to initiate homologous recombination with a yeast genomic locus, wherein the first tandem repeat nucleic acid and the second tandem repeat nucleic acid share identical sequences, and wherein the first homing endonuclease recognition site and the second homing endonuclease recognition site share identical sequences.

2. The excisable nucleic acid construct of claim 1, wherein each of the first and second tandem repeat nucleic acids independently consists of 18 to 150 nucleotide base pairs.

3. The excisable nucleic acid construct of claim 1, wherein each of the first and second tandem repeat nucleic acids independently consists of 18 to 100 nucleotide base pairs.

4. The excisable nucleic acid construct of claim 1, wherein each of the first and second homing endonuclease recognition sites independently consists of 18 to 80 nucleotide base pairs.

5. The excisable nucleic acid construct of claim 1, wherein each of the first and second homing endonuclease recognition sites is a recognition site for a homing endonuclease selected from the group consisting of: an LAGLIDADG (SEQ ID NO: 1) homing endonuclease, a HNH homing endonuclease, an His-Cys box homing endonuclease, a GIY-YIG (SEQ ID NO: 2) homing endonuclease, and a cyanobacterial homing endonuclease.

6. The excisable nucleic acid construct of claim 1, wherein each of the first and second homing endonuclease recognition sites is a recognition site for a homing endonuclease selected from the group consisting of: I-CreI, I-MsoI, I-SceI, I-SceIV, H-DreI, I-HmuI, I-PpoI, I-Did, I-NjaI, I-NanI, I-NitI, I-TevI, I-TevII, I-TevIII, F-TevI, F-TevII, F-CphI, PI-MgaI, I-CsmI, I-CeuI, and PI-SceI.

7. The excisable nucleic acid construct of claim 1, wherein at least one of the first or second homing endonuclease recognition sites is a recognition site for I-SceI.

8. The excisable nucleic acid construct of claim 1, wherein at least one of the first or second homing endonuclease recognition sites is a recognition site for F-CphI.

9. The excisable nucleic acid construct of claim 1, wherein the target nucleic acid encodes a selectable marker.

10. The excisable nucleic acid construct of claim 9, wherein the selectable marker is selected from the group consisting of: URA3, hygromycin B phosphotransferase, aminoglycoside phosphotransferase, zeocin resistance gene and phosphinothricin N-acetyltransferase.

11. The excisable nucleic acid construct of claim 1, wherein each of the first and second genomic integration sequences independently consists of about 50 to 5000 nucleotide base pairs.

12. The excisable nucleic acid construct of claim 1, wherein each of the first and second genomic integration sequences independently consists of about 500 nucleotide base pairs.

13. A yeast cell comprising the excisable nucleic acid construct of claim 1.

14. A yeast cell comprising:
   (a) an excisable nucleic acid construct comprising, in a 5' to 3' orientation:
      (i) a first tandem repeat nucleic acid consisting of 18 to 200 nucleotide base pairs;
      (ii) a first homing endonuclease recognition site;
      (iii) a target nucleic acid;
      (iv) a second homing endonuclease recognition site; and
      (v) a second tandem repeat nucleic acid consisting of 18 to 200 nucleotide base pairs,
      wherein the first tandem repeat nucleic acid and the second tandem repeat nucleic acid share identical sequences, and wherein the first homing endonuclease recognition site and the second homing endonuclease recognition site share identical sequences; and
   (b) a vector comprising a homing endonuclease nucleic acid encoding a homing endonuclease capable of binding to and cleaving at or adjacent to at least one of the first or second homing endonuclease recognition sites.

15. A method of excising at least one target nucleic acid from the genome of a host cell comprising a first excisable nucleic acid construct, wherein the first excisable nucleic acid construct comprises, in a 5' to 3' orientation:
   (a) a first tandem repeat nucleic acid consisting of 18 to 200 nucleotide base pairs;
   (b) a first homing endonuclease recognition site;
   (c) a first target nucleic acid;
   (d) a second homing endonuclease recognition site; and
   (e) a second tandem repeat nucleic acid consisting of 18 to 200 nucleotide base pairs, wherein the first tandem repeat nucleic acid and the second tandem repeat nucleic acid share identical sequences, and wherein the first homing endonuclease recognition site and the second homing endonuclease recognition site share identical sequences, wherein the method comprises contacting the first excisable nucleic acid construct with a homing endonuclease in the host cell such that the homing endonuclease cleaves at or adjacent to at least one of the first or second homing endonuclease recognition sites.

16. The method of claim 15, wherein the host cell further comprises a second excisable nucleic acid construct, the host cell thereby comprising at least two excisable nucleic acid constructs, wherein the second excisable nucleic acid construct comprises, in a 5' to 3' orientation:
   (a) a third tandem repeat nucleic acid;
   (b) a third homing endonuclease recognition site;
   (c) a second target nucleic acid;

(d) a fourth homing endonuclease recognition site; and
(e) a fourth tandem repeat nucleic acid;
wherein the third tandem repeat nucleic acid and the fourth tandem repeat nucleic acid share identical sequences, and wherein the third homing endonuclease recognition site and the fourth homing endonuclease recognition site share identical sequences, wherein the method comprises: contacting the at least two excisable nucleic acid constructs with a homing endonuclease in the host cell such that the homing endonuclease cleaves at or adjacent to at least one of the homing endonuclease recognition sites of each excisable nucleic acid construct, thereby simultaneously excising the target nucleic acids from the genome of the host cell.

17. The method of claim 16, wherein each of the tandem repeat nucleic acids of each excisable nucleic acid construct independently consists of 18 to 200 nucleotide base pairs.

18. The method of claim 16, wherein each of the tandem repeat nucleic acids of each excisable nucleic acid construct independently consists of 18 to 150 nucleotide base pairs.

* * * * *

UNITED STATES PATENT AND TRADEMARK OFFICE
CERTIFICATE OF CORRECTION

PATENT NO.      : 9,018,364 B2
APPLICATION NO. : 13/220553
DATED           : April 28, 2015
INVENTOR(S)     : Kirsten Benjamin It is certified that error appears in the above-identified patent and that said Letters Patent is hereby corrected as shown below:

In the Claims

Column 131, line 52, Claim 6, "I-Did" should be changed to --I-DirI--.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 145

<210> SEQ ID NO 1
<211> LENGTH: 9
<212> TYPE: PRT
<213> ORGANISM: Artificial Sequence
<220> FEATURE:
<223> OTHER INFORMATION: Motif sequence for LAGLIDADG homing
      endonuclease

<400> SEQUENCE: 1

Leu Ala Gly Leu Ile Asp Ala Asp Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Motif sequence for GIY-YIG homing endonuclease

<400> SEQUENCE: 2

Gly Ile Tyr Tyr Ile Gly
1               5

<210> SEQ ID NO 3
<211> LENGTH: 18
<212> TYPE: DNA
<213> ORGANISM: Artificial Sequence
<220> FEATURE:
<223> OTHER INFORMATION: Recognition sequence for I-SceI

<400> SEQUENCE: 3
tagggataac agggtaat                                                    18

<210> SEQ ID NO 4
<211> LENGTH: 31
<212> TYPE: DNA
<213> ORGANISM: Artificial Sequence
<220> FEATURE:
<223> OTHER INFORMATION: Recognition sequence for VDE (PI-SceI)

<400> SEQUENCE: 4
tatgtcgggt gcggagaaag aggtaatgaa a                                     31

<210> SEQ ID NO 5
<211> LENGTH: 24
<212> TYPE: DNA
<213> ORGANISM: Artificial Sequence
<220> FEATURE:
<223> OTHER INFORMATION: Recognition sequence for F-Cph

<400> SEQUENCE: 5
gatgcacgag cgcaacgctc acaa                                             24

<210> SEQ ID NO 6
<211> LENGTH: 24
<212> TYPE: DNA
<213> ORGANISM: Artificial Sequence
<220> FEATURE:
<223> OTHER INFORMATION: Recognition sequence for PI-MgaI (pps1)

<400> SEQUENCE: 6
gcgtagctgc ccagtatgag tcag                                             24

<210> SEQ ID NO 7

-continued

```
<211> LENGTH: 40
<212> TYPE: DNA
<213> ORGANISM: Artificial Sequence
<220> FEATURE:
<223> OTHER INFORMATION: Recognition sequence for PI-MtuII (pps1)

<400> SEQUENCE: 7
acgtgcacta cgtagagggt cgcaccgcac cgatctacaa                               40

<210> SEQ ID NO 8
<211> LENGTH: 20
<212> TYPE: DNA
<213> ORGANISM: Artificial Sequence
<220> FEATURE:
<223> OTHER INFORMATION: Directly repeated sequence (DR) s20M

<400> SEQUENCE: 8
aagatccgat cgaccgagaa                                                    20

<210> SEQ ID NO 9
<211> LENGTH: 40
<212> TYPE: DNA
<213> ORGANISM: Artificial Sequence
<220> FEATURE:
<223> OTHER INFORMATION: Directly repeated sequence (DR) s40M

<400> SEQUENCE: 9
aagatccgat cgaccgagaa ctgagaacgg tgcaatgatc                               40

<210> SEQ ID NO 10
<211> LENGTH: 60
<212> TYPE: DNA
<213> ORGANISM: Artificial Sequence
<220> FEATURE:
<223> OTHER INFORMATION: Directly repeated sequence (DR) s60M

<400> SEQUENCE: 10
aagatccgat cgaccgagaa ctgagaacgg tgcaatgatc aacatgatct gcgacgagct         60

<210> SEQ ID NO 11
<211> LENGTH: 80
<212> TYPE: DNA
<213> ORGANISM: Artificial Sequence
<220> FEATURE:
<223> OTHER INFORMATION: Directly repeated sequence (DR) s80M

<400> SEQUENCE: 11
aagatccgat cgaccgagaa ctgagaacgg tgcaatgatc aacatgatct gcgacgagct         60
tgaggatgca aatggctgac                                                    80

<210> SEQ ID NO 12
<211> LENGTH: 60
<212> TYPE: DNA
<213> ORGANISM: Artificial Sequence
<220> FEATURE:
<223> OTHER INFORMATION: Single sequence s60M

<400> SEQUENCE: 12
aagatccgat cgaccgagaa ctgagaacgg tgcaatgatc aacatgatct gcgacgagct         60

<210> SEQ ID NO 13
<211> LENGTH: 60
<212> TYPE: DNA
<213> ORGANISM: Artificial Sequence
<220> FEATURE:
<223> OTHER INFORMATION: s1x_hphA repeat sequence
```

<400> SEQUENCE: 13
cgttacgaag cacacactag ttagcgtcga gacacatagc gacgctagaa cttgcgactt    60

<210> SEQ ID NO 14
<211> LENGTH: 60
<212> TYPE: DNA
<213> ORGANISM: Artificial Sequence
<220> FEATURE:
<223> OTHER INFORMATION: s2x_hphA repeat sequence

<400> SEQUENCE: 14
gtactgccta gtagaaacgg atctccacgt actagagtcc acctggtatc tattagcccg    60

<210> SEQ ID NO 15
<211> LENGTH: 60
<212> TYPE: DNA
<213> ORGANISM: Artificial Sequence
<220> FEATURE:
<223> OTHER INFORMATION: s3x_kanA repeat sequence

<400> SEQUENCE: 15
cgaggattaa cgtgtaaggc cctaagctat gtaccgcatc tcctaagaga gtgtgaccca    60

<210> SEQ ID NO 16
<211> LENGTH: 60
<212> TYPE: DNA
<213> ORGANISM: Artificial Sequence
<220> FEATURE:
<223> OTHER INFORMATION: s4x_kanA repeat sequence

<400> SEQUENCE: 16
ttaatcagcg cccagagact agcactgaat gatcaacggg tagttcacac actgccagac    60

<210> SEQ ID NO 17
<211> LENGTH: 60
<212> TYPE: DNA
<213> ORGANISM: Artificial Sequence
<220> FEATURE:
<223> OTHER INFORMATION: s5x_natA repeat sequence

<400> SEQUENCE: 17
atggaatcac ggggctattc cacttgctaa taacgaggcg cttatcaacg gcgagcacat    60

<210> SEQ ID NO 18
<211> LENGTH: 60
<212> TYPE: DNA
<213> ORGANISM: Artificial Sequence
<220> FEATURE:
<223> OTHER INFORMATION: s6x_natA repeat sequence

<400> SEQUENCE: 18
agtcaaagcg cgattcgcta ggaatgagag cgagaacgaa ccggagtata tcacaatcgc    60

<210> SEQ ID NO 19
<211> LENGTH: 60
<212> TYPE: DNA
<213> ORGANISM: Artificial Sequence
<220> FEATURE:
<223> OTHER INFORMATION: s7x_URA3 repeat sequence

<400> SEQUENCE: 19
actagagcga aatggagagg tacgtgatcc tactagagcc cacgctatca tacagttggc    60

<210> SEQ ID NO 20

```
<211> LENGTH: 60
<212> TYPE: DNA
<213> ORGANISM: Artificial Sequence
<220> FEATURE:
<223> OTHER INFORMATION: s8x_URA3 repeat sequence

<400> SEQUENCE: 20
gtacgtccgt acttatgctg agcgctccta cacgaaaaac tcaccgtgac tagcataacg      60

<210> SEQ ID NO 21
<211> LENGTH: 20
<212> TYPE: DNA
<213> ORGANISM: Artificial Sequence
<220> FEATURE:
<223> OTHER INFORMATION: I-SceI primer sequence

<400> SEQUENCE: 21
gctagggata acagggtaat                                                  20

<210> SEQ ID NO 22
<211> LENGTH: 20
<212> TYPE: DNA
<213> ORGANISM: Artificial Sequence
<220> FEATURE:
<223> OTHER INFORMATION: I-SceI primer sequence

<400> SEQUENCE: 22
actagggata acaggtttat                                                  20

<210> SEQ ID NO 23
<211> LENGTH: 50
<212> TYPE: DNA
<213> ORGANISM: Artificial Sequence
<220> FEATURE:
<223> OTHER INFORMATION: Directly repeated sequence (DR) xM0

<400> SEQUENCE: 23
aagatccgat cgaccgagaa ctgagaacgg tgcaatgatc aacatgatct                 50

<210> SEQ ID NO 24
<211> LENGTH: 50
<212> TYPE: DNA
<213> ORGANISM: Artificial Sequence
<220> FEATURE:
<223> OTHER INFORMATION: Directly repeated sequence (DR) xM1

<400> SEQUENCE: 24
cgttacgaag cacacactag ttagcgtcga gacacatagc gacgctagaa                 50

<210> SEQ ID NO 25
<211> LENGTH: 50
<212> TYPE: DNA
<213> ORGANISM: Artificial Sequence
<220> FEATURE:
<223> OTHER INFORMATION: Directly repeated sequence (DR) xM2

<400> SEQUENCE: 25
gtactgccta gtagaaacgg atctccacgt actagagtcc acctggtatc                 50

<210> SEQ ID NO 26
<211> LENGTH: 50
<212> TYPE: DNA
<213> ORGANISM: Artificial Sequence
<220> FEATURE:
<223> OTHER INFORMATION: Directly repeated sequence (DR) xM3

<400> SEQUENCE: 26
```

```
cgaggattaa cgtgtaaggc cctaagctat gtaccgcatc tcctaagaga         50
```

<210> SEQ ID NO 27
<211> LENGTH: 50
<212> TYPE: DNA
<213> ORGANISM: Artificial Sequence
<220> FEATURE:
<223> OTHER INFORMATION: Directly repeated sequence (DR) xM4

<400> SEQUENCE: 27

```
ttaatcagcg cccagagact agcactgaat gatcaacggg tagttcacac         50
```

<210> SEQ ID NO 28
<211> LENGTH: 50
<212> TYPE: DNA
<213> ORGANISM: Artificial Sequence
<220> FEATURE:
<223> OTHER INFORMATION: Directly repeated sequence (DR) xM5

<400> SEQUENCE: 28

```
gaatcacggg gctattccac ttgctaataa cgaggcgctt atcaacggcg         50
```

<210> SEQ ID NO 29
<211> LENGTH: 50
<212> TYPE: DNA
<213> ORGANISM: Artificial Sequence
<220> FEATURE:
<223> OTHER INFORMATION: Directly repeated sequence (DR) xM6

<400> SEQUENCE: 29

```
gtcaaagcgc gattcgctag gaatgagagc gagaacgaac cggagtatat         50
```

<210> SEQ ID NO 30
<211> LENGTH: 50
<212> TYPE: DNA
<213> ORGANISM: Artificial Sequence
<220> FEATURE:
<223> OTHER INFORMATION: Directly repeated sequence (DR) xM7

<400> SEQUENCE: 30

```
actagagcga aatggagagg tacgtgatcc tactagagcc cacgctatca         50
```

<210> SEQ ID NO 31
<211> LENGTH: 50
<212> TYPE: DNA
<213> ORGANISM: Artificial Sequence
<220> FEATURE:
<223> OTHER INFORMATION: Directly repeated sequence (DR) xM8

<400> SEQUENCE: 31

```
gtacgtccgt acttatgctg agcgctccta cacgaaaaac tcaccgtgac         50
```

<210> SEQ ID NO 32
<211> LENGTH: 50
<212> TYPE: DNA
<213> ORGANISM: Artificial Sequence
<220> FEATURE:
<223> OTHER INFORMATION: Directly repeated sequence (DR) xM9

<400> SEQUENCE: 32

```
gcattaagtc gtagctagcg gattctctct tcgtgcatcc tagcaaatgg         50
```

<210> SEQ ID NO 33
<211> LENGTH: 2733
<212> TYPE: DNA

<213> ORGANISM: Artificial Sequence
<220> FEATURE:
<223> OTHER INFORMATION: RYSE 12 entry vector

<400> SEQUENCE: 33

```
gtaaaacgac ggccagtatt aaccctcact aaagggaact cgaggctctt cagctcacac      60
gcggccaggg ggagcctggc agactccata tgctatgcgg catcagagca gattgtactg     120
agagtgcacc atatgcggtg tgaaataccg cacagatgcg taaggagaaa ataccgcatc     180
aggcgccatt cgccattcag ctgcgcaac tgttgggaag ggcgatcggt gcgggcctct      240
tcgctattac gccagctggc gaaaggggga tgtgctgcaa ggcgattaag ttgggtaacg     300
ccagggtttt cccagtcacg acgttgtaaa acgacggcca gtgaattcga gctcggtacc     360
cggggatcct ctagcgtcga cctgcaggca tgcaagcttg gcgtaatcat ggtcatagct     420
gtttcctgtg tgaaattgtt atccgctcac aattccacac aacatacgag ccggaagcat     480
aaagtgtaaa gcctggggtg cctaatgagt gagctaactc acattaattg cgttgcgcgc     540
tagcgagtca tccacgctcg tccaacgccg gcggaccttg aagagcgagc tcccgctgag     600
caataactag cgtcatagct gtttcctggg tcgttcggct gcggcagcg gtatcagctc      660
actcaaaggc ggtaatacgg ttatccacag aatcagggga taacgcagga agaacatgt      720
gagcaaaagg ccagcaaaag gccaggaacc gtaaaaaggc cgcgttgctg gcgttttttcc     780
ataggctccg cccccctgac gagcatcaca aaaatcgacg ctcaagtcag aggtggcgaa     840
acccgacagg actataaaga taccaggcgt ttccccctgg aagctccctc gtgcgctctc     900
ctgttccgac cctgccgctt acccgatacc tgtccgcctt tctcccttcg ggaagcgtgg     960
cgctttctca tagctcacgc tgtaggtatc tcagttcggt gtaggtcgtt cgctccaagc    1020
tgggctgtgt gcacgaaccc cccgttcagc ccgaccgctg cgccttatcc ggtaactatc    1080
gtcttgattc aacccggta agacacgact tatcgccact ggcagcagcc actggtaaca    1140
ggattagcag agcgaggtat gtaggcggtg ctacagagtt cttgaagtgg tggcctaact    1200
acggctacac tagaagaaca gtatttggta tctgcgctct gctgaagcca gttaccttcg    1260
gaaaaagagt tggtagctct tgatccggca acaaaccac cgctggtagc ggtggttttt    1320
ttgtttgcaa gcagcagatt acgcgcagaa aaaaaggatc tcaagaagat cctttgatct    1380
tttctacggg gtctgacgct cagtggaacg aaaactcacg ttaagggatt ttggtcatga    1440
gattatcaaa aaggatcttc acctagatcc ttttaaatta aaaatgaagt tttaaatcaa    1500
tctaaagtat atatgagtaa cttggtcgca tgcttaccaa tgcttaatca gtgaggcacc    1560
tatctcagcg atctgtctat ttcgttcatc catagttgcc tgactgcccg tcgtgtagat    1620
aactacgata cgggagggct taccatctgg ccccagtgct gcaatgatac cgcgagaccc    1680
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
```

```
aaaactctca aggatcttac cgctgttgag atccagttcg atgtaaccca ctcgtgcacc    2280
caactgatct tcagcatctt ttactttcac cagcgtttct gggtgagcaa aaacaggaag    2340
gcaaaatgcc gcaaaaaagg gaataagggc gacacggaaa tgttgaatac tcatcaattg    2400 ccttttcaa tattattgaa gcatttatca gggttattgt ctcatgagcg ttacatatt     2460 tgaatgtatt tagaaaaata aacaaatagg ggttccgcgc acatttcccc gaaaagtgcc    2520
acctgacgtc taagaaacca ttattatcat gacattaacc tataaaaata ggcgtatcac    2580
gaggcccttt catctcgcgc gtttcggtga tgacggtgaa aacctctgac acatgcagct    2640
cccggagaca gtcacagctt gtctgtaagc ggatgccggg agcagacaag cccgtcaggg    2700
cgcgtcagcg ggtgttggcg ggtgtcgggg ctg                                2733

<210> SEQ ID NO 34
<211> LENGTH: 1692
<212> TYPE: DNA
<213> ORGANISM: Artificial Sequence
<220> FEATURE:
<223> OTHER INFORMATION: xMarker ss60M.URA.I-SceI

<400> SEQUENCE: 34
aagatccgat cgaccgagaa ctgagaacgg tgcaatgatc aacatgatct gcgacgagct      60
tagggataac agggtaatat gcgtccatct ttacagtcct gtcttattgt tcttgatttg     120
tgccccgtaa aatactgtta cttggttctg gcgaggtatt ggatagttcc tttttataaa    180
ggccatgaag cttttctttt ccaatttttt ttttttcgtc attatagaaa tcattacgac    240
cgagattccc gggtaataac tgatataatt aaattgaagc tctaatttgt gagtttagta    300
tacatgcatt tacttataat acagtttttt agttttgctg gccgcatctt ctcaaatatg    360
cttcccagcc tgcttttctg taacgttcac cctctacctt agcatccctt cccttttgcaa   420 atagtcctct tccaacaata ataatgtcag atcctgtaga gaccacatca tccacggttc    480
tatactgttg acccaatgcg tctcccttgt catctaaacc cacaccgggt gtcataatca    540
accaatcgta accttcatct cttccaccca tgtctctttg agcaataaag ccgataacaa    600
aatctttgtc actcttcgca atgtcaacag taccctagt atattctcca gtagataggg     660
agcccttgca tgacaattct gctaacatca aaaggcctct aggttccttt gttacttctt    720
ctgccgcctg cttcaaaccg ctaacaatac ctgggcccac cacaccgtgt gcattcgtaa    780
tgtctgccca ttctgctatt ctgtatacac ccgcagagta ctgcaatttg actgtattac    840
caatgtcagc aaattttctg tcttcgaaga gtaaaaaatt gtacttggcg ataatgcctt    900
ttagcggctt aactgtgccc tccatggaaa atcagtcaa gatatccaca tgtgttttta     960
gtaaacaaat tttgggacct aatgcttcaa ctaactccag taattccttg gtggtacgaa    1020
catccaatga agcacacaag tttgtttgct tttcgtgcat gatattaaat agcttggcag    1080
caacaggact aggatgagta gcagcacgtt cctatatgt agctttcgac atgatttatc     1140
ttcgtttcct gcaggttttt gttctgtgca gttgggttaa gaatactggg caatttcatg    1200
tttcttcaac accacatatg cgtatatata ccaatctaag tctgtgctcc ttccttcgtt    1260
cttccttctg ctcggagatt accgaatcaa aaaaatttca agaaaccgg aatcaaaaaa      1320 aagaacaaaa aaaaaaaga tgaattgaaa agctttatgg accctgaaac cacagccaca    1380
ttaaccttct tgatggtca aaacttatcc ttcaccataa atatgcctcg caaaaaggt       1440 aattaacata tatagaatta cattatttat gaaatatcat cactatctct tagcatcttt    1500
```

```
aatccttttc tacatcagat aacttcggtt tgttatcatc gtctgtattg tcatcaattg    1560
gcgcagtagc ctcaatttca acgtcgtttg actctggtgt tgttcatgt gcagatccat    1620 gagatgatga acaagatccg atcgaccgag aactgagaac ggtgcaatga tcaacatgat   1680
ctgcgacgag ct                                                       1692
```

<210> SEQ ID NO 35
<211> LENGTH: 1602
<212> TYPE: DNA
<213> ORGANISM: Artificial Sequence
<220> FEATURE:
<223> OTHER INFORMATION: RaBit12-0-M-555

<400> SEQUENCE: 35

```
gctcacacgc ggccaggggg agccgttcat catctcatgg atctgcacat gaacaaacac     60
cagagtcaaa cgacgttgaa attgaggcta ctgcgccaat tgatgacaat acagacgatg    120
ataacaaacc gaagttatct gatgtagaaa aggattaaag atgctaagag atagtgatga    180
tatttcataa ataatgtaat tctatatatg ttaattacct tttttgcgag gcatatttat    240
ggtgaaggat aagttttgac catcaaagaa ggttaatgtg gctgtggttt cagggtccat    300
aaagcttttc aattcatctt ttttttttt gttcttttt ttgattccgg tttcttgaa      360 atttttttga ttcggtaatc tccgagcaga aggaagaacg aaggaaggag cacagactta    420
gattggtata tatacgcata tgtggtgttg aagaaacatg aaattgccca gtattcttaa    480
cccaactgca cagaacaaaa acctgcagga aacgaagata atcatgtcg aaagctacat     540 ataaggaacg tgctgctact catcctagtc ctgttgctgc caagctattt aatatcatgc    600
acgaaaagca aacaaacttg tgtgcttcat tggatgttcg taccaccaag gaattactgg    660
agttagttga agcattaggt cccaaaattt gtttactaaa aacacatgtg gatatcttga    720 ctgattttc catggagggc acagttaagc cgctaaaggc attatccgcc aagtacaatt     780
ttttactctt cgaagacaga aaatttgctg acattggtaa tacagtcaaa ttgcagtact    840
ctgcgggtgt atacagaata gcagaatggg cagacattac gaatgcacac ggtgtggtgg    900
gcccaggtat tgttagcggt ttgaagcagg cggcagaaga agtaacaaag gaacctagag    960 gcctttttgat gttagcagaa ttgtcatgca agggctccct atctactgga gaatatacta   1020
agggtactgt tgacattgcg aagagtgaca aagattttgt tatcggcttt attgctcaaa    1080
gagacatggg tggaagagat gaaggttacg attggttgat tatgacaccc ggtgtgggtt    1140
tagatgacaa gggagacgca ttgggtcaac agtatagaac cgtggatgat gtggtctcta    1200
caggatctga cattattatt gttggaagag gactatttgc aaagggaagg gatgctaagg    1260
tagagggtga acgttacaga aaagcaggct gggaagcata tttgagaaga tgcggccagc    1320
aaaactaaaa aactgtatta taagtaaatg catgtatact aaactcacaa attagagctt    1380
caatttaatt atatcagtta ttacccggga atctcggtcg taatgatttc tataatgacg    1440
aaaaaaaaaa aattggaaag aaaaagcttc atggccttta taaaaggaa ctatccaata    1500 cctcgccaga accaagtaac agtattttac ggggcacaaa tcaagaacaa taagacagga    1560
ctgtaaagat ggacgcatcg ctcgtccaac gccggcggac ct                      1602
```

<210> SEQ ID NO 36
<211> LENGTH: 95
<212> TYPE: DNA
<213> ORGANISM: Artificial Sequence
<220> FEATURE:
<223> OTHER INFORMATION: Primer KB520-266-136

```
<400> SEQUENCE: 36
aagatccgat cgaccgagaa ctgagaacgg tgcaatgatc aacatgatct gatgcacgag    60
cgcaacgctc acaagttcat catctcatgg atctg                              95

<210> SEQ ID NO 37
<211> LENGTH: 93
<212> TYPE: DNA
<213> ORGANISM: Artificial Sequence
<220> FEATURE:
<223> OTHER INFORMATION: Primer KB521-266-136

<400> SEQUENCE: 37
agatcatgtt gatcattgca ccgttctcag ttctcggtcg atcggatctt gtgagcgttg    60
cgctcgtgca tcatgcgtcc atctttacag tcc                                93

<210> SEQ ID NO 38
<211> LENGTH: 95
<212> TYPE: DNA
<213> ORGANISM: Artificial Sequence
<220> FEATURE:
<223> OTHER INFORMATION: Primer KB522-266-136

<400> SEQUENCE: 38
aagatccgat cgaccgagaa ctgagaacgg tgcaatgatc aacatgatct gcgtagctgc    60
ccagtatgag tcaggttcat catctcatgg atctg                              95

<210> SEQ ID NO 39
<211> LENGTH: 95
<212> TYPE: DNA
<213> ORGANISM: Artificial Sequence
<220> FEATURE:
<223> OTHER INFORMATION: Primer KB523-266-136

<400> SEQUENCE: 39
agatcatgtt gatcattgca ccgttctcag ttctcggtcg atcggatctt ctgactcata    60
ctgggcagct acgcatgcgt ccatctttac agtcc                              95

<210> SEQ ID NO 40
<211> LENGTH: 111
<212> TYPE: DNA
<213> ORGANISM: Artificial Sequence
<220> FEATURE:
<223> OTHER INFORMATION: Primer KB524-266-136

<400> SEQUENCE: 40
aagatccgat cgaccgagaa ctgagaacgg tgcaatgatc aacatgatct acgtgcacta    60
cgtagagggt cgcaccgcac cgatctacaa gttcatcatc tcatggatct g            111

<210> SEQ ID NO 41
<211> LENGTH: 109
<212> TYPE: DNA
<213> ORGANISM: Artificial Sequence
<220> FEATURE:
<223> OTHER INFORMATION: Primer KB525-266-136

<400> SEQUENCE: 41
agatcatgtt gatcattgca ccgttctcag ttctcggtcg atcggatctt gtagatcggt    60
gcggtgcgac cctctacgta gtgcacgtat gcgtccatct ttacagtcc               109

<210> SEQ ID NO 42
```

-continued

```
<211> LENGTH: 102
<212> TYPE: DNA
<213> ORGANISM: Artificial Sequence
<220> FEATURE:
<223> OTHER INFORMATION: Primer KB518-266-135

<400> SEQUENCE: 42
aagatccgat cgaccgagaa ctgagaacgg tgcaatgatc aacatgatct tatgtcgggt     60
gcggagaaag aggtaatgaa agttcatcat ctcatggatc tg                       102

<210> SEQ ID NO 43
<211> LENGTH: 101
<212> TYPE: DNA
<213> ORGANISM: Artificial Sequence
<220> FEATURE:
<223> OTHER INFORMATION: Primer KB519-266-135

<400> SEQUENCE: 43
agatcatgtt gatcattgca ccgttctcag ttctcggtcg atcggatctt tttcattacc     60
tctttctccg cacccgacat aatgcgtcca tctttacagt c                        101

<210> SEQ ID NO 44
<211> LENGTH: 23
<212> TYPE: DNA
<213> ORGANISM: Artificial Sequence
<220> FEATURE:
<223> OTHER INFORMATION: Primer KB496-266-100

<400> SEQUENCE: 44
ccaacaataa taatgtcaga tcc                                            23

<210> SEQ ID NO 45
<211> LENGTH: 19
<212> TYPE: DNA
<213> ORGANISM: Artificial Sequence
<220> FEATURE:
<223> OTHER INFORMATION: Primer KB495-266-100

<400> SEQUENCE: 45
ccgagcagaa ggaagaacg                                                 19

<210> SEQ ID NO 46
<211> LENGTH: 1504
<212> TYPE: DNA
<213> ORGANISM: Artificial Sequence
<220> FEATURE:
<223> OTHER INFORMATION: RaBit12-0-M-262

<400> SEQUENCE: 46
gctcacacgc ggccaggggg agcctcgaca ctagtaatac acatcatcgt cctacaagtt     60
catcaaagtg ttggacagac aactatacca gcatggatct cttgtatcgg ttcttttctc    120
ccgctctctc gcaataacaa tgaacactgg gtcaatcata gcctacacag gtgaacagag    180
tagcgtttat acagggttta tacggtgatt cctacggcaa aaattttca tttctaaaaa     240 aaaaaagaaa aattttctct tccaacgcta gaaggaaaag aaaaatctaa ttaaattgat    300
ttggtgattt tctgagagtt ccctttttca tatatcgaat tttgaatata aaaggagatc    360
gaaaaaattt ttctattcaa tctgttttct ggttttattt gatagttttt ttgtgtatta    420
ttattatgga ttagtactgg tttatatggg ttttttctgta aacttctttt ttattttagt    480
ttgtttaatc ttatttttgag ttacattata gttccctaac tgcaagagaa gtaacattaa    540
aaatgaccac tcttgacgac acggcttacc ggtaccgcac cagtgtcccg ggggacgccg    600
```

```
aggccatcga ggcactggat gggtccttca ccaccgacac cgtcttccgc gtcaccgcca    660
ccggggacgg cttcaccctg cgggaggtgc cggtggaccc gccctgacc aaggtgttcc     720 ccgacgacga atcggacgac gaatcggacg ccggggagga cggcgacccg gactcccgga    780
cgttcgtcgc gtacggggac gacggcgacc tggcgggctt cgtggtcgtc tcgtactccg    840
gctggaaccg ccggctgacc gtcgaggaca tcgaggtcgc cccggagcac cgggggcacg    900
gggtcgggcg cgcgttgatg gggctcgcga cggagttcgc ccgcgagcgg ggcgccgggc    960
acctctggct ggaggtcacc aacgtcaacg caccggcgat ccacgcgtac cggcggatgg   1020
ggttcaccct ctgcggcctg acaccgccc tgtacgacgg caccgcctcg acggcgagc    1080 aggcgctcta catgagcatg ccctgccct gagtttaact tgatactact agatttttc    1140 tcttcattta taaattttt ggttataatt gaagctttag aagtatgaaa aaatcctttt    1200
ttttcattct ttgcaaccaa ataagaagc ttctttat cattgaaatg atgaatataa     1260
acctaacaaa agaaaagac tcgaatatca aacattaaaa aaaaataaaa gaggttatct    1320
gttttcccat ttagttggag tttgcatttt ctaatagata gaactctcaa ttaatgtgga   1380
tttagtttct ctgttcgttt tttttgttt tgttctcact gtatttacat ttctatttag    1440
tatttagtta ttcatataat cttaacttct cgaggagctc cgctcgtcca acgccggcgg   1500
acct                                                                1504
```

<210> SEQ ID NO 47
<211> LENGTH: 97
<212> TYPE: DNA
<213> ORGANISM: Artificial Sequence
<220> FEATURE:
<223> OTHER INFORMATION: Primer MF51-312-97

<400> SEQUENCE: 47

```
cgttacgaag cacacactag ttagcgtcga gacacatagc gacgctagaa gatgcacgag    60
cgcaacgctc acaatcgaca ctagtaatac acatcat                            97
```

<210> SEQ ID NO 48
<211> LENGTH: 94
<212> TYPE: DNA
<213> ORGANISM: Artificial Sequence
<220> FEATURE:
<223> OTHER INFORMATION: Primer MF52-312-97

<400> SEQUENCE: 48

```
ttctagcgtc gctatgtgtc tcgacgctaa ctagtgtgtg cttcgtaacg ttgtgagcgt    60
tgcgctcgtg catcgagctc ctcgagaagt taag                               94
```

<210> SEQ ID NO 49
<211> LENGTH: 97
<212> TYPE: DNA
<213> ORGANISM: Artificial Sequence
<220> FEATURE:
<223> OTHER INFORMATION: Primer MF57-312-98

<400> SEQUENCE: 49

```
ttaatcagcg cccagagact agcactgaat gatcaacggg tagttcacac gatgcacgag    60
cgcaacgctc acaatcgaca ctagtaatac acatcat                            97
```

<210> SEQ ID NO 50
<211> LENGTH: 94
<212> TYPE: DNA

```
<213> ORGANISM: Artificial Sequence
<220> FEATURE:
<223> OTHER INFORMATION: Primer MF58-312-98

<400> SEQUENCE: 50
gtgtgaacta cccgttgatc attcagtgct agtctctggg cgctgattaa ttgtgagcgt      60
tgcgctcgtg catcgagctc ctcgagaagt taag                                  94

<210> SEQ ID NO 51
<211> LENGTH: 17
<212> TYPE: DNA
<213> ORGANISM: Artificial Sequence
<220> FEATURE:
<223> OTHER INFORMATION: Primer KB479-266-81

<400> SEQUENCE: 51
cgtccgattc gtcgtcg                                                     17

<210> SEQ ID NO 52
<211> LENGTH: 16
<212> TYPE: DNA
<213> ORGANISM: Artificial Sequence
<220> FEATURE:
<223> OTHER INFORMATION: Primer KB480-266-81

<400> SEQUENCE: 52
gaggtgccgg tggacc                                                      16

<210> SEQ ID NO 53
<211> LENGTH: 1960
<212> TYPE: DNA
<213> ORGANISM: Artificial Sequence
<220> FEATURE:
<223> OTHER INFORMATION: RaBit12-0-M-21

<400> SEQUENCE: 53
gctcacacgc ggccaggggg agcctcgaca ctagtaatac acatcatcgt cctacaagtt      60
catcaaagtg ttggacagac aactatacca gcatggatct cttgtatcgg ttcttttctc     120
ccgctctctc gcaataacaa tgaacactgg gtcaatcata gcctacacag gtgaacagag     180
tagcgtttat acagggttta tacggtgatt cctacggcaa aaattttca tttctaaaaa      240 aaaaaagaaa aattttctt tccaacgcta gaaggaaaag aaaaatctaa ttaaattgat      300
ttggtgattt tctgagagtt cccttttca tatatcgaat tttgaatata aaaggagatc      360 gaaaaattt ttctattcaa tctgttttct ggttttattt gatagttttt ttgtgtatta     420
ttattatgga ttagtactgg tttatatggg tttttctgta taacttcttt ttattttagt     480
ttgtttaatc ttattttgag ttacattata gttccctaac tgcaagagaa gtaacattaa    540
aaatgaaaaa gcctgaactc accgcgacgt ctgtcgagaa gtttctgatc gaaaagttcg    600
acagcgtctc cgacctgatg cagctctcgg agggcgaaga atctcgtgct ttcagcttcg    660
atgtaggagg gcgtggatat gtcctgcggg taaatagctg cgccgatggt ttctacaaag    720
atcgttatgt ttatcggcac tttgcatcgg ccgcgctccc gattccggaa gtgcttgaca    780
ttggggaatt cagcgagagc ctgacctatt gcatctcccg ccgtgcacag ggtgtcacgt    840
tgcaagacct gcctgaaacc gaactgcccg ctgttctgca gccggtcgcg gaggccatgg    900
atgcgatcgc tgcggccgat cttagccaga cgagcgggtt cggcccattc ggaccgcaag    960
gaatcggtca atacactaca tggcgtgatt tcatatgcgc gattgctgat ccccatgtgt   1020
atcactggca aactgtgatg gacgacaccg tcagtgcgtc cgtcgcgcag gctctcgatg   1080
```

```
agctgatgct ttgggccgag gactgccccg aagtccggca cctcgtgcac gcggatttcg    1140
gctccaacaa tgtcctgacg gacaatggcc gcataacagc ggtcattgac tggagcgagg    1200
cgatgttcgg ggattcccaa tacgaggtcg ccaacatctt cttctggagg ccgtggttgg    1260
cttgtatgga gcagcagacg cgctacttcg agcggaggca tccggagctt gcaggatcgc    1320
cgcggctccg ggcgtatatg ctccgcattg gtcttgacca actctatcag agcttggttg    1380
acggcaattt cgatgatgca gcttgggcgc agggtcgatg cgacgcaatc gtccgatccg    1440
gagccgggac tgtcgggcgt acacaaatcg cccgcagaag cgcggccgtc tggaccgatg    1500
gctgtgtaga agtactcgcc gatagtggaa accgacgccc cagcactcgt ccagggcaa     1560 aggaataggt ttaacttgat actactagat ttttctctt catttataaa attttggtt      1620 ataattgaag cttagaagt atgaaaaaat ccttttttt cattctttgc aaccaaaata      1680
agaagcttct tttattcatt gaatgatga atataaacct aacaaagaa aaagactcga      1740 atatcaaaca ttaaaaaaaa ataaaagagg ttatctgttt tcccatttag ttggagtttg    1800
cattttctaa tagatagaac tctcaattaa tgtggattta gtttctctgt tcgtttttt     1860 ttgtttgtt ctcactgtat ttacatttct atttagtatt tagttattca tataatctta    1920
acttctcgag gagctccgct cgtccaacgc cggcggacct                           1960
```

```
<210> SEQ ID NO 54
<211> LENGTH: 97
<212> TYPE: DNA
<213> ORGANISM: Artificial Sequence
<220> FEATURE:
<223> OTHER INFORMATION: Primer MF53-312-98

<400> SEQUENCE: 54
gtactgccta gtagaaacgg atctccacgt actagagtcc acctggtatc gatgcacgag    60
cgcaacgctc acaatcgaca ctagtaatac acatcat                             97

<210> SEQ ID NO 55
<211> LENGTH: 94
<212> TYPE: DNA
<213> ORGANISM: Artificial Sequence
<220> FEATURE:
<223> OTHER INFORMATION: Primer MF54-312-98

<400> SEQUENCE: 55
gataccaggt ggactctagt acgtggagat ccgtttctac taggcagtac ttgtgagcgt    60
tgcgctcgtg catcgagctc ctcgagaagt taag                                94

<210> SEQ ID NO 56
<211> LENGTH: 16
<212> TYPE: DNA
<213> ORGANISM: Artificial Sequence
<220> FEATURE:
<223> OTHER INFORMATION: Primer KB492-266-100

<400> SEQUENCE: 56
gccgaaatcc gcgtgc                                                    16

<210> SEQ ID NO 57
<211> LENGTH: 19
<212> TYPE: DNA
<213> ORGANISM: Artificial Sequence
<220> FEATURE:
<223> OTHER INFORMATION: Primer KB491-266-100
```

```
<400> SEQUENCE: 57
cggaagtgct tgacattgg                                                  19

<210> SEQ ID NO 58
<211> LENGTH: 1744
<212> TYPE: DNA
<213> ORGANISM: Artificial Sequence
<220> FEATURE:
<223> OTHER INFORMATION: RaBit 12-0-M-261

<400> SEQUENCE: 58
gctcacacgc ggccagggggg agcctcgaca ctagtaatac acatcatcgt cctacaagtt     60
catcaaagtg ttggacagac aactatacca gcatggatct cttgtatcgg ttcttttctc    120
ccgctctctc gcaataacaa tgaacactgg gtcaatcata gcctacacag gtgaacagag    180
tagcgtttat acagggttta tacggtgatt cctacggcaa aaattttttca tttctaaaaa    240 aaaaaagaaa aattttttctt tccaacgcta gaaggaaaag aaaaatctaa ttaaattgat    300
ttggtgattt tctgagagtt cccttttttca tatatcgaat tttgaatata aaaggagatc    360
gaaaaaattt ttctattcaa tctgttttct ggttttattt gatagttttt ttgtgtatta    420
ttattatgga ttagtactgg tttatatggg ttttttctgta taacttcttt ttatttttagt    480 ttgtttaatc ttattttgag ttacattata gttccctaac tgcaagagaa gtaacattaa    540
aaatgggtaa ggaaaagact cacgtttcga ggccgcgatt aaattccaac atggatgctg    600
atttatatgg gtataaatgg gctcgcgata atgtcgggca atcaggtgcg acaatctatc    660
gattgtatgg gaagcccgat gcgccagagt tgtttctgaa acatggcaaa ggtagcgttg    720
ccaatgatgt tacagatgag atggtcagac taaactggct gacggaattt atgcctcttc    780
cgaccatcaa gcattttatc cgtactcctg atgatgcatg gttactcacc actgcgatcc    840
ccggcaaaac agcattccag gtattagaag aatatcctga ttcaggtgaa atattgttg    900 atgcgctggc agtgttcctg cgccggttgc attcgattcc tgtttgtaat tgtccttttta    960 acagcgatcg cgtatttcgt ctcgctcagg cgcaatcacg aatgaataac ggtttggttg   1020
atgcgagtga ttttgatgac gagcgtaatg gctggcctgt tgaacaagtc tggaaagaaa   1080
tgcataagct tttgccattc tcaccggatt cagtcgtcac tcatggtgat ttctcacttg   1140
ataaccttat ttttgacgag gggaaattaa taggttgtat tgatgttgga cgagtcggaa   1200
tcgcagaccg ataccaggat cttgccatcc tatggaactg cctcggtgag ttttctcctt   1260
cattacagaa acggcttttt caaaaatatg gtattgataa tcctgatatg aataaattgc   1320
agtttcattt gatgctcgat gagttttttct aagtttaact tgatactact agattttttc   1380
tcttcattta taaaattttt ggttataatt gaagctttag aagtatgaaa aaatcctttt   1440
ttttcattct ttgcaaccaa aataagaagc ttctttttatt cattgaaatg atgaatataa   1500
acctaacaaa agaaaaagac tcgaatatca aacattaaaa aaaaataaaa gaggttatct   1560
gttttcccat ttagttggag tttgcatttt ctaatagata gaactctcaa ttaatgtgga   1620
tttagtttct ctgttcgttt tttttttgttt tgttctcact gtatttacat ttctatttag   1680
tatttagtta tcatataat cttaacttct cgaggagctc cgctcgtcca acgccggcgg   1740
acct                                                                1744

<210> SEQ ID NO 59
<211> LENGTH: 102
<212> TYPE: DNA
<213> ORGANISM: Artificial Sequence
```

<220> FEATURE:
<223> OTHER INFORMATION: Primer TD_180

<400> SEQUENCE: 59
cgaggattaa cgtgtaaggc cctaagctat gtaccgcatc tcctaagaga gatgcacgag    60
cgcaacgctc acaatcgaca ctagtaatac acatcatcgt cc                      102

<210> SEQ ID NO 60
<211> LENGTH: 102
<212> TYPE: DNA
<213> ORGANISM: Artificial Sequence
<220> FEATURE:
<223> OTHER INFORMATION: Primer TD_181

<400> SEQUENCE: 60
tctcttagga gatgcggtac atagcttagg gccttacacg ttaatcctcg ttgtgagcgt    60
tgcgctcgtg catcgagctc ctcgagaagt taagattata tg                      102

<210> SEQ ID NO 61
<211> LENGTH: 24
<212> TYPE: DNA
<213> ORGANISM: Artificial Sequence
<220> FEATURE:
<223> OTHER INFORMATION: Primer KB494-266-100

<400> SEQUENCE: 61
tatctattag aaaatgcaaa ctcc                                          24

<210> SEQ ID NO 62
<211> LENGTH: 20
<212> TYPE: DNA
<213> ORGANISM: Artificial Sequence
<220> FEATURE:
<223> OTHER INFORMATION: Primer KB493-266-100

<400> SEQUENCE: 62
gttactcacc actgcgatcc                                               20

<210> SEQ ID NO 63
<211> LENGTH: 429
<212> TYPE: DNA
<213> ORGANISM: Artificial Sequence
<220> FEATURE:
<223> OTHER INFORMATION: coding sequence for F-CphI

<400> SEQUENCE: 63
atgactaagt tgtattctga cttgtacagg acctgcatga catgcggaga agaaaaattg    60
tcaaccgagt tctacgtcag gaacaagaag accggagtta gacattcatc atgcaaagag    120
tgtgacaagg tcagggtcaa atcaagacac aaggagaacc ctgaaaggac caaaaacaac    180
gacttgaaga gattgtacgg aatcaccttg gacgagcata cccaaatgta tgaggaacaa    240
aatggtgtat gtgcaatttg caagggagaa ggagatggaa agtggaagaa attgtgtgtt    300
gaccatgatc acgaaacagg aaaggtcagg cagttgttgt gtaggaactg caatatgatg    360
ttgggtcagg tcaacgacaa cgttaactta ttatcagaaa tgataaagta tttgaaaaga 420
tatcagtaa 429

<210> SEQ ID NO 64
<211> LENGTH: 103
<212> TYPE: DNA
<213> ORGANISM: Artificial Sequence
<220> FEATURE:

<223> OTHER INFORMATION: Primer TD_176

<400> SEQUENCE: 64
gtcaaagcgc gattcgctag gaatgagagc gagaacgaac cggagtatat gatgcacgag    60
cgcaacgctc acaaaataca catcatcgtc ctacaagttc atc                      103

<210> SEQ ID NO 65
<211> LENGTH: 103
<212> TYPE: DNA
<213> ORGANISM: Artificial Sequence
<220> FEATURE:
<223> OTHER INFORMATION: Primer TD_177

<400> SEQUENCE: 65
atatactccg gttcgttctc gctctcattc ctagcgaatc gcgctttgac ttgtgagcgt    60
tgcgctcgtg catcaagtta agattatatg aataactaaa tac                      103

<210> SEQ ID NO 66
<211> LENGTH: 24
<212> TYPE: DNA
<213> ORGANISM: Artificial Sequence
<220> FEATURE:
<223> OTHER INFORMATION: Primer TD_183

<400> SEQUENCE: 66
tcggccacga agtgcacgca gttg                                            24

<210> SEQ ID NO 67
<211> LENGTH: 24
<212> TYPE: DNA
<213> ORGANISM: Artificial Sequence
<220> FEATURE:
<223> OTHER INFORMATION: Primer TD_182

<400> SEQUENCE: 67
tcgagttctg gaccgaccgg ctcg                                            24

<210> SEQ ID NO 68
<211> LENGTH: 28
<212> TYPE: DNA
<213> ORGANISM: Artificial Sequence
<220> FEATURE:
<223> OTHER INFORMATION: Primer RYSE0

<400> SEQUENCE: 68
gacggcacgg ccacgcgttt aaaccgcc                                        28

<210> SEQ ID NO 69
<211> LENGTH: 28
<212> TYPE: DNA
<213> ORGANISM: Artificial Sequence
<220> FEATURE:
<223> OTHER INFORMATION: Primer RYSE19

<400> SEQUENCE: 69
cggtgtttaa accccagcgc ctggcggg                                        28

<210> SEQ ID NO 70
<211> LENGTH: 598
<212> TYPE: DNA
<213> ORGANISM: Artificial Sequence
<220> FEATURE:
<223> OTHER INFORMATION: RaBit01-0-U-407

<400> SEQUENCE: 70

```
gacggcacgg ccacgcgttt aaaccgccga gctattcgcg gaacattcta gctcgtttgc      60
atcttcttgc atttggtagg ttttcaatag ttcggtaata ttaacggata cctactatta     120 tccctagta ggctcttttc acggagaaat tcgggagtgt tttttttccg tgcgcatttt      180
cttagctata ttcttccagc ttcgcctgct gcccggtcat cgttcctgtc acgtagtttt    240
tccggattcg tccggctcat ataataccgc aataaacacg gaatatctcg ttccgcggat    300
tcggttaaac tctcggtcgc ggattatcac agagaaagct tcgtggagaa ttttccaga     360 ttttccgctt tccccgatgt tggtatttcc ggaggtcatt atactgaccg ccattataat    420
gactgtacaa cgaccttctg gagaaagaaa caactcaata acgatgtggg acattggggg   480
cccactcaaa aaatctgggg actatatccc cagagaattt ctccagaaga gaagaaaagt    540
caaagttttt tttcgcttgg gggttgcata taaagctcac acgcggccag ggggagcc     598

<210> SEQ ID NO 71
<211> LENGTH: 574
<212> TYPE: DNA
<213> ORGANISM: Artificial Sequence
<220> FEATURE:
<223> OTHER INFORMATION: RaBit29-0-D-408

<400> SEQUENCE: 71
cgctcgtcca acgccggcgg acctaataaa agacattggt acatgatatc aaacagaatt     60
ttaacatttc ttgatccagt ttgtaaacaa acaaacaat ttttctacca tttaacttca   120
taccatcggc gagagccgaa caggaaaaaa aagaagtctc cggttatcgt aagcagtatc   180
aaataataag aatgtatgtg tgtgcaattt gttatacccca cgaagaagtg cgcagtagag    240
ttagaaaacc aactgagtaa tctttactcc cgacaatcgt ccaataatcc tcttgttgct    300
aggaacgtga tgatggattt cgtttgaaat ccggacggaa aactcaaaag aagtccaacc    360
accaaccatt ttcgagcctc aagaatctct aagcaggttt ctttactaag gggatggcct    420
ttctgtcctg gacattttt ccttccttt ttcatttcct tgaaaggaac agattttttt       480
tgacttttgc cacacagctg cactatctca accccttta cattttaagt tttcgggttg     540
aatggccggt gtttaaaccc cagcgcctgg cggg                                 574

<210> SEQ ID NO 72
<211> LENGTH: 668
<212> TYPE: DNA
<213> ORGANISM: Artificial Sequence
<220> FEATURE:
<223> OTHER INFORMATION: RaBit23-0-P-39

<400> SEQUENCE: 72
cgctcgtcca acgccggcgg accttacttt ttttttggat ggacgcaaag aagtttaata     60
atcatattac atggcattac caccatatac atatccatat ctaatcttac ttatatgttg   120
tggaaatgta aagagcccca ttatcttagc ctaaaaaaac cttctctttg gaactttcag    180
taatacgctt aactgctcat tgctatattg aagtacggat tagaagccgc cgagcgggcg    240
acagccctcc gacggaagac tctcctccgt gcgtcctcgt cttcaccggt cgcgttcctg    300
aaacgcagat gtgcctcgcg ccgcactgct ccgaacaata aagattctac aatactagct    360
tttatggtta tgaagaggaa aaattggcag taacctggcc ccacaaacct tcaaattaac    420
gaatcaaatt aacaaccata ggatgataat gcgattagtt ttttagcctt atttctgggg    480
taattaatca gcgaagcgat gatttttgat ctattaacag atatataaat ggaaaagctg    540
```

```
cataaccact ttaactaata cttttcaacat tttcagtttg tattacttct tattcaaatg    600
tcataaaagt atcaacaaaa aattgttaat atacctctat acttatcccc gcgtgcttgg    660
ccggccgt                                                              668

<210> SEQ ID NO 73
<211> LENGTH: 311
<212> TYPE: DNA
<213> ORGANISM: Artificial Sequence
<220> FEATURE:
<223> OTHER INFORMATION: RaBit45-0-T-64

<400> SEQUENCE: 73
aacctgcagg ccgcgagcgc cgattaagtg aatttacttt aaatcttgca tttaaataaa     60
ttttcttttt atagctttat gacttagttt caatttatat actattttaa tgacattttc    120
gattcattga ttgaaagctt tgtgtttttt cttgatgcgc tattgcattg ttcttgtctt    180
tttcgccaca tgtaatatct gtagtagata cctgatacat tgtggatgct gagtgaaatt    240
ttagttaata atggaggcgc tcttaataat tttggggata ttggcttaac gcgatcgccg    300
acgccgccga t                                                          311

<210> SEQ ID NO 74
<211> LENGTH: 24
<212> TYPE: DNA
<213> ORGANISM: Artificial Sequence
<220> FEATURE:
<223> OTHER INFORMATION: Primer RYSE4

<400> SEQUENCE: 74
cgctcgtcca acgccggcgg acct                                             24

<210> SEQ ID NO 75
<211> LENGTH: 24
<212> TYPE: DNA
<213> ORGANISM: Artificial Sequence
<220> FEATURE:
<223> OTHER INFORMATION: Primer RYSE11

<400> SEQUENCE: 75
atcggcggcg tcggcgatcg cgtt                                             24

<210> SEQ ID NO 76
<211> LENGTH: 547
<212> TYPE: DNA
<213> ORGANISM: Artificial Sequence
<220> FEATURE:
<223> OTHER INFORMATION: RaBit01-0-U-97

<400> SEQUENCE: 76
gacggcacgg ccacgcgttt aaaccgccct ccaagctgac ataaatcgca ctttgtatct     60 acttttttt attcgaaaac aaggcacaac aatgaatcta tcgccctgtg agattttcaa    120
tctcaagttt gtgtaataga tagcgttata ttatagaact ataaaggtcc ttgaatatac    180
atagtgtttc attcctatta ctgtatatgt gactttacat tgttacttcc gcggctattt    240
gacgttttct gcttcaggtg cggcttggag ggcaaagtgt cagaaaatcg ccaggccgt    300 atgacacaaa agagtagaaa acgagatctc aaatatctcg aggcctgtcc tctatacaac    360
cgcccagctc tctgacaaag ctccagaacg gttgtctttt gtttcgaaaa gccaaggtcc    420
cttataattg ccctccattt tgtgtcacct atttaagcaa aaaattgaaa gtttactaac    480
ctttcattaa agagaaataa caatattata aaaagcgctt aaagctcaca cgcggccagg    540
```

```
<210> SEQ ID NO 77
<211> LENGTH: 568
<212> TYPE: DNA
<213> ORGANISM: Artificial Sequence
<220> FEATURE:
<223> OTHER INFORMATION: RaBit29-0-D-23

<400> SEQUENCE: 77
cgctcgtcca acgccggcgg acctataaac taatgatttt aaatcgttaa aaaaatatgc    60
gaattctgtg gatcgaacac aggacctcca gataacttga ccgaagtttt ttcttcagtc   120
tggcgctctc ccaactgagc taaatccgct tactatttgt tatcagttcc cttcatatct   180
acatagaata ggttaagtat tttattagtt gccagaagaa ctactgatag ttgggaatat   240
ttggtgaata atgaagattg ggtgaataat ttgataattt tgagattcaa ttgttaatca   300
atgttacaat attatgtata cagagtatac tagaagttct cttcggagat cttgaagttc   360
acaaaaggga atcgatattt ctacataata ttatcattac ttcttcccca tcttatattt   420
gtcattcatt attgattatg atcaatgcaa taatgattgg tagttgccaa acatttaata   480
cgatcctctg taatatttct atgaataatt atcacagcaa cgttcaatta tcttcaattc   540
cggtgtttaa accccagcgc ctggcggg                                       568

<210> SEQ ID NO 78
<211> LENGTH: 552
<212> TYPE: DNA
<213> ORGANISM: Artificial Sequence
<220> FEATURE:
<223> OTHER INFORMATION: RaBit01-0-U-270

<400> SEQUENCE: 78
gacggcacgg ccacgcgttt aaaccgccca gatggaatcc cttccataga gagaaggagc    60
aagcaactga cccaatattg actgccactg gacctgaaga catgcaacaa agtgcaagca   120
tagtggggcc ttcttccaat gctaatccgg tcactgccac tgctgctacg gaaaaccaac   180
ctaaaggtat taacttcttc actataagaa atcacacga gcgcccggac gatgtctctg   240
tttaaatggc gcaagttttc cgctttgtaa tatatattta tacccctttc ttctctcccc   300
tgcaatataa tagtttaatt ctaatattaa taatatccta tattttcttc atttaccggc   360
gcactctcgc ccgaacgacc tcaaaatgtc tgctacattc ataataacca aaagctcata   420
acttttttt ttgaacctga atatatatac atcacatatc actgctggtc cttgccgacc   480
agcgtataca atctcgatag ttggtttccc gttctttcca ctcccgtcgc tcacacgcgg   540
ccaggggag cc                                                         552

<210> SEQ ID NO 79
<211> LENGTH: 561
<212> TYPE: DNA
<213> ORGANISM: Artificial Sequence
<220> FEATURE:
<223> OTHER INFORMATION: RaBit29-0-D-95

<400> SEQUENCE: 79
cgctcgtcca acgccggcgg acctcgtgca tgcgggtgtt cttatttatt agcatactac    60
atttgaaata tcaaatttcc ttagtagaaa agtgagagaa ggtgcactga cacaaaaaat   120
aaaatgctac gtataactgt caaaactttg cagcagcggg catccttcca tcatagcttc   180
```

| | |
|---|---|
| aaacatatta gcgttcctga tcttcatacc cgtgctcaaa atgatcaaac aaactgttat | 240 |
| tgccaagaaa taaacgcaag gctgccttca aaaactgatc cattagatcc tcatatcaag | 300 |
| cttcctcata gaacgcccaa ttacaataag catgttttgc tgttatcacc gggtgatagg | 360 |
| tttgctcaac catggaaggt agcatggaat cataatttgg atactaatac aaatcggcca | 420 |
| tataatgcca ttagtaaatt gcgctcccat ttaggtggtt ctccaggaat actaataaat | 480 |
| gcggtgcatt tgcaaaatga atttattcca aggccaaaac aacacgatga atgcggtgtt | 540 |
| taaaccccag cgcctggcgg g | 561 |

<210> SEQ ID NO 80
<211> LENGTH: 1179
<212> TYPE: DNA
<213> ORGANISM: Artificial Sequence
<220> FEATURE:
<223> OTHER INFORMATION: Coding sequence for PI-MgaI(pps1) with
    N-terminal SV40 NLS

<400> SEQUENCE: 80

| | |
|---|---|
| atgttaattt ctccaaagaa gaagaggaag gtcgagttgg gatgtttagc aggtgatacc | 60 |
| ttggtttgga ccgccaatag aggacaggtc ccaatcaagg agatagagtt cggtgacagg | 120 |
| gtcttctctt acgacgaatc agcagagaga ttcgtagttg ccccagtaaa agcatctgct | 180 |
| caaacagaca ccaggttaac ctacgaggta aagactacca aaggtcagt tagggctact | 240 |
| gacaaccacc caatgttggt cttgagggat gaaaggaagg agggtagaca aagagccagg | 300 |
| tatgctagga gatgggtaac agtaggacag ataaagcctg tgactttat cgctgttcca | 360 |
| agagctgtac caaacttcgg agtcgctgag cagttgcctt cagtcgccgg tttgaccaca | 420 |
| ccagccacct catcagcaga tttgatgtgg ttattgggat tgtacgtcgg agacggaaac | 480 |
| ttgcacttgt caaccaagac ctatagggta caatttgcta tacctgcaac cgatagagag | 540 |
| ttaagggccg agttgactag agttatcaag gacttgttcg gattgagtg cattgaggca | 600 |
| gatgagtaca gggttgtcgt caattcaaag gcattaaccg aatggatcgc agctttgggt | 660 |
| tttggaggtt tgtcattgac aaaaagagtc ccagactggg tttatggatt gccagtcgat | 720 |
| caaagattgg cattcttagg tggatgggta gatgccgatg gttatgtctc tccagacaaa | 780 |
| tcaggttcaa ttttattgac atgtgccaat caggccttga taggtcaggc cagggaatta | 840 |
| gctgagttag ctggtttgag ggctggaggt ccttggtcat tcactcaacc ttacagacat | 900 |
| gcaccagaca ggatgcaaat tgcatggagg ttgggtatct ctggtgattt cgagagattg | 960 |
| ggttgtagga acccaaagag aaccgacagg ttcggtagga aaggtacat gcattcatct | 1020 |
| tcaggtgccc acggaaccac cattagggcc cactgcaacg attggttggg atttgagagg | 1080 |
| gtcaaagcag tcgagccata tgcagttgag cctgtatacg acatcgaggt tgacggtcca | 1140 |
| cacaacttcg tcgcagaggg attagtagtt cataactaa | 1179 |

<210> SEQ ID NO 81
<211> LENGTH: 1122
<212> TYPE: DNA
<213> ORGANISM: Artificial Sequence
<220> FEATURE:
<223> OTHER INFORMATION: Coding sequence for PI-MtuII(pps1) with
    N-terminal SV40 NLS

<400> SEQUENCE: 81

| | |
|---|---|
| atgttgatct caccaaagaa gaagagaaaa gtcgagttgg gttgcttacc tgctggagag | 60 |
| ttaataacta cagccgacgg tgacttgagg cctatcgagt ctataagggt aggagacttc | 120 |

```
gttacaggtc acgatggtag gccacacaga gtcacagcag ttcaggtcag agatttagat      180
ggagaattgt tcactttcac ccctatgtct cctgctaacg cattttctgt taccgccgaa      240
catcctttat tagcaatccc tagggacgaa gtcagggtta tgaggaagga gaggaatggt      300
tggaaggctg aagtcaactc taccaaatta agatctgcag agccaaggtg gatcgcagct      360
aaagatgttg ccgagggtga tttcttgatc taccctaaac caaagcctat ccctcacagg      420
accgtattgc cattggagtt cgctaggttg gctggatact acttagcaga aggtcatgct      480
tgtttaacca acggatgcga gtctttaatc ttctcattcc actctgatga atttgaatac      540
gtagaggacg ttaggcaagc ctgtaaatca ttatacgaaa agtctggatc agtcttgatc      600
gaggagcata aacactcagc aagggtaacc gtctacacta agctggata  tgctgccatg      660 agggacaacg tcggtatagg ttcttcaaat aaaaagttat cagacttgtt aatgaggcag      720
gacgaaacct ttttgaggga gttggttgac gcatatgtta acggagatgg aaacgtaacc      780
agaaggaatg gagcagtttg gaaagggtc  cacacaacat caaggttgtg ggcatttcaa      840
ttacagtcaa ttttggcaag attgggtcat tacgcaaccg tagaattaag gagaccaggt      900
ggtccaggtg taataatggg taggaacgtt gttaggaaag acatctacca ggtacagtgg      960
accgagggag gtaggggtcc aaagcaggca agggactgcg gagattactt cgcagttcca     1020
atcaagaaga gagctgttag ggaagcccac gagccagtct acaacttgga cgtcgaaaac     1080
ccagactcat acttggccta tggttttgca gtccataact aa                       1122
```

<210> SEQ ID NO 82
<211> LENGTH: 708
<212> TYPE: DNA
<213> ORGANISM: Artificial Sequence
<220> FEATURE:
<223> OTHER INFORMATION: Coding sequence for I-SceI

<400> SEQUENCE: 82

```
atgaagaaca tcaagaagaa ccaggtcatg aatctgggtc ctaactctaa attattgaaa       60
gaatataaga gccaacttat cgaactaaac attgaacaat ttgaggctgg aataggttta      120
attttaggtg atgcgtacat taggtccaga gatgagggta aaacatactg tatgcagttt      180
gagtggaaaa ataaagccta tatggatcat gtttgtttgc tgtatgatca atgggtatta      240
tctcctcctc ataagaaaga aagagttaat cacctaggga atttagtgat aacgtgggga      300
gcacagactt ttaagcacca agcgttcaac aaattagcaa atttgtttat tgtcaataat      360
aagaaaacaa ttcctaataa tttggtggaa aactacctaa ctccaatgtc tttagcatat      420
tggttcatgg atgacggtgg aaaatgggat tacaacaaaa acagcacaaa caaatctata      480
gtgctaaata cgcaaagttt tacttttgaa gaagtagaat acttagttaa aggattgcgt      540
aacaagtttc aacttaattg ttatgttaag attaataaaa ataaaccgat catttacata      600
gattctatgt catatttaat attctacaat cttattaaac cttatttaat tccgcaaatg      660
atgtataaac tgccaaatac catatcttcc gagacgttcc tcaagtag                   708
```

<210> SEQ ID NO 83
<211> LENGTH: 36
<212> TYPE: DNA
<213> ORGANISM: Artificial Sequence
<220> FEATURE:
<223> OTHER INFORMATION: Primer KB510-266-134

<400> SEQUENCE: 83
ctgagctcta aatataaaca ttaaatacat tacacg                              36

<210> SEQ ID NO 84
<211> LENGTH: 32
<212> TYPE: DNA
<213> ORGANISM: Artificial Sequence
<220> FEATURE:
<223> OTHER INFORMATION: Primer KB511-266-134

<400> SEQUENCE: 84
gactcgaggc tcaaaagaag actaactaag ag                                  32

<210> SEQ ID NO 85
<211> LENGTH: 55
<212> TYPE: DNA
<213> ORGANISM: Artificial Sequence
<220> FEATURE:
<223> OTHER INFORMATION: Primer KB512-266-134

<400> SEQUENCE: 85
aattcgacct ttctcttctt ttttggagag attgtcatat tttattattg tattg         55

<210> SEQ ID NO 86
<211> LENGTH: 48
<212> TYPE: DNA
<213> ORGANISM: Artificial Sequence
<220> FEATURE:
<223> OTHER INFORMATION: Primer KB513-266-134

<400> SEQUENCE: 86
caaaaaagaa gagaaaggtc gaattaggtt ttgccaaggg taccaatg                 48

<210> SEQ ID NO 87
<211> LENGTH: 44
<212> TYPE: DNA
<213> ORGANISM: Artificial Sequence
<220> FEATURE:
<223> OTHER INFORMATION: Primer KB514-266-134

<400> SEQUENCE: 87
ggttgtcgtc cataattgct gaaagatttt tgtagttttt gtat                     44

<210> SEQ ID NO 88
<211> LENGTH: 44
<212> TYPE: DNA
<213> ORGANISM: Artificial Sequence
<220> FEATURE:
<223> OTHER INFORMATION: Primer KB515-266-134

<400> SEQUENCE: 88
atacaaaaac tacaaaaatc tttcagcaat tatggacgac aacc                     44

<210> SEQ ID NO 89
<211> LENGTH: 1700
<212> TYPE: DNA
<213> ORGANISM: Artificial Sequence
<220> FEATURE:
<223> OTHER INFORMATION: xMarker xM0.URA.F-CphI

<400> SEQUENCE: 89
aagatccgat cgaccgagaa ctgagaacgg tgcaatgatc aacatgatct gatgcacgag    60
cgcaacgctc acaagttcat catctcatgg atctgcacat gaacaaacac cagagtcaaa   120
cgacgttgaa attgaggcta ctgcgccaat tgatgacaat acagacgatg ataacaaacc   180
gaagttatct gatgtagaaa aggattaaag atgctaagag atagtgatga tatttcataa   240

```
ataatgtaat tctatatatg ttaattacct tttttgcgag gcatatttat ggtgaaggat      300
aagttttgac catcaaagaa ggttaatgtg gctgtggttt cagggtccat aaagcttttc      360
aattcatctt ttttttttt gttctttttt ttgattccgg tttctttgaa attttttga       420 ttcggtaatc tccgagcaga aggaagaacg aaggaaggag cacagactta gattggtata     480
tatacgcata tgtggtgttg aagaaacatg aaattgccca gtattcttaa cccaactgca     540
cagaacaaaa acctgcagga aacgaagata atcatgtcg aaagctacat ataaggaacg      600
tgctgctact catcctagtc ctgttgctgc caagctattt aatatcatgc acgaaaagca     660
aacaaacttg tgtgcttcat tggatgttcg taccaccaag gaattactgg agttagttga    720
agcattaggt cccaaaattt gtttactaaa acacatgtg gatatcttga ctgattttc      780 catggagggc acagttaagc cgctaaaggc attatccgcc aagtacaatt ttttactctt    840
cgaagacaga aaatttgctg acattggtaa tacagtcaaa ttgcagtact ctgcgggtgt    900
atacagaata gcagaatggg cagacattac gaatgcacac ggtgtggtgg gcccaggtat   960
tgttagcggt ttgaagcagg cggcagaaga agtaacaaag gaacctagag gccttttgat  1020
gttagcagaa ttgtcatgca agggctccct atctactgga gaatatacta agggtactgt  1080
tgacattgcg aagagtgaca aagattttgt tatcggcttt attgctcaaa gagacatggg  1140
tggaagagat gaaggttacg attggttgat tatgacaccc ggtgtgggtt tagatgacaa  1200
gggagacgca ttgggtcaac agtatagaac cgtggatgat gtggtctcta caggatctga  1260
cattattatt gttggaagag gactatttgc aaagggaagg gatgctaagg tagagggtga  1320
acgttacaga aaagcaggct gggaagcata tttgagaaga tgcggccagc aaaactaaaa  1380
aactgtatta taagtaaatg catgtatact aaactcacaa attagagctt caatttaatt  1440
atatcagtta ttacccggga atctcggtcg taatgatttc tataatgacg aaaaaaaaa  1500 aattggaaag aaaaagcttc atggcccttta taaaaggaa ctatccaata cctcgccaga  1560
accaagtaac agtatttac ggggcacaaa tcaagaacaa taagacagga ctgtaaagat  1620
ggacgcatga tgcacgagcg caacgctcac aagatccgat cgaccgagaa ctgagaacgg  1680
tgcaatgatc aacatgatct                                               1700
```

<210> SEQ ID NO 90
<211> LENGTH: 1702
<212> TYPE: DNA
<213> ORGANISM: Artificial Sequence
<220> FEATURE:
<223> OTHER INFORMATION: xMarker xM0.URA.PI-MgaI

<400> SEQUENCE: 90

```
aagatccgat cgaccgagaa ctgagaacgg tgcaatgatc aacatgatct gcgtagctgc      60
ccagtatgag tcaggttcat catctcatgg atctgcacat gaacaaacac cagagtcaaa     120
cgacgttgaa attgaggcta ctgcgccaat tgatgacaat acagacgatg ataacaaacc     180
gaagttatct gatgtagaaa aggattaaag atgctaagag atagtgatga tatttcataa    240
ataatgtaat tctatatatg ttaattacct tttttgcgag gcatatttat ggtgaaggat     300
aagttttgac catcaaagaa ggttaatgtg gctgtggttt cagggtccat aaagcttttc     360
aattcatctt ttttttttt gttctttttt ttgattccgg tttctttgaa attttttga      420 ttcggtaatc tccgagcaga aggaagaacg aaggaaggag cacagactta gattggtata    480
tatacgcata tgtggtgttg aagaaacatg aaattgccca gtattcttaa cccaactgca    540
```

```
cagaacaaaa acctgcagga aacgaagata aatcatgtcg aaagctacat ataaggaacg      600
tgctgctact catcctagtc ctgttgctgc caagctattt aatatcatgc acgaaaagca      660
aacaaacttg tgtgcttcat tggatgttcg taccaccaag gaattactgg agttagttga      720
agcattaggt cccaaaattt gtttactaaa acacatgtg gatatcttga ctgattttc       780 catggagggc acagttaagc cgctaaaggc attatccgcc aagtacaatt ttttactctt      840
cgaagacaga aaatttgctg acattggtaa tacagtcaaa ttgcagtact ctgcgggtgt      900
atacagaata gcagaatggg cagacattac gaatgcacac ggtgtggtgg gcccaggtat      960
tgttagcggt ttgaagcagg cggcagaaga agtaacaaag gaacctagag gccttttgat     1020
gttagcagaa ttgtcatgca agggctccct atctactgga gaatatacta agggtactgt     1080
tgacattgcg aagagtgaca agatttttgt tatcggcttt attgctcaaa gagacatggg     1140
tggaagagat gaaggttacg attggttgat tatgacaccc ggtgtgggtt tagatgacaa     1200
gggagacgca ttgggtcaac agtatagaac cgtggatgat gtggtctcta caggatctga     1260
cattattatt gttggaagag gactatttgc aaagggaagg gatgctaagg tagagggtga     1320
acgttacaga aaagcaggct gggaagcata tttgagaaga tgcggccagc aaaactaaaa     1380
aactgtatta aagtaaatg catgtatact aaactcacaa attagagctt caatttaatt     1440
atatcagtta ttacccggga atctcggtcg taatgatttc tataatgacg aaaaaaaaaa     1500
aattggaaag aaaaagcttc atggccttta taaaaggaa ctatccaata cctcgccaga     1560
accaagtaac agtattttac ggggcacaaa tcaagaacaa taagacagga ctgtaaagat     1620
ggacgcatgc gtagctgccc agtatgagtc agaagatccg atcgaccgag aactgagaac     1680
ggtgcaatga tcaacatgat ct                                              1702
```

<210> SEQ ID NO 91
<211> LENGTH: 1732
<212> TYPE: DNA
<213> ORGANISM: Artificial Sequence
<220> FEATURE:
<223> OTHER INFORMATION: xMarker xM0.URA.PI-MtuII

<400> SEQUENCE: 91

```
aagatccgat cgaccgagaa ctgagaacgg tgcaatgatc aacatgatct acgtgcacta       60
cgtagagggt cgcaccgcac cgatctacaa gttcatcatc tcatggatct gcacatgaac      120
aaacaccaga gtcaaacgac gttgaaattg aggctactgc gccaattgat gacaatacag      180
acgatgataa caaaccgaag ttatctgatg tagaaaagga ttaaagatgc taagagatag      240
tgatgatatt tcataaataa tgtaattcta tatatgttaa ttaccttttt tgcgaggcat      300
atttatggtg aaggataagt tttgaccatc aaagaaggtt aatgtggctg tggtttcagg      360
gtccataaag cttttcaatt catctttttt tttttgttc ttttttttga ttccggtttc      420
tttgaaattt tttgattcg gtaatctccg agcagaagga agaacgaagg aaggagcaca      480
gacttagatt ggtatatata cgcatatgtg gtgttgaaga acatgaaat tgcccagtat      540 tcttaaccca actgcacaga acaaaaacct gcaggaaacg aagataaatc atgtcgaaag      600
ctacatataa ggaacgtgct gctactcatc ctagtcctgt tgctgccaag ctatttaata      660
tcatgcacga aaagcaaaca aacttgtgtg cttcattgga tgttcgtacc accaaggaat      720
tactggagtt agttgaagca ttaggtccca aaatttgttt actaaaaaca catgtggata      780
tcttgactga ttttccatg gagggcacag ttaagccgct aaaggcatta tccgccaagt      840
acaatttttt actcttcgaa gacagaaaat ttgctgacat tggtaataca gtcaaattgc      900
```

```
agtactctgc gggtgtatac agaatagcag aatgggcaga cattacgaat gcacacggtg    960
tggtgggccc aggtattgtt agcggtttga agcaggcggc agaagaagta acaaaggaac   1020
ctagaggcct tttgatgtta gcagaattgt catgcaaggg ctccctatct actggagaat   1080
atactaaggg tactgttgac attgcgaaga gtgacaaaga ttttgttatc ggctttattg   1140
ctcaaagaga catgggtgga agagatgaag gttacgattg gttgattatg acacccggtg   1200
tgggtttaga tgacaaggga gacgcattgg gtcaacagta tagaaccgtg gatgatgtgg   1260
tctctacagg atctgacatt attattgttg gaagaggact atttgcaaag ggaagggatg   1320
ctaaggtaga gggtgaacgt tacagaaaag caggctggga agcatatttg agaagatgcg   1380
gccagcaaaa ctaaaaaact gtattataag taaatgcatg tatactaaac tcacaaatta   1440
gagcttcaat ttaattatat cagttattac ccgggaatct cggtcgtaat gatttctata   1500
atgacgaaaa aaaaaaaatt ggaaagaaaa agcttcatgg cctttataaa aaggaactat   1560
ccaatacctc gccagaacca agtaacagta ttttacgggg cacaaatcaa gaacaataag   1620
acaggactgt aaagatggac gcatacgtgc actacgtaga gggtcgcacc gcaccgatct   1680
acaagatccg atcgaccgag aactgagaac ggtgcaatga tcaacatgat ct            1732

<210> SEQ ID NO 92
<211> LENGTH: 1716
<212> TYPE: DNA
<213> ORGANISM: Artificial Sequence
<220> FEATURE:
<223> OTHER INFORMATION: xMarker xM0.URA.VDE

<400> SEQUENCE: 92
aagatccgat cgaccgagaa ctgagaacgg tgcaatgatc aacatgatct tatgtcgggt     60
gcggagaaag aggtaatgaa agttcatcat ctcatggatc tgcacatgaa caaacaccag    120
agtcaaacga cgttgaaatt gaggctactg cgccaattga tgacaataca gacgatgata    180
acaaaccgaa gttatctgat gtagaaaagg attaaagatg ctaagagata gtgatgatat    240
ttcataaata atgtaattct atatatgtta attaccttt tttgcgaggca tatttatggt     300 gaaggataag ttttgaccat caaagaaggt taatgtggct gtggtttcag ggtccataaa    360
gcttttcaat tcatcttttt tttttttgtt cttttttttg attccggttt ctttgaaatt    420
tttttgattc ggtaatctcc gagcagaagg aagaacgaag gaaggagcac agacttagat    480
tggtatatat acgcatatgt ggtgttgaag aaacatgaaa ttgcccagta ttcttaaccc    540
aactgcacag aacaaaaacc tgcaggaaac gaagataaat catgtcgaaa gctacatata    600
aggaacgtgc tgctactcat cctagtcctg ttgctgccaa gctatttaat atcatgcacg    660
aaaagcaaac aaacttgtgt gcttcattgg atgttcgtac caccaaggaa ttactggagt    720
tagttgaagc attaggtccc aaaatttgtt tactaaaaac acatgtggat atcttgactg    780 attttttccat ggagggcaca gttaagccgc taaaggcatt atccgccaag tacaattttt    840
tactcttcga agacagaaaa tttgctgaca ttggtaatac agtcaaattg cagtactctg    900
cgggtgtata cagaatagca gaatgggcag acattacgaa tgcacacggt gtggtgggcc    960
caggtattgt tagcggtttg aagcaggcgg cagaagaagt aacaaaggaa cctagaggcc   1020
ttttgatgtt agcagaattg tcatgcaagg gctccctatc tactggagaa tatactaagg   1080
gtactgttga cattgcgaag agtgacaaag attttgttat cggctttatt gctcaaagag   1140
acatgggtgg aagagatgaa ggttacgatt ggttgattat gacacccggt gtgggtttag   1200
```

```
atgacaaggg agacgcattg ggtcaacagt atagaaccgt ggatgatgtg gtctctacag   1260
gatctgacat tattattgtt ggaagaggac tatttgcaaa gggaagggat gctaaggtag   1320
agggtgaacg ttacagaaaa gcaggctggg aagcatattt gagaagatgc ggccagcaaa   1380
actaaaaaac tgtattataa gtaaatgcat gtatactaaa ctcacaaatt agagcttcaa   1440
tttaattata tcagttatta cccgggaatc tcggtcgtaa tgatttctat aatgacgaaa   1500
aaaaaaaaat tggaaagaaa aagcttcatg gcctttataa aaaggaacta tccaatacct   1560
cgccagaacc aagtaacagt attttacggg gcacaaatca agaacaataa gacaggactg   1620
taaagatgga cgcattatgt cggggtgcgga gaaagaggta atgaaaaaga tccgatcgac   1680
cgagaactga gaacggtgca atgatcaaca tgatct                             1716
```

<210> SEQ ID NO 93
<211> LENGTH: 1604
<212> TYPE: DNA
<213> ORGANISM: Artificial Sequence
<220> FEATURE:
<223> OTHER INFORMATION: xMarker xM1.nat.F-CphI

<400> SEQUENCE: 93

```
cgttacgaag cacacactag ttagcgtcga gacacatagc gacgctagaa gatgcacgag     60
cgcaacgctc acaatcgaca ctagtaatac acatcatcgt cctacaagtt catcaaagtg    120
ttggacagac aactatacca gcatggatct cttgtatcgg ttcttttctc ccgctctctc    180
gcaataacaa tgaacactgg gtcaatcata gcctacacag gtgaacagag tagcgtttat    240
acagggttta tacggtgatt cctacggcaa aaatttttca tttctaaaaa aaaaaagaaa    300
aattttcctt tccaacgcta gaaggaaaag aaaaatctaa ttaaattgat ttggtgattt    360
tctgagagtt cccttttttca tatatcgaat tttgaatata aaaggagatc gaaaaaattt    420
ttctattcaa tctgtttttct ggttttattt gatagttttt ttgtgtatta ttattatgga    480
ttagtactgg tttatatggg ttttttctgta aacttctttt ttatttttagt ttgtttaatc    540 ttattttgag ttacattata gttccctaac tgcaagagaa gtaacattaa aaatgaccac    600
tcttgacgac acggcttacc ggtaccgcac cagtgtcccg ggggacgccg aggccatcga    660
ggcactggat gggtccttca ccaccgacac cgtcttccgc gtcaccgcca ccggggacgg    720
cttcaccctg cgggaggtgc cggtggaccc gccccctgacc aaggtgttcc ccgacgacga    780
atcggacgac gaatcggacg ccggggagga cggcgacccg gactcccgga cgttcgtcgc    840
gtacggggac gacggcgacc tggcgggctt cgtggtcgtc tcgtactccg gctggaaccg    900
ccggctgacc gtcgaggaca tcgaggtcgc cccggagcac cggggggcacg ggtcgggcg    960 cgcgttgatg gggctcgcga cggagttcgc ccgcgagcgg ggcgccgggc acctctggct   1020
ggaggtcacc aacgtcaacg caccggcgat ccacgcgtac cggcggatgg ggttcaccct   1080
ctgcggcctg acaccgcccc tgtacgacgg caccgcctcg gacggcgagc aggcgctcta   1140
catgagcatg ccctgcccct gagtttaact tgatactact agatttttc tcttcattta    1200 taaaattttt ggttataatt gaagctttag aagtatgaaa aatccttttt ttttcattct   1260
ttgcaaccaa aataagaagc ttcttttatt cattgaaatg atgaatataa acctaacaaa   1320
agaaaaagac tcgaatatca aacattaaaa aaaaataaaa gaggttatct gttttcccat   1380
ttagttggag tttgcatttt ctaatagata gaactctcaa ttaatgtgga tttagtttct   1440
ctgttcgttt tttttttgttt tgttctcact gtatttacat ttctatttag tatttagtta   1500
ttcatataat cttaacttct cgaggagctc gatgcacgag cgcaacgctc acaacgttac   1560
```

```
gaagcacaca ctagttagcg tcgagacaca tagcgacgct agaa            1604
```

<210> SEQ ID NO 94
<211> LENGTH: 1604
<212> TYPE: DNA
<213> ORGANISM: Artificial Sequence
<220> FEATURE:
<223> OTHER INFORMATION: xMarker xM4.nat.F-CphI

<400> SEQUENCE: 94

```
ttaatcagcg cccagagact agcactgaat gatcaacggg tagttcacac gatgcacgag     60
cgcaacgctc acaatcgaca ctagtaatac acatcatcgt cctacaagtt catcaaagtg    120
ttggacagac aactatacca gcatggatct cttgtatcgg ttcttttctc ccgctctctc    180
gcaataacaa tgaacactgg gtcaatcata gcctacacag gtgaacagag tagcgtttat    240
acagggttta tacggtgatt cctacggcaa aaattttttca tttctaaaaa aaaaaagaaa    300
aattttctt tccaacgcta gaaggaaaag aaaaatctaa ttaaattgat ttggtgattt     360
tctgagagtt ccctttttca tatatcgaat tttgaatata aaaggagatc gaaaaaattt    420
ttctattcaa tctgtttttct ggttttattt gatagttttt ttgtgtatta ttattatgga    480
ttagtactgg tttatatggg tttttctgta taacttcttt ttatttttagt ttgtttaatc    540
ttattttgag ttacattata gttccctaac tgcaagagaa gtaacattaa aaatgaccac    600
tcttgacgac acggcttacc ggtaccgcac cagtgtcccg ggggacgccg aggccatcga    660
ggcactggat gggtccttca ccaccgcacac cgtcttccgc gtcaccgcca ccggggacgg    720
cttcacctg cgggaggtgc cggtggaccc gcccctgacc aaggtgttcc ccgacgacga    780
atcggacgac gaatcggacg ccggggagga cggcgacccg gactcccgga cgttcgtcgc    840
gtacggggac gacggcgacc tggcgggctt cgtggtcgtc tcgtactccg gctggaaccg    900
ccggctgacc gtcgaggaca tcgaggtcgc cccggagcac cggggggcacg gggtcgggcg    960
cgcgttgatg gggctcgcga cggagttcgc ccgcgagcgg ggcgccgggc acctctggct   1020
ggaggtcacc aacgtcaacg caccggcgat ccacgcgtac cggcggatgg ggttcaccct   1080
ctgcggcctg gacaccgccc tgtacgacgg caccgcctcg gacggcgagc aggcgctcta   1140
catgagcatg ccctgcccct gagtttaact tgatactact agattttttc tcttcattta   1200
taaaattttt ggttataatt gaagctttag aagtatgaaa aaatccttt ttttcattct    1260
ttgcaaccaa aataagaagc ttctttatt cattgaaatg atgaatataa acctaacaaa   1320
agaaaaagac tcgaatatca aacattaaaa aaaataaaa gaggttatct gttttcccat   1380
ttagttggag tttgcatttt ctaatagata gaactctcaa ttaatgtgga tttagttct    1440
ctgttcgttt tttttttgttt tgttctcact gtatttacat ttctatttag tatttagtta    1500
ttcatataat cttaacttct cgaggagctc gatgcacgag cgcaacgctc acaattaatc   1560
agcgcccaga gactagcact gaatgatcaa cgggtagttc acac                   1604
```

<210> SEQ ID NO 95
<211> LENGTH: 2060
<212> TYPE: DNA
<213> ORGANISM: Artificial Sequence
<220> FEATURE:
<223> OTHER INFORMATION: xMarker xM2.hph.F-CphI

<400> SEQUENCE: 95

```
gtactgccta gtagaaacgg atctccacgt actagagtcc acctggtatc gatgcacgag     60
```

```
cgcaacgctc acaatcgaca ctagtaatac acatcatcgt cctacaagtt catcaaagtg      120
ttggacagac aactatacca gcatggatct cttgtatcgg ttcttttctc ccgctctctc      180
gcaataacaa tgaacactgg gtcaatcata gcctacacag gtgaacagag tagcgtttat      240
acagggttta tacggtgatt cctacggcaa aaattttttca tttctaaaaa aaaaaagaaa      300 aattttctt tccaacgcta gaaggaaaag aaaaatctaa ttaaattgat ttggtgattt       360
tctgagagtt cccttttttca tatatcgaat tttgaatata aaaggagatc gaaaaaattt     420
ttctattcaa tctgttttct ggttttattt gatagttttt ttgtgtatta ttattatgga     480
ttagtactgg tttatatggg ttttttctgta aacttctttt ttattttagt ttgtttaatc    540
ttattttgag ttacattata gttccctaac tgcaagagaa gtaacattaa aaatgaaaaa     600
gcctgaactc accgcgacgt ctgtcgagaa gtttctgatc gaaaagttcg acagcgtctc     660
cgacctgatg cagctctcgg agggcgaaga atctcgtgct ttcagcttcg atgtaggagg     720
gcgtggatat gtcctgcggg taaatagctg cgccgatggt ttctacaaag atcgttatgt     780
ttatcggcac tttgcatcgg ccgcgctccc gattccggaa gtgcttgaca ttggggaatt    840
cagcgagagc ctgacctatt gcatctcccg ccgtgcacag ggtgtcacgt tgcaagacct    900
gcctgaaacc gaactgcccg ctgttctgca gccggtcgcg gaggccatgg atgcgatcgc    960
tgcggccgat cttagccaga cgagcgggtt cggcccattc ggaccgcaag aatcggtca   1020 atacactaca tggcgtgatt tcatatgcgc gattgctgat ccccatgtgt atcactggca    1080
aactgtgatg gacgacaccg tcagtgcgtc cgtcgcgcag gctctcgatg agctgatgct   1140 tgggccgag gactgccccg aagtccggca cctcgtgcac gcggatttcg gctccaacaa    1200
tgtcctgacg gacaatggcc gcataacagc ggtcattgac tggagcgagg cgatgttcgg   1260
ggattcccaa tacgaggtcg ccaacatctt cttctggagg ccgtggttgg cttgtatgga   1320
gcagcagacg cgctacttcg agcggaggca tccggagctt gcaggatcgc cgcggctccg   1380
ggcgtatatg ctccgcattg gtcttgacca actctatcag agcttggttg acggcaattt   1440
cgatgatgca gcttgggcgc agggtcgatg cgacgcaatc gtccgatccg gagccgggac   1500
tgtcgggcgt acacaaatcg cccgcagaag cgcggccgtc tggaccgatg gctgtgtaga   1560
agtactcgcc gatagtggaa accgacgccc cagcactcgt ccgagggcaa aggaataggt    1620
ttaacttgat actactagat ttttctctt cattttataaa atttttggtt ataattgaag    1680
ctttagaagt atgaaaaaat ccttttttttt cattctttgc aaccaaaata agaagcttct    1740
tttattcatt gaaatgatga atataaacct aacaaaagaa aaagactcga atatcaaaca    1800
ttaaaaaaaa ataaaagagg ttatctgttt cccatttag ttggagtttg cattttctaa     1860
tagatagaac tctcaattaa tgtggattta gtttctctgt tcgtttttt ttgttttgtt     1920 ctcactgtat ttacatttct atttagtatt tagttattca tataatctta acttctcgag    1980
gagctcgatg cacgagcgca acgctcacaa gtactgccta gtagaaacgg atctccacgt    2040
actagagtcc acctggtatc                                                2060
```

```
<210> SEQ ID NO 96
<211> LENGTH: 1844
<212> TYPE: DNA
<213> ORGANISM: Artificial Sequence
<220> FEATURE:
<223> OTHER INFORMATION: xMarker xM3.kan.F-CphI

<400> SEQUENCE: 96
cgaggattaa cgtgtaaggc cctaagctat gtaccgcatc tcctaagaga gatgcacgag      60
```

```
cgcaacgctc acaatcgaca ctagtaatac acatcatcgt cctacaagtt catcaaagtg    120
ttggacagac aactatacca gcatggatct cttgtatcgg ttcttttctc ccgctctctc    180
gcaataacaa tgaacactgg gtcaatcata gcctacacag gtgaacagag tagcgtttat    240
acagggttta tacggtgatt cctacggcaa aaattttca tttctaaaaa aaaaaagaaa    300 aattttctt ccaacgcta gaaggaaaag aaaaatctaa ttaaattgat ttggtgattt    360
tctgagagtt cccttttttca tatatcgaat tttgaatata aaaggagatc gaaaaaattt    420
ttctattcaa tctgtttttct ggttttattt gatagttttt ttgtgtatta ttattatgga    480
ttagtactgg tttatatggg tttttctgta aacttctttt ttatttttagt ttgttttaatc    540 ttattttgag ttacattata gttccctaac tgcaagagaa gtaacattaa aaatgggtaa    600
ggaaaagact cacgtttcga ggccgcgatt aaattccaac atggatgctg atttatatgg    660
gtataaatgg gctcgcgata atgtcgggca atcaggtgcg acaatctatc gattgtatgg    720
gaagcccgat gcgccagagt tgtttctgaa acatggcaaa ggtagcgttg ccaatgatgt    780
tacagatgag atggtcagac taaactggct gacggaattt atgcctcttc cgaccatcaa    840
gcattttatc cgtactcctg atgatgcatg gttactcacc actgcgatcc ccggcaaaac    900
agcattccag gtattagaag aatatcctga ttcaggtgaa atattgttg atgcgctggc    960 agtgttcctg cgccggttgc attcgattcc tgtttgtaat tgtccttta acagcgatcg    1020 cgtatttcgt ctcgctcagg cgcaatcacg aatgaataac ggtttggttg atgcgagtga    1080
ttttgatgac gagcgtaatg gctggcctgt tgaacaagtc tggaaagaaa tgcataagct    1140
tttgccattc tcaccggatt cagtcgtcac tcatggtgat ttctcacttg ataaccttat    1200
ttttgacgag gggaaattaa taggttgtat tgatgttgga cgagtcggaa tcgcagaccg    1260
ataccaggat cttgccatcc tatggaactg cctcggtgag ttttctcctt cattacagaa    1320
acggcttttt caaaaatatg gtattgataa tcctgatatg aataaattgc agtttcattt    1380
gatgctcgat gagttttttct aagtttaact tgatactact agatttttc tcttcattta    1440 taaaatttt ggttataatt gaagcttag aagtatgaaa aaatcctttt ttttcattct    1500
ttgcaaccaa aataagaagc ttcttttatt cattgaaatg atgaatataa acctaacaaa    1560
agaaaaagac tcgaatatca acattaaaa aaaataaaa gaggttatct gttttcccat    1620
ttagttggag tttgcatttt ctaatagata gaactctcaa ttaatgtgga tttagtttct    1680
ctgttcgttt tttttttgttt tgttctcact gtatttacat ttctatttag tatttagtta    1740
ttcatataat cttaacttct cgaggagctc gatgcacgag cgcaacgctc acaacgagga    1800
ttaacgtgta aggccctaag ctatgtaccg catctcctaa gaga                     1844
```

<210> SEQ ID NO 97
<211> LENGTH: 1386
<212> TYPE: DNA
<213> ORGANISM: Artificial Sequence
<220> FEATURE:
<223> OTHER INFORMATION: xMarker xM6.zeo.F-CphI

<400> SEQUENCE: 97

```
gtcaaagcgc gattcgctag gaatgagagc gagaacgaac cggagtatat gatgcacgag     60
cgcaacgctc acaaaataca catcatcgtc ctacaagttc atcaaagtgt tggacagaca    120
actataccag catggatctc ttgtatcggt tcttttctcc cgctctctcg caataacaat    180
gaacactggg tcaatcatag cctacacagg tgaacagagt agcgtttata cagggtttat    240
```

```
acggtgattc ctacggcaaa aattttttcat ttctaaaaaa aaaaagaaaa attttttcttt      300 ccaacgctag aaggaaaaga aaaatctaat taaattgatt tggtgatttt ctgagagttc       360
cctttttcat atatcgaatt ttgaatataa aaggagatcg aaaaaatttt tctattcaat       420
ctgttttctg gttttatttg atagtttttt tgtgtattat tattatggat tagtactggt       480
ttatatgggt ttttctgtat aacttctttt tattttagtt tgtttaatct tattttgagt       540
tacattatag ttccctaact gcaagagaag taacattaaa aatggccaag ttgaccagtg       600
ccgttccggt gctcaccgcg cgcgacgtcg ccggagcggt cgagttctgg accgaccggc       660
tcgggttctc ccgggacttc gtggaggacg acttcgccgg tgtggtccgg gacgacgtga       720
ccctgttcat cagcgcggtc caggaccagg tggtgccgga acacccctg gcctgggtgt        780 gggtgcgcgg cctggacgag ctgtacgccg agtggtcgga ggtcgtgtcc acgaacttcc       840
gggacgcctc cgggccggcc atgaccgaga tcggcgagca gccgtggggg cgggagttcg       900
ccctgcgcga cccggccggc aactgcgtgc acttcgtggc cgaggagcag gactgagttt       960
aacttgatac tactagattt tttctcttca tttataaaat ttttggttat aattgaagct      1020
ttagaagtat gaaaaaatcc tttttttttca ttctttgcaa ccaaaataag aagcttcttt     1080
tattcattga aatgatgaat ataaacctaa caaaagaaaa agactcgaat atcaaacatt      1140
aaaaaaaaat aaaagaggtt atctgttttc ccatttagtt ggagtttgca ttttctaata     1200
gatagaactc tcaattaatg tggatttagt ttctctgttc gttttttttt gttttgttct     1260 cactgtatt acatttctat ttagtattta gttattcata taatcttaac ttgatgcacg      1320
agcgcaacgc tcacaagtca aagcgcgatt cgctaggaat gagagcgaga acgaaccgga      1380
gtatat                                                                 1386

<210> SEQ ID NO 98
<211> LENGTH: 1630
<212> TYPE: DNA
<213> ORGANISM: Artificial Sequence
<220> FEATURE:
<223> OTHER INFORMATION: xMarker s20M.URA.I-SceI

<400> SEQUENCE: 98
aagatccgat cgaccgagaa tagggataac agggtaatat gcgtccatct ttacagtcct       60
gtcttattgt tcttgatttg tgccccgtaa aatactgtta cttggttctg gcgaggtatt      120
ggatagttcc tttttataaa ggccatgaag cttttttcttt ccaatttttt ttttttcgtc     180
attatagaaa tcattacgac cgagattccc gggtaataac tgataataatt aaattgaagc    240 tctaatttgt gagtttagta tacatgcatt tacttataat acagtttttt agttttgctg      300
gccgcatctt ctcaaatatg cttcccagcc tgcttttctg taacgttcac cctctacctt      360
agcatccctt cccttttgcaa atagtcctct tccaacaata ataatgtcag atcctgtaga     420
gaccacatca tccacggttc tatactgttg acccaatgcg tctcccttgt catctaaacc      480
cacaccgggt gtcataatca accaatcgta accttcatct cttccaccca tgtctctttg     540
agcaataaag ccgataacaa atctttgtc actcttcgca atgtcaacag taccattagt      600
atattctcca gtagataggg agcccttgca tgacaattct gctaacatca aaaggcctct     660
aggttccttt gttacttctt ctgccgcctg cttcaaaccg ctaacaatac ctgggcccac    720
cacaccgtgt gcattcgtaa tgtctgccca ttctgctatt ctgtatacac ccgcagagta    780
ctgcaatttg actgtattac caatgtcagc aaatttctg tcttcgaaga gtaaaaaatt     840
gtacttggcg gataatgcct ttagcggctt aactgtgccc tccatggaaa aatcagtcaa    900
```

```
gatatccaca tgtgttttta gtaaacaaat tttgggacct aatgcttcaa ctaactccag      960
taattccttg gtggtacgaa catccaatga agcacacaag tttgtttgct tttcgtgcat     1020
gatattaaat agcttggcag caacaggact aggatgagta gcagcacgtt ccttatatgt     1080
agctttcgac atgatttatc ttcgtttcct gcaggttttt gttctgtgca gttgggttaa     1140
gaatactggg caatttcatg tttcttcaac accacatatg cgtatatata ccaatctaag     1200
tctgtgctcc ttccttcgtt cttccttctg ctcggagatt accgaatcaa aaaaatttca     1260
aagaaaccgg aatcaaaaaa aagaacaaaa aaaaaaaga tgaattgaaa agctttatgg     1320
accctgaaac cacagccaca ttaaccttct ttgatggtca aaacttatcc ttcaccataa     1380
atatgcctcg caaaaaaggt aattaacata tatagaatta cattatttat gaaatatcat     1440
cactatctct tagcatcttt aatccttttc tacatcagat aacttcggtt tgttatcatc     1500
gtctgtattg tcatcaattg gcgcagtagc ctcaatttca acgtcgtttg actctggtgt     1560
ttgttcatgt gcagatccat gagatgatga actagggata cagggtaat aagatccgat     1620 cgaccgagaa                                                              1630

<210> SEQ ID NO 99
<211> LENGTH: 1670
<212> TYPE: DNA
<213> ORGANISM: Artificial Sequence
<220> FEATURE:
<223> OTHER INFORMATION: xMarker s40M.URA.I-SceI

<400> SEQUENCE: 99
aagatccgat cgaccgagaa ctgagaacgg tgcaatgatc tagggataac agggtaatat       60
gcgtccatct ttacagtcct gtcttattgt tcttgatttg tgccccgtaa aatactgtta      120
cttggttctg gcgaggtatt ggatagttcc tttttataaa ggccatgaag ctttttcttt      180 ccaattttt ttttttcgtc attatagaaa tcattacgac cgagattccc gggtaataac      240
tgatataatt aaattgaagc tctaatttgt gagtttagta tacatgcatt tacttataat      300
acagtttttt agttttgctg gccgcatctt ctcaaatatg cttcccagcc tgcttttctg      360
taacgttcac cctctacctt agcatccctt cccttttgcaa atagtcctct tccaacaata      420
ataatgtcag atcctgtaga gaccacatca tccacggttc tatactgttg acccaatgcg      480
tctcccttgt catctaaacc cacaccgggt gtcataatca accaatcgta accttcatct      540
cttccaccca tgtctctttg agcaataaag ccgataacaa aatctttgtc actcttcgca      600
atgtcaacag tacccttagt atattctcca gtagataggg agcccttgca tgacaattct      660
gctaacatca aaaggcctct aggttccttt gttacttctt ctgccgcctg cttcaaaccg      720
ctaacaatac ctgggcccac cacaccgtgt gcattcgtaa tgtctgccca ttctgctatt      780
ctgtatacac ccgcagagta ctgcaatttg actgtattac caatgtcagc aaattttctg      840
tcttcgaaga gtaaaaaatt gtacttggcg gataatgcct ttagcggctt aactgtgccc      900
tccatggaaa aatcagtcaa gatatccaca tgtgttttta gtaaacaaat tttgggacct      960
aatgcttcaa ctaactccag taattccttg gtggtacgaa catccaatga agcacacaag     1020
tttgtttgct tttcgtgcat gatattaaat agcttggcag caacaggact aggatgagta     1080
gcagcacgtt ccttatatgt agctttcgac atgatttatc ttcgtttcct gcaggttttt     1140
gttctgtgca gttgggttaa gaatactggg caatttcatg tttcttcaac accacatatg     1200
cgtatatata ccaatctaag tctgtgctcc ttccttcgtt cttccttctg ctcggagatt     1260
```

| | |
|---|---:|
| accgaatcaa aaaaatttca aagaaaccgg aatcaaaaaa aagaacaaaa aaaaaaaga | 1320 |
| tgaattgaaa agctttatgg accctgaaac cacagccaca ttaaccttct ttgatggtca | 1380 |
| aaacttatcc ttcaccataa atatgcctcg caaaaaggt aattaacata tatagaatta | 1440 |
| cattatttat gaaatatcat cactatctct tagcatcttt aatccttttc tacatcagat | 1500 |
| aacttcggtt tgttatcatc gtctgtattg tcatcaattg gcgcagtagc ctcaatttca | 1560 |
| acgtcgtttg actctggtgt tgttcatgt gcagatccat gagatgatga actagggata | 1620 |
| acagggtaat aagatccgat cgaccgagaa ctgagaacgg tgcaatgatc | 1670 |

<210> SEQ ID NO 100
<211> LENGTH: 1710
<212> TYPE: DNA
<213> ORGANISM: Artificial Sequence
<220> FEATURE:
<223> OTHER INFORMATION: xMarker s60M.URA.I-SceI

<400> SEQUENCE: 100

| | |
|---|---:|
| aagatccgat cgaccgagaa ctgagaacgg tgcaatgatc aacatgatct gcgacgagct | 60 |
| tagggataac agggtaatat gcgtccatct ttacagtcct gtcttattgt tcttgatttg | 120 |
| tgccccgtaa aatactgtta cttggttctg gcgaggtatt ggatagttcc ttttataaa | 180 |
| ggccatgaag cttttctt ccaattttt ttttttcgtc attatagaaa tcattacgac | 240 |
| cgagattccc gggtaataac tgatataatt aaattgaagc tctaatttgt gagtttagta | 300 |
| tacatgcatt tacttataat acagtttttt agttttgctg gccgcatctt ctcaaatatg | 360 |
| cttcccagcc tgcttttctg taacgttcac cctctacctt agcatccctt cccttttgcaa | 420 |
| atagtcctct tccaacaata ataatgtcag atcctgtaga gaccacatca tccacggttc | 480 |
| tatactgttg acccaatgcg tctcccttgt catctaaacc cacaccgggt gtcataatca | 540 |
| accaatcgta accttcatct cttccaccca tgtctctttg agcaataaag ccgataacaa | 600 |
| aatctttgtc actcttcgca atgtcaacag taccccttagt atattctcca gtagataggg | 660 |
| agcccttgca tgacaattct gctaacatca aaaggcctct aggttccttt gttacttctt | 720 |
| ctgccgcctg cttcaaaccg ctaacaatac ctgggcccac cacaccgtgt gcattcgtaa | 780 |
| tgtctgccca ttctgctatt ctgtatacac ccgcagagta ctgcaatttg actgtattac | 840 |
| caatgtcagc aaattttctg tcttcgaaga gtaaaaaatt gtacttggcg gataatgcct | 900 |
| ttagcggctt aactgtgccc tccatggaaa aatcagtcaa gatatccaca tgtgttttta | 960 |
| gtaaacaaat tttgggacct aatgcttcaa ctaactccag taattccttg gtggtacgaa | 1020 |
| catccaatga agcacacaag tttgtttgct tttcgtgcat gatattaaat agcttggcag | 1080 |
| caacaggact aggatgagta gcagcacgtt ccttatatgt agctttcgac atgatttatc | 1140 |
| ttcgtttcct gcaggttttt gttctgtgca gttgggttaa gaatactggg caatttcatg | 1200 |
| tttcttcaac accacatatg cgtatatata ccaatctaag tctgtgctcc ttccttcgtt | 1260 |
| cttccttctg ctcggagatt accgaatcaa aaaatttca aagaaaccgg aatcaaaaaa | 1320 |
| aagaacaaaa aaaaaaaga tgaattgaaa agctttatgg accctgaaac cacagccaca | 1380 |
| ttaaccttct ttgatggtca aaacttatcc ttcaccataa atatgcctcg caaaaaggt | 1440 |
| aattaacata tatagaatta cattatttat gaaatatcat cactatctct tagcatcttt | 1500 |
| aatccttttc tacatcagat aacttcggtt tgttatcatc gtctgtattg tcatcaattg | 1560 |
| gcgcagtagc ctcaatttca acgtcgtttg actctggtgt tgttcatgt gcagatccat | 1620 |
| gagatgatga actagggata acagggtaat aagatccgat cgaccgagaa ctgagaacgg | 1680 |

-continued tgcaatgatc aacatgatct gcgacgagct        1710

<210> SEQ ID NO 101
<211> LENGTH: 62
<212> TYPE: DNA
<213> ORGANISM: Artificial Sequence
<220> FEATURE:
<223> OTHER INFORMATION: Primer KB589-324-35

<400> SEQUENCE: 101
atccccgcgt gcttggccgg ccgtatgttg atcccaaaga agaagagaaa ggtcgagttg        60
gg        62

<210> SEQ ID NO 102
<211> LENGTH: 51
<212> TYPE: DNA
<213> ORGANISM: Artificial Sequence
<220> FEATURE:
<223> OTHER INFORMATION: Primer 00177-JD-75AN

<400> SEQUENCE: 102
atccccgcgt gcttggccgg ccgtatgaag aacatcaaga agaaccaggt c        51

<210> SEQ ID NO 103
<211> LENGTH: 51
<212> TYPE: DNA
<213> ORGANISM: Artificial Sequence
<220> FEATURE:
<223> OTHER INFORMATION: Primer KB591-324-36

<400> SEQUENCE: 103
atccccgcgt gcttggccgg ccgtatgact aagttgtatt ctgacttgta c        51

<210> SEQ ID NO 104
<211> LENGTH: 45
<212> TYPE: DNA
<213> ORGANISM: Artificial Sequence
<220> FEATURE:
<223> OTHER INFORMATION: Primer KB592-324-36

<400> SEQUENCE: 104
atcggcgctc gcggcctgca ggttttagtt atggactgca aaacc        45

<210> SEQ ID NO 105
<211> LENGTH: 48
<212> TYPE: DNA
<213> ORGANISM: Artificial Sequence
<220> FEATURE:
<223> OTHER INFORMATION: Primer KB593-324-36

<400> SEQUENCE: 105
atcggcgctc gcggcctgca ggttttagtt atgaactact aatccctc        48

<210> SEQ ID NO 106
<211> LENGTH: 47
<212> TYPE: DNA
<213> ORGANISM: Artificial Sequence
<220> FEATURE:
<223> OTHER INFORMATION: Primer 00177-JD-75AO

<400> SEQUENCE: 106
atcggcgctc gcggcctgca ggttctactt gaggaacgtc tcggaag        47

<210> SEQ ID NO 107

```
<211> LENGTH: 52
<212> TYPE: DNA
<213> ORGANISM: Artificial Sequence
<220> FEATURE:
<223> OTHER INFORMATION: Primer KB595-324-36

<400> SEQUENCE: 107
atcggcgctc gcggcctgca ggttttactg atatcttttc aaatacttta tc      52

<210> SEQ ID NO 108
<211> LENGTH: 31
<212> TYPE: DNA
<213> ORGANISM: Artificial Sequence
<220> FEATURE:
<223> OTHER INFORMATION: Endonuclease recognition/cleavage site (ES)
      VDE (PI-SceI)

<400> SEQUENCE: 108
tatgtcgggt gcggagaaag aggtaatgaa a                              31

<210> SEQ ID NO 109
<211> LENGTH: 24
<212> TYPE: DNA
<213> ORGANISM: Artificial Sequence
<220> FEATURE:
<223> OTHER INFORMATION: Endonuclease recognition/cleavage site (ES)
      F-CphI

<400> SEQUENCE: 109
gatgcacgag cgcaacgctc acaa                                      24

<210> SEQ ID NO 110
<211> LENGTH: 24
<212> TYPE: DNA
<213> ORGANISM: Artificial Sequence
<220> FEATURE:
<223> OTHER INFORMATION: Endonuclease recognition/cleavage site (ES)
      PI-MgaI (pps1)

<400> SEQUENCE: 110
gcgtagctgc ccagtatgag tcag                                      24

<210> SEQ ID NO 111
<211> LENGTH: 40
<212> TYPE: DNA
<213> ORGANISM: Artificial Sequence
<220> FEATURE:
<223> OTHER INFORMATION: Endonuclease recognition/cleavage site (ES)
      PI-MtuII (pps1)

<400> SEQUENCE: 111
acgtgcacta cgtagagggt cgcaccgcac cgatctacaa                     40

<210> SEQ ID NO 112
<211> LENGTH: 18
<212> TYPE: DNA
<213> ORGANISM: Artificial Sequence
<220> FEATURE:
<223> OTHER INFORMATION: Endonuclease recognition/cleavage site (ES)
      I-SceI

<400> SEQUENCE: 112
tagggataac agggtaat                                             18

<210> SEQ ID NO 113
<211> LENGTH: 49
<212> TYPE: DNA
```

```
<213> ORGANISM: Artificial Sequence
<220> FEATURE:
<223> OTHER INFORMATION: Oligonucleotide KB411-266-26

<400> SEQUENCE: 113
aagatccgat cgaccgagaa tagggataac agggtaatcg actctagac         49

<210> SEQ ID NO 114
<211> LENGTH: 44
<212> TYPE: DNA
<213> ORGANISM: Artificial Sequence
<220> FEATURE:
<223> OTHER INFORMATION: Oligonucleotide KB412-266-26

<400> SEQUENCE: 114
gagtcgatta ccctgttatc cctattctcg gtcgatcgga tctt              44

<210> SEQ ID NO 115
<211> LENGTH: 69
<212> TYPE: DNA
<213> ORGANISM: Artificial Sequence
<220> FEATURE:
<223> OTHER INFORMATION: Oligonucleotide KB415-266-26

<400> SEQUENCE: 115
aagatccgat cgaccgagaa ctgagaacgg tgcaatgatc tagggataac agggtaatcg    60
actctagac                                                           69

<210> SEQ ID NO 116
<211> LENGTH: 64
<212> TYPE: DNA
<213> ORGANISM: Artificial Sequence
<220> FEATURE:
<223> OTHER INFORMATION: Oligonucleotide KB416-266-26

<400> SEQUENCE: 116
gagtcgatta ccctgttatc cctagatcat tgcaccgttc tcagttctcg gtcgatcgga    60
tctt                                                                64

<210> SEQ ID NO 117
<211> LENGTH: 64
<212> TYPE: DNA
<213> ORGANISM: Artificial Sequence
<220> FEATURE:
<223> OTHER INFORMATION: Oligonucleotide KB419-266-27

<400> SEQUENCE: 117
gagtcgtagg gataacaggg taataagatc cgatcgaccg agaactgaga acggtgcaat    60
gatc                                                                64

<210> SEQ ID NO 118
<211> LENGTH: 69
<212> TYPE: DNA
<213> ORGANISM: Artificial Sequence
<220> FEATURE:
<223> OTHER INFORMATION: Oligonucleotide KB420-266-27

<400> SEQUENCE: 118
gatcattgca ccgttctcag ttctcggtcg atcggatctt attaccctgt tatccctacg    60
actcgtcta                                                           69

<210> SEQ ID NO 119
<211> LENGTH: 46
```

```
-continued

<212> TYPE: DNA
<213> ORGANISM: Artificial Sequence
<220> FEATURE:
<223> OTHER INFORMATION: Oligonucleotide KB421-266-27

<400> SEQUENCE: 119
gagtcgaaga tccgatcgac cgagaactga gaacggtgca atgatc            46

<210> SEQ ID NO 120
<211> LENGTH: 40
<212> TYPE: DNA
<213> ORGANISM: Artificial Sequence
<220> FEATURE:
<223> OTHER INFORMATION: Oligonucleotide KB423-266-27

<400> SEQUENCE: 120
agctcgtcgc agatcatgtt gatcattgca ccgttctcag                   40

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide KB424-266-27

<400> SEQUENCE: 121
aacatgatct gcgacgagct                                         20

<210> SEQ ID NO 122
<211> LENGTH: 20
<212> TYPE: DNA
<213> ORGANISM: Artificial Sequence
<220> FEATURE:
<223> OTHER INFORMATION: Oligonucleotide KB425-266-27

<400> SEQUENCE: 122
ttctcggtcg atcggatctt                                         20

<210> SEQ ID NO 123
<211> LENGTH: 24
<212> TYPE: DNA
<213> ORGANISM: Artificial Sequence
<220> FEATURE:
<223> OTHER INFORMATION: Oligonucleotide KB426-266-27

<400> SEQUENCE: 123
gagtcgatta ccctgttatc ccta                                    24

<210> SEQ ID NO 124
<211> LENGTH: 40
<212> TYPE: DNA
<213> ORGANISM: Artificial Sequence
<220> FEATURE:
<223> OTHER INFORMATION: Oligonucleotide KB427-266-27

<400> SEQUENCE: 124
aagatccgat cgaccgagaa ctgagaacgg tgcaatgatc                   40

<210> SEQ ID NO 125
<211> LENGTH: 49
<212> TYPE: DNA
<213> ORGANISM: Artificial Sequence
<220> FEATURE:
<223> OTHER INFORMATION: Oligonucleotide KB428-266-27

<400> SEQUENCE: 125
```
aacatgatct gcgacgagct tagggataac agggtaatcg actctagac          49

<210> SEQ ID NO 126
<211> LENGTH: 49
<212> TYPE: DNA
<213> ORGANISM: Artificial Sequence
<220> FEATURE:
<223> OTHER INFORMATION: Oligonucleotide KB429-266-27

<400> SEQUENCE: 126
ttctcggtcg atcggatctt attaccctgt tatccctacg actcgtcta          49

<210> SEQ ID NO 127
<211> LENGTH: 31
<212> TYPE: DNA
<213> ORGANISM: Artificial Sequence
<220> FEATURE:
<223> OTHER INFORMATION: Oligonucleotide KB430-266-28

<400> SEQUENCE: 127
ttctcggtcg atcggatctt cgactcgtct a                             31

<210> SEQ ID NO 128
<211> LENGTH: 44
<212> TYPE: DNA
<213> ORGANISM: Artificial Sequence
<220> FEATURE:
<223> OTHER INFORMATION: Oligonucleotide KB431-266-28

<400> SEQUENCE: 128
gagtcgatta ccctgttatc cctagtcagc catttgcatc ctca               44

<210> SEQ ID NO 129
<211> LENGTH: 40
<212> TYPE: DNA
<213> ORGANISM: Artificial Sequence
<220> FEATURE:
<223> OTHER INFORMATION: Oligonucleotide KB432-266-28

<400> SEQUENCE: 129
aacatgatct gcgacgagct tgaggatgca aatggctgac                    40

<210> SEQ ID NO 130
<211> LENGTH: 29
<212> TYPE: DNA
<213> ORGANISM: Artificial Sequence
<220> FEATURE:
<223> OTHER INFORMATION: Oligonucleotide KB433-266-28

<400> SEQUENCE: 130
tagggataac agggtaatcg actctagac                                29

<210> SEQ ID NO 131
<211> LENGTH: 20
<212> TYPE: DNA
<213> ORGANISM: Artificial Sequence
<220> FEATURE:
<223> OTHER INFORMATION: Oligonucleotide KB434-266-28

<400> SEQUENCE: 131
gtcagccatt tgcatcctca                                          20

<210> SEQ ID NO 132
<211> LENGTH: 25
<212> TYPE: DNA
<213> ORGANISM: Artificial Sequence

```
<220> FEATURE:
<223> OTHER INFORMATION: Oligonucleotide KB439-266-34

<400> SEQUENCE: 132
taatatgcgt ccatctttac agtcc                                         25

<210> SEQ ID NO 133
<211> LENGTH: 26
<212> TYPE: DNA
<213> ORGANISM: Artificial Sequence
<220> FEATURE:
<223> OTHER INFORMATION: Oligonucleotide KB440-266-34

<400> SEQUENCE: 133
cctagttcat catctcatgg atctgc                                        26

<210> SEQ ID NO 134
<211> LENGTH: 26
<212> TYPE: DNA
<213> ORGANISM: Artificial Sequence
<220> FEATURE:
<223> OTHER INFORMATION: Oligonucleotide KB441-266-34

<400> SEQUENCE: 134
tcttgttcat catctcatgg atctgc                                        26

<210> SEQ ID NO 135
<211> LENGTH: 44
<212> TYPE: DNA
<213> ORGANISM: Artificial Sequence
<220> FEATURE:
<223> OTHER INFORMATION: Oligonucleotide KB464-266-58

<400> SEQUENCE: 135
gagtcgtagg gataacaggg taataagatc cgatcgaccg agaa                    44

<210> SEQ ID NO 136
<211> LENGTH: 1750
<212> TYPE: DNA
<213> ORGANISM: Artificial Sequence
<220> FEATURE:
<223> OTHER INFORMATION: xMarker s80M.URA.I-SceI

<400> SEQUENCE: 136
aagatccgat cgaccgagaa ctgagaacgg tgcaatgatc aacatgatct gcgacgagct    60
tgaggatgca aatggctgac tagggataac agggtaatat gcgtccatct ttacagtcct   120
gtcttattgt tcttgatttg tgccccgtaa aatactgtta cttggttctg gcgaggtatt   180
ggatagttcc tttttataaa ggccatgaag cttttttcttt ccatttttttt tttttcgtc   240 attatagaaa tcattacgac cgagattccc gggtaataac tgatataatt aaattgaagc   300
tctaatttgt gagtttagta tacatgcatt tacttataat acagtttttt agttttgctg   360
gccgcatctt ctcaaatatg cttcccagcc tgcttttctg taacgttcac cctctacctt   420
agcatccctt ccctttgcaa atagtcctct tccaacaata ataatgtcag atcctgtaga   480
gaccacatca tccacggttc tatactgttg acccaatgcg tctcccttgt catctaaacc   540
cacaccgggt gtcataatca accaatcgta accttcatct cttccaccca tgtctctttg   600
agcaataaag ccgataacaa atctttgtc actcttcgca atgtcaacag tacccttagt   660
atattctcca gtagataggg agcccttgca tgacaattct gctaacatca aaaggcctct   720
aggttccttt gttacttctt ctgccgcctg cttcaaaccg ctaacaatac ctgggcccac   780
```

```
cacaccgtgt gcattcgtaa tgtctgccca ttctgctatt ctgtatacac ccgcagagta    840
ctgcaatttg actgtattac caatgtcagc aaatttctg tcttcgaaga gtaaaaaatt     900
gtacttggcg gataatgcct ttagcggctt aactgtgccc tccatggaaa aatcagtcaa    960
gatatccaca tgtgttttta gtaaacaaat tttgggacct aatgcttcaa ctaactccag   1020
taattccttg gtggtacgaa catccaatga agcacacaag tttgtttgct tttcgtgcat   1080
gatattaaat agcttggcag caacaggact aggatgagta gcagcacgtt ccttatatgt   1140
agctttcgac atgatttatc ttcgtttcct gcaggttttt gttctgtgca gttgggttaa   1200
gaatactggg caatttcatg tttcttcaac accacatatg cgtatatata ccaatctaag   1260
tctgtgctcc ttccttcgtt cttccttctg ctcggagatt accgaatcaa aaaaatttca   1320
aagaaaccgg aatcaaaaaa aagaacaaaa aaaaaaaaga tgaattgaaa agctttatgg   1380
accctgaaac cacagccaca ttaaccttct ttgatggtca aaacttatcc ttcaccataa   1440
atatgcctcg caaaaaaggt aattaacata tatagaatta cattatttat gaaatatcat   1500
cactatctct tagcatcttt aatccttttc tacatcagat aacttcggtt tgttatcatc   1560
gtctgtattg tcatcaattg gcgcagtagc ctcaatttca acgtcgtttg actctggtgt   1620
ttgttcatgt gcagatccat gagatgatga actagggata acagggtaat aagatccgat   1680
cgaccgagaa ctgagaacgg tgcaatgatc aacatgatct gcgacgagct tgaggatgca   1740
aatggctgac                                                          1750
```

<210> SEQ ID NO 137
<211> LENGTH: 35
<212> TYPE: DNA
<213> ORGANISM: Artificial Sequence
<220> FEATURE:
<223> OTHER INFORMATION: Figure 3 synthetic oligo 1
<220> FEATURE:
<221> NAME/KEY: misc_feature
<222> LOCATION: (28)..(35)
<223> OTHER INFORMATION: N = A, G, C or T

<400> SEQUENCE: 137
accgatagtt acgatcgagg tactcatnnn nnnnn                               35

<210> SEQ ID NO 138
<211> LENGTH: 34
<212> TYPE: DNA
<213> ORGANISM: Artificial Sequence
<220> FEATURE:
<223> OTHER INFORMATION: Figure 3 synthetic oligo 2
<220> FEATURE:
<221> NAME/KEY: misc_feature
<222> LOCATION: (28)..(34)
<223> OTHER INFORMATION: N = A, G, C or T

<400> SEQUENCE: 138
agtagtacct cgatcgtaac tatcggtnnn nnnn                                34

<210> SEQ ID NO 139
<211> LENGTH: 35
<212> TYPE: DNA
<213> ORGANISM: Artificial Sequence
<220> FEATURE:
<223> OTHER INFORMATION: Figure 3 synthetic oligo 3
<220> FEATURE:
<221> NAME/KEY: misc_feature
<222> LOCATION: (28)..(35)
<223> OTHER INFORMATION: N = A, G, C or T

<400> SEQUENCE: 139
accgatagtt acgatcgagg tactactnnn nnnnn            35

<210> SEQ ID NO 140
<211> LENGTH: 34
<212> TYPE: DNA
<213> ORGANISM: Artificial Sequence
<220> FEATURE:
<223> OTHER INFORMATION: Figure 3 synthetic oligo 4
<220> FEATURE:
<221> NAME/KEY: misc_feature
<222> LOCATION: (28)..(35)
<223> OTHER INFORMATION: N = A, G, C or T

<400> SEQUENCE: 140
agtagtacct cgatcgtaac tatcggtnnn nnnn             34

<210> SEQ ID NO 141
<211> LENGTH: 36
<212> TYPE: DNA
<213> ORGANISM: Artificial Sequence
<220> FEATURE:
<223> OTHER INFORMATION: Figure 4 synthetic oligo 3

<400> SEQUENCE: 141
accgatagtt acgatcgagg tactcattag ggataa           36

<210> SEQ ID NO 142
<211> LENGTH: 41
<212> TYPE: DNA
<213> ORGANISM: Artificial Sequence
<220> FEATURE:
<223> OTHER INFORMATION: Figure 4 synthetic oligo 4

<400> SEQUENCE: 142
agtagtacct cgatcgtaac tatcggttat taccctgtta t     41

<210> SEQ ID NO 143
<211> LENGTH: 27
<212> TYPE: DNA
<213> ORGANISM: Artificial Sequence
<220> FEATURE:
<223> OTHER INFORMATION: Figure 4 synthetic oligo 5

<400> SEQUENCE: 143
accgatagtt acgatcgagg tactcat                     27

<210> SEQ ID NO 144
<211> LENGTH: 27
<212> TYPE: DNA
<213> ORGANISM: Artificial Sequence
<220> FEATURE:
<223> OTHER INFORMATION: Figure 4 synthetic oligo 6

<400> SEQUENCE: 144
atgagtacct cgatcgtaac tatcggt                     27

<210> SEQ ID NO 145
<211> LENGTH: 198
<212> TYPE: DNA
<213> ORGANISM: Artificial Sequence
<220> FEATURE:
<223> OTHER INFORMATION: 198mer-direct Rabit 606

<400> SEQUENCE: 145
tcactattat tccataagat gatcattagc attacgttca aaacgagtac aaataactta    60

-continued

```
agtaataaca cgagccatat gaccattagc aagatgacaa gcaagttaag accaatcagc    120
ttccatcata gcatcagctt aacgttcacc attaataaga gtagaaattt caccttcaag    180
acaataacga ttttcgtg                                                  198
```